United States Patent [19]
Fukushi et al.

[11] Patent Number: 5,935,963
[45] Date of Patent: Aug. 10, 1999

[54] PIPERAZINONES, THEIR PRODUCTION AND USE

[75] Inventors: Hideto Fukushi, Hyogo; Takehiko Naka, Higashinada-ku; Zen-ichi Terashita, Osaka; Toshio Miyawaki, Hyogo, all of Japan

[73] Assignee: Takeda Chemical Industries, Ltd, Osaka, Japan

[21] Appl. No.: 08/669,375

[22] PCT Filed: Apr. 25, 1996

[86] PCT No.: PCT/JP96/01139

§ 371 Date: Jul. 10, 1996

§ 102(e) Date: Jul. 10, 1996

[87] PCT Pub. No.: WO96/33982

PCT Pub. Date: Oct. 31, 1996

[30] Foreign Application Priority Data

Apr. 26, 1995 [JP] Japan ................................. 7-101911
Aug. 9, 1995 [JP] Japan ................................. 7-203132
Mar. 29, 1996 [JP] Japan ................................. 8-077867

[51] Int. Cl.$^6$ ..................... A61K 31/495; C07D 241/08; C07D 413/12
[52] U.S. Cl. .......................... 514/255; 514/252; 544/367; 544/384
[58] Field of Search ................... 544/367, 384; 514/252, 255

[56] References Cited

U.S. PATENT DOCUMENTS

| 5,294,713 | 3/1994 | Sugihara et al. | 544/384 |
| 5,378,712 | 1/1995 | Alig et al. | 514/315 |
| 5,493,007 | 2/1996 | Burnier et al. | 530/317 |
| 5,541,343 | 7/1996 | Himmelsbach et al. | 514/424 |
| 5,545,658 | 8/1996 | Alig et al. | 514/423 |
| 5,550,131 | 8/1996 | Sugihara et al. | 514/255 |

FOREIGN PATENT DOCUMENTS

| 650488 | 5/1992 | Australia . |
| 0 406 428 | 1/1991 | European Pat. Off. . |
| 0 505 868 | 9/1992 | European Pat. Off. . |
| 0 643 072 | 3/1995 | European Pat. Off. . |
| 0 709 085 A1 | 5/1996 | European Pat. Off. . |
| 2-174797 | 7/1990 | Japan . |
| 4-264068 | 9/1992 | Japan . |
| 0 529 858 | 3/1993 | Japan . |
| 6-509551 | 10/1994 | Japan . |
| 91/15515 | 10/1991 | WIPO . |
| 92/17492 | 10/1992 | WIPO . |

OTHER PUBLICATIONS

Takenaka et al Chemical Abstracts, vol. 120, No. 31211v, p. 903, col. 1, Jan. 17, 1994.
Takenaka et al Chemistry Express, vol. 8, No. 9., "Preparation of optically active N,N$^1$–ethylene–bridged dipetides as units of pseudopeptides"., pp. 697–700, 1993.
Ruoslahti et al, Science, vol. 238, pp. 491–486 (1987).
Pierschbacher et al Journal of Biological Chemical vol. 262, No. 35, pp. 17294–17297, Dec. 15, 1987.
Receptor Data for Biological Experiments by Doods and van Meel, pp. 112–117 (1991).

Primary Examiner—Emily Bernhardt
Attorney, Agent, or Firm—Foley & Lardner

[57] ABSTRACT

The present invention provides compounds and medicines effective for prophylaxis and therapy of various diseases by controlling or inhibiting cell-adhesion. Especially, the compounds of this invention perform platelet aggregation action without remarkable elongation of hemorrhagic period and can be used as a safe and long-acting antithrombotic drug as compared with known substances showing the same activity. Compounds of this invention are piperazinones of the formula $$A^1-D-\overset{O}{\underset{\|}{C}}-\overset{R^{1'}}{\underset{|}{N}}-\overset{R^2}{\underset{|}{CH}}-\overset{O}{\underset{\|}{C}}-N\underset{\underset{(CH_2)_n-P-A^2}{|}}{\overset{\diagup}{\diagdown}}\underset{O}{\overset{N}{\diagdown}}Y$$

6 Claims, No Drawings

PIPERAZINONES, THEIR PRODUCTION AND USE

TECHNICAL FIELD

This invention relates to novel piperazinones having a platelet aggregation inhibitory action, whose undesirable side effects are slight, or a salt thereof and to a pharmaceutical composition for inhibiting cell-adhesion comprising them as effective components.

BACKGROUND ART

The present invention relates to novel piperazinones having an excellent controlling or inhibiting action cell-adhesion and to the pharmaceutical composition for various diseases.

As the factors participating in adhesion to extracellular substrate of animal cells, there have been known fibronectin, vitronectin, osteopontin, collagen, thrombospondin, fibrinogen and von willebrand factor. These proteins include -Arg-Gly-Asp- as cell recognition site. This tripeptide is recognized by at least one protein belonging to receptors integrins, which are heterodimeric proteins consisting of sub-units combined to two membranes [Science, 238, 491 (1987)].

Structurally related integrin receptors, which recognize the amino acid sequence -Arg-Gly-Asp-, are known to express at extracellular surface glycoprotein of platelets, endothelial cells, leucocyte, lymphocyte, monocyte and granulocyte. Compounds having the amino acid sequence -Arg-Gly-Asp- are competitively bound to the site to be bound with intracellular adhesive factors to thereby inhibit the binding of intracellular adhesive factors. As such substances for inhibiting intracellular adhesion, there have been known, for example, H-Gly-Arg-Gly-Asp-Ser-Pro—OH.

When blood vessels are injured, platelets are activated with, for example, endothelial collagens, which causes binding of fibrinogen to platelets, i.e. platelet aggregation, to form thrombus. The interaction between platelets and fibrinogen takes place through GP IIb/IIIa, this being an important characteristic feature of platelet aggregation. Cell adhesion-inhibiting substances can inhibit platelet aggregation due to substances causing platelet aggregation such as thrombin, epinephrine, ADP and collagen.

Besides, cell-adhesion inhibiting substances are expected as drugs for suppression of metastasis of tumor cells (inhibition of fixed adhesion at the site where the tumor cells are migrated).

Linear or cyclic peptides containing the amino acid sequence, -Arg-Gly-Asp- (RGD) have been known as cell-adhesion inhibiting substances [Journal of Biological Chemistry (J. Biol. Chem.), 262, 17294 (1987) and Japanese published unexamined patent application No. 174797/1990, among others].

And, non-peptide compounds having an antithrombotic action are disclosed in Japanese published unexamined patent application No. 264068/1992 and EPA 505868, in which compounds having 4- to 7-membered cyclic alkyleneimino such as pyrrolidine ring and compounds having e.g. piperidine ring are respectively described. Further, compounds having piperidinone ring, which have cell-adhesion inhibiting action, are disclosed in EPA 529858. And, such drugs as aspirin, heparin and ticlopidine are known to show undesirable side effects such as prolongation of bleeding time. As known platelet aggregation inhibiting substances which are slight in the action of prolonging bleeding time, cyclic peptide derivatives are described in Japanese publication of translations of International patent application No. 509551/1994.

DISCLOUSURE OF INVENTION

These known peptide derivatives mentioned above are not satisfactory in the potency of their activity, and their oral absorbability is not satisfactory from the practical viewpoint. Besides, since these peptide derivatives are hydrolyzed with enzymes including aminopeptidase, carboxypeptidase or various types of endopeptidase, e.g. serineprotease, their stability in a solution containing these enzymes or in a living body is not satisfactory. Therefore, for clinical application of these peptide derivatives, there are problems still to be solved.

And, in the non-peptide compounds having an antithrombotic action, compounds having higher potency durable for a longer period as compared with the above-mentioned known compounds having an antithrombotic action have been sought for.

Further, in the known platelet aggregation inhibiting substances which are slight in the action of prolonging bleeding time, they are far from being satisfactory in the durability of the action of oral absorbability. Therefore, such compounds as showing longer durability and capable of being administered orally have been sought for.

The present inventors diligently made extensive studies and, as a result, they succeeded in synthesizing a compound, whose characteristic feature in the chemical structure lies in having proton-accepting groups respectively at terminals of substituents at 3- and 4-positions of the piperazine ring, represented by the formula (I)

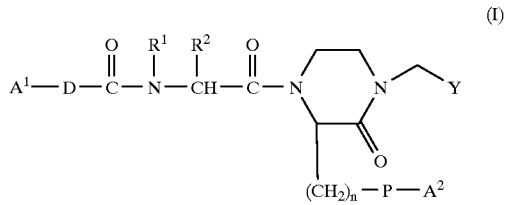

wherein $A^1$ and $A^2$ independently are a proton-accepting group or a group convertible into a proton-accepting group; D is a spacer having a 2- to 6-atomic chain optionally bonded through a hetero-atom and/or a 5- or 6-membered ring (provided that the 5- or 6-membered ring is, depending on its bonding position, counted as 2- or 3-atomic chain); $R^1$ is a hydrogen atom or a hydrocarbon group; $R^2$ is a hydrogen atom or a residual group formed by removing —CH(NH$_2$)COOH from an α-amino acid, or $R^1$ and $R^2$ may be combined to form a 5- or 6-membered ring; P is a spacer having a 1- to 10-atomic chain optionally bonded through a hetero-atom and/or a 5- or 6-membered ring (provided that the 5- or 6-membered ring is, depending on its bonding position, counted as 2- or 3-atomic chain); Y is an optionally esterified or amidated carboxyl group; and n denotes an integer of 0 to 8, and further found that the compound thus synthesized unexpectedly possesses, based on the chemical structural characteristic feature, a potent, durable and safely administrable (i.e. slight in undesirable side effects such as prolongation of bleeding time) platelet aggregation inhibiting action.

Based on the finding, the present invention was accomplished.

More specifically, the present invention relates to
(1) the compound (I) or a salt thereof,
(2) a compound as described in (1) above, wherein $A^1$ and $A^2$ independently are an optionally substituted amino, amidino or guanidino group or a group convertible to them, (3) a compound as described in (1) above, wherein $A^1$ and $A^2$ independently are an optionally substituted oxadiazolyl or thiaziazolyl group, (4) a compound as described in (1) above, wherein $A^1$ and $A^2$ independently are (1) an amidino or guanidino group which may be substituted with $C_{2-8}$ alkoxycarbonyl, or (2) an amino group which may be substituted with an oxadiazolyl group which may be substituted with oxo or $C_{1-4}$ alkyl which may be substituted with halogen, (5) a compound as described in (1) above, wherein $A^1$ and $A^2$ independently are an unsubstituted amino, amidino or guanidino group, (6) a compound as described in (1) above, wherein D is group of the formula:

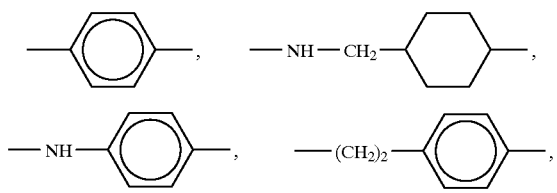

(7) a compound as described in (1) above, wherein $R^1$ is a hydrogen atom, (8) a compound as described in (1) above, wherein $R^2$ is a hydrogen atom or a $C_{1-4}$ alkyl group substituted with phenyl optionally substituted with $C_{1-4}$ alkoxy, (9) a compound as described in (1) above, wherein P is a group of the formula:

in which Z is

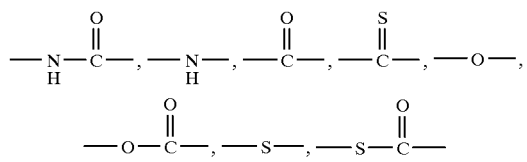

in which either bond may be bonded to B, or a bond; and B is

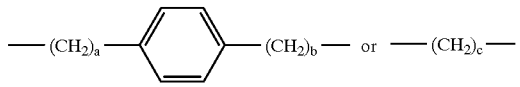

(i)

in which a is an integer of 0 to 2, b is an integer of 0 to 2 and c is an integer of 1 to 5, or (ii) a bond, excepting the case where Z and B both are a bond,

(10) a compound as described in (9) above, wherein Z is

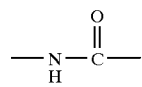

in which either bond may be bonded to B,

(11) a compound as described in (9) above, wherein B is

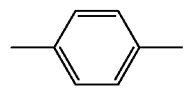

or $—(CH_2)_d—$ in which d is an integer of 1 to 4,

(12) a compound as described in (1) above, wherein Y is a carboxyl group or a $C_{1-6}$ alkoxy-carbonyl group,

(13) a compound as described in (1) above, wherein n is an integer of 1 to 4,

(14) a compound as described in (1) above, wherein n is 2 or 3,

(15) a compound as described in (1) above, wherein $A^1$ and $A^2$ independently are
  1) an amidino or guanidino group optionally substituted with $C_{2-8}$ alkoxycarbonyloxy,
  2) an amino group optionally substituted with oxadiozolyl optionally substituted with oxo or $C_{1-4}$ alkyl optionally substituted with halogen, or
  3) an oxadiazolyl group optionally substituted with oxo or $C_{1-4}$ alkyl optionally substituted with halogen, D is a group of the formula:

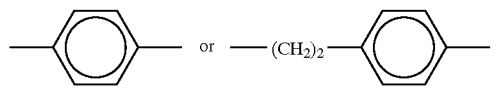

$R^1$ is a hydrogen atom, $R^2$ is a hydrogen atom or a $C_{1-4}$ alkyl group substituted with phenyl optionally substituted with $C_{1-4}$ alkoxy, P is a group of the formula: —Z—B—
  wherein Z is

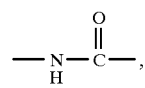

a bond or

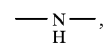

and B is

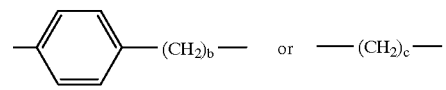

in which b is 0 or 1, and c is an integer of 1 to 5, Y is a group of the formula:

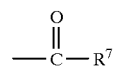

wherein $R^7$ is 1) hydroxy group, 2) a $C_{1-8}$ alkoxy or $C_{2-12}$ alkenyloxy group which may be substituted with $C_{1-4}$ alkoxy-carbonyl or 5-methyl-2-oxo-1,3-dioxolen-4-yl, or 3) a group of the formula: —OCH$(R^{7a})$OCOR$^8$ in which $R^{7a}$ is a hydrogen atom or a $C_{1-6}$ alkyl group, and $R^8$ is a $C_{1-6}$ alkyl group or a $C_{5-7}$ cycloalkyloxy group, and n is an integer of 1 to 4,

(16) a compound as described in (1) above, wherein $A^1$ and $A^2$ are independently
  1) an amidino or guanidino group optionally substituted with methoxycarbonyl or
  2) an amino group optionally substituted with 5-oxo-1,2,4-oxodiazol-3-yl or 5-trifluoromethyl-1,2,4-oxadiazol-3-yl, D is

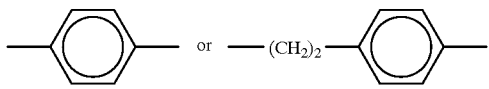

$R^1$ is a hydrogen atom,
$R^2$ is a hydrogen atom or p-methoxybenzyl,
P is

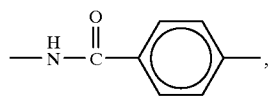

Y is a carboxyl group and
n is 2 or 3,

(17) a compound as described in (1) above, wherein $A^1$ and $A^2$ are independently an unsubstituted amino, amidino or guanidino group and $R^2$ is a hydrogen atom,

(18) a pharmaceutical composition for comprises a compound as described in (1) above or a salt thereof,

(19) a pharmaceutical composition for inhibiting cell-adhesion which comprises a compound as described in (1) above or a salt thereof,

(20) a pharmaceutical composition for treating or preventing angina pectoris, which comprises a compound as described in (1) above or a salt thereof, in admixture with a pharmaceutically acceptable carrier or excipient,

(21) a pharmaceutical composition for treating or preventing unstable angina, which comprises a compound as described in (1) above or a salt thereof, admixture with a pharmaceutically acceptable carrier or excipient,

(22) a pharmaceutical composition for treating or preventing ischemic complication, reobstruction or restenosis after percutaneous transluminal coronary angioplasty or cornary thrombolytic therapy, which comprises a compound as described in (1) above or a salt thereof, admixture with a pharmaceutically acceptable carrier or excipient, and

(23) a process for producing a compound as described in (1) above, which comprises reacting a compound of the formula

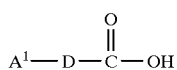

wherein the symbols are as defined in (1) above or a reactive derivative thereof, or a salt thereof, with a compound of the formula

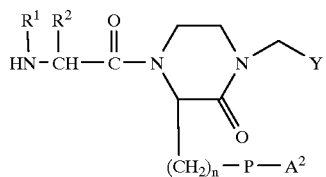

wherein the symbols are as defined in claim 1, or a salt thereof.

In the above formula (I), $A^1$ and $A^2$ independently are a proton-accepting group or a group convertible into a proton-accepting group.

In the above formula (I), the proton-accepting group means a group which accepts proton from a relevant group, namely a Bronsted base as exemplified by a group containing nitrogen atom capable of being positively charged. Specific examples of the proton-accepting group include optionally substituted amino, amidino and guanidino groups. Preferable examples of the proton-accepting group include unsubstituted amino, amidino and guanidino groups, or secondary or tertiary amino groups (especially ethylamino), amidino or guanidino groups substituted with a $C_{1-4}$ alkyl group.

Examples of the substituents of optionally substituted amino, amidino and guanidino groups include chain-like or cyclic hydrocarbon groups such as $C_{1-6}$ alkyl groups (e.g. methyl, ethyl, propyl, isopropyl, butyl, sec-butyl, tert-butyl, pentyl and hexyl), $C_{2-6}$ alkenyl groups (e.g. vinyl, allyl, isopropenyl, butenyl, isobutenyl and sec-butenyl), $C_{2-6}$ alkynyl groups (e.g. propargyl, ethynyl, butynyl and 1-hexynyl), $C_{3-6}$ cycloalkyl groups (e.g. cyclopropyl, cyclobutyl, cyclopentyl and cyclohexyl), $C_{6-14}$ aryl groups (e.g. phenyl, tolyl, xylyl, 1-naphthyl, 2-naphthyl, biphenyl, 2-indenyl and 2-anthryl, especially phenyl group), and $C_{7-16}$ aralkyl groups (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl and 5-phenylpentyl, especially benzyl group); $C_{1-4}$ alkyl groups (e.g. methyl) substituted with carbamoyloxy optionally substituted with $C_{1-4}$ alkyl (e.g. N,N-dimethylaminocarbonyloxy), $C_{2-5}$ alkanoyloxy (e.g. pivaloyloxy) or a 5- or 6-membered heterocyclic group (e.g. a 5-membered cyclic group containing, besides carbon atoms, 1 to 4 hetero-atoms selected from oxygen atom, sulfur atom and nitrogen atom, such as 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl and 1H- or 2H-tetrazolyl, a 6-membered cyclic group, preferably pyrrolidin-1-yl and morpholino, containing, besides carbon atoms, 1 to 4 hetero-atoms selected from oxygen atom, sulfur atom and nitrogen atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidinyl, pyranyl, thiopyranyl, 1,4-oxazinyl, 1,4-thiadinyl, 1,3-thiadinyl, piperazinyl, triazinyl, 3- or 4-pyridazinyl, pyrazinyl, N-oxido-3- or 4-pyridazinyl); $C_{2-8}$ alkoxycarbonyl (e.g. methoxycarbonyl, ethoxycarbonyl, propoxycarbonyl, butoxycarbonyl, pentyloxycarbonyl, n-hexyloxycarbonyl and n-octyloxycarbonyl); $C_{1-8}$ alkylaminocarbonyl (e.g. n-hexylaminocarbonyl and n-octylaminocarbonyl); $C_{2-8}$ alkoxycarbonyloxy (e.g. methoxycarbonyloxy, ethoxycarbonyloxy, propoxycarbonyloxy, butoxycarbonyloxy, pentyloxyoxycarbonyloxy, n-hexyloxycarbonyloxy and n-octyloxycarbonyloxy, preferably methoxycarbonyloxy); and 5- or 6-membered heterocyclic groups (e.g. a 5-membered cyclic group containing, besides carbon atoms, 1 to 4 hetero-atoms selected from oxygen atom, sulfur atom and nitrogen atom, such as 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl and 1H- or 2H-tetrazolyl, a 6-membered cyclic group, preferably e.g. tetrahydrofuran-2-yl, containing, besides carbon atoms, 1 to 4 hetero-atoms selected from oxygen atom, sulfur atom and nitrogen atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidinyl, pyranyl, thiopyranyl, 1,4-oxazinyl, 1,4-thiadinyl, 1,3-thiadinyl, piperazinyl, triazinyl, 3- or 4-pyridazinyl, pyrazinyl, N-oxido-3- or 4-pyridazinyl). And, in the case where two or more substituents of the amino, amidino or guanidino group exist, they may be combined to form a 5- or 6-membered heterocyclic group (e.g. pyrrolidine, piperidine, morpholine or imidazoline).

Preferable groups convertible into proton-accepting groups include groups which convert into proton-accepting groups in a living body and can accept physiologically active free proton. Examples of these groups include amidoxime groups optionally having substituents on oxygen atom (specific examples of the substituents include lower ($C_{1-4}$) alkyl (e.g. methyl, ethyl, propyl), acyl (e.g. $C_{2-5}$ alkanoyl (e.g. Pivotally) and benzoyl), lower ($C_{1-4}$) alkoxycarbonyl (e.g. methoxycarbonyl, ethoxycarbonyl, propoxycarbonyl), lower ($C_{1-4}$) alkylthiocarbonyl (e.g. methylthiocarbonyl, ethylthiocarbonyl), acyloxycarbonyl (e.g. $C_{2-5}$ alkanoyloxycarbonyl (e.g. pivaloyloxycarbonyl) and benzoyloxycarbonyl), optionally substituted $C_{6-12}$ aryloxycarbonyl (e.g. phenoxycarbonyl) or $C_{7-14}$ aralkyloxycarbonyl (e.g. benzyloxycarbonyl) (specific examples of the substituents include cyano, nitro, amino, lower ($C_{1-4}$) alkoxycarbonyl (e.g. methoxycarbonyl, ethoxycarbonyl, propoxycarbonyl), lower ($C_{1-4}$) alkyl (e.g. methyl, ethyl, propyl), lower ($C_{1-4}$) alkoxy (e.g. methoxy, ethoxy, propoxy), mono- and di- lower ($C_{1-4}$) alkylamino (e.g. methylamino, ethylamino, propylamino, dimethylamino), hydroxy, amido and lower ($C_{1-4}$) alkylthio (e.g. methylthio, ethylthio), optionally substituted $C_{6-12}$ aryl-carbonyl groups (e.g. phenylcarbonyl) (specific examples of the substituents include lower ($C_{1-4}$) alkyl (e.g. methyl, ethyl, propyl), lower ($C_{1-4}$) alkenyl (e.g. vinyl, allyl) or lower ($C_{1-4}$) alkynyl (e.g. ethynyl), or optionally substituted carbamoyl groups (specific examples of the substituents include cyano, nitro, amino, lower ($C_{1-4}$) alkoxy carbonyl (e.g. methoxycarbonyl, ethoxycarbonyl, propoxycarbonyl), lower ($C_{1-4}$) alkyl (e.g. methyl, ethyl, propyl), lower ($C_{1-4}$) alkoxy (e.g. methoxy, ethoxy, propoxy), mono- and di- lower ($C_{1-4}$) alkylamino (e.g. methylamino, ethylamino, propylamino, dimethylamino), hydroxy, amido and lower ($C_{1-4}$) alkylthio (e.g. methylthio, ethylthio), and optionally substituted oxadiazolyl or thiadiazolyl groups (examples of the substituents include oxo, thioxo, hydroxy, amino, mono- and di- lower ($C_{1-4}$) alkylamino (e.g. methylamino, ethylamino, propylamino, dimethylamino), halogen (e.g. fluoro, bromo, chloro), cyano, azido, lower ($C_{1-4}$) alkyl optionally substituted with halogen (e.g. trifluoromethyl), lower ($C_{1-4}$) alkoxy (e.g. methoxy, ethoxy, propoxy), lower ($C_{1-4}$) alkylthio (e.g. methylthio, ethylthio), lower ($C_{1-4}$) alkoxy carbonyl (e.g. methoxycarbonyl, ethoxycarbonyl, propoxycarbonyl), mono- or di- lower ($C_{1-4}$) alkylamino (e.g. methylamino, ethylamino, propylamino, dimethylamino), lower ($C_{1-4}$) alkylcarbamoyl (e.g. methylcarbamoyl, ethylcarbamoyl), $C_{6-12}$ aryl (e.g. phenyl) groups optionally having a substituent (specific examples the substituents include cyano, nitro, amino, lower ($C_{1-4}$) alkoxy carbonyl (e.g. methoxycarbonyl, ethoxycarbonyl, propoxycarbonyl), lower ($C_{1-4}$) alkyl (e.g. methyl, ethyl, propyl), lower ($C_{1-4}$) alkoxy (e.g. methoxy, ethoxy, propoxy), mono- and di- lower ($C_{1-4}$) alkylamino (e.g. methylamino, ethylamino, propylamino, dimethylamino), hydroxy, amido and lower ($C_{1-4}$) alkylthio (e.g. methylthio, ethylthio), or $C_{7-14}$ aralkyl groups (e.g. benzyl) optionally having a substituent (specific examples of the substituents include cyano, nitro, amino, lower ($C_{1-4}$) alkoxy carbonyl, lower ($C_{1-4}$) alkyl (e.g. methyl, ethyl, propyl), lower ($C_{1-4}$) alkoxy (e.g. methoxy, ethoxy, propoxy), mono- and di- lower ($C_{1-4}$) alkylamino (e.g. methylamino, ethylamino, propylamino, dimethylamino), hydroxy, amido or lower ($C_{1-4}$) alkylthio (e.g. methylthio, ethylthio)), and among the optionally substituted oxadiazolyl or thiazolyl groups, 1,2,4-oxadiazol-3-yl or 1,2,4-thiadiazol-3-yl groups optionally having a substituent respectively are preferable. And, in the case where the substituent is oxo or thioxo, the groups may take either keto- or enol-form.

Among the optionally substituted $C_{6-12}$ aryloxycarbonyl or $C_{7-14}$ aralkyloxycarbonyl groups, optionally substituted carbamoyl groups, optionally substituted $C_{6-12}$ aryl groups or optionally substituted $C_{7-14}$ aralkyl groups as the above substituent of the amidoxime, oxadiazolyl and thiadiazolyl group, are preferable those respectively substituted with cyano, nitro, lower ($C_{1-4}$) alkoxy-carbonyl or lower ($C_{1-4}$) alkoxy.

Among the optionally substituted $C_{6-12}$ aryl-carbonyl groups as the above substituent of the amidoxime group, are preferable those substituted with hydrogen atom or lower ($C_{1-4}$) alkyl.

More specific examples of the groups convertible into proton-accepting groups include 5-oxo-1,2,4-oxadiazol-3-yl group, 5-oxo-1,2,4-thiadiazol-3-yl group, 5-thioxo-1,2,4-oxadiazol-3-yl group, 5-thioxo-1,2,4-thiadiazol-3-yl group, 4-methyl-5-oxo-1,2,4-oxadiazol-3-yl group, 4-ethyl-5-oxo-1,2,4-oxadiazol-3-yl group, 4-propyl-5-oxo-1,2,4-oxadiazol-3-yl group, 1,2,4-oxadiazol-3-yl group, 5-ethoxycarbonyl-1,2,4-oxadiazol-3-yl group, 5-carbamoyl-1,2,4-oxadiazol-3-yl group, 5-cyano-1,2,4-oxadiazol-3-yl group, 5-trifluoromethyl-1,2,4-oxadiazol-3-yl group, 5-phenyl-1,2,4-oxadiazol-3-yl group, 5-amino-1,2,4-oxadiazol-3-yl group, 5-propylamino-1,2,4-oxadiazol-3-yl group, 5-methylthio-1,2,4-oxadiazol-3-yl group, 5-azido-1,2,4-oxadiazol-3-yl group, amino (hydroxy) imino group, amino (methoxycarbonyloxy) imino group, amino (ethoxycarbonyloxy) imino group, amino (n-propyloxycarbonyloxy) imino group, amino (benzyloxycarbonyloxy) imino group, amino (p-nitrobenzyloxycarbonyloxy) imino group, amino (p-nitrophenyloxycarbonyloxy) imino group, amino (p-nitrobenzoyloxycarbonyloxy) imino group, amino (methoxy) imino group, amino (carbamoyloxy) imino group, amino (methylcarbamoyloxy) imino group, amino (ethylcarbamoyloxy) imino group, amino (n-propylcarbamoyloxy) imino group and amino (n-butylcarbamoyloxy) imino group.

Among them, are preferable 5-oxo-1,2,4-oxadiazol-3-yl group, 5-oxo-1,2,4-thiadiazol-3-yl group, 5-ethoxycarbonyl-1,2,4-oxadiazol-3-yl group, 5-cyano-1,2,4-oxadiazol-3-yl group, 5-trifluoromethyl-1,2,4-oxadiazol-3-yl group, amino (methoxycarbonyloxy) imino group, amino (carbonyloxy) imino group, amino (methylcarbamoyloxy) imino group and amino (ethylcarbamoyloxy) imino group.

Preferable example of $A^1$ and $A^2$ include (1) amidino and guanidino groups which may be substituted with $C_{2-8}$ alkoxycarbonyloxy, and (2) amino groups which may be substituted with oxadiazolyl group which may be substituted with oxo or $C_{1-4}$ alkyl which may be substituted with halogen, and are unsubstituted amino, amidino or guanidino groups are more preferable.

And, the compound (I), wherein $A^1$ or $A^2$ are a group convertible into a proton-accepting group, or a salt thereof can be advantageously used as an orally administrable preparation.

In the above formula (I), D is a spacer having a 2- to 6-atomic chain optionally bonded through a hetero-atom and/or a 5- or 6-membered ring (provided that the 5- or 6-membered ring is, depending on its bonding position, counted as 2- or 3-atomic chain).

The spacer of D means a linear interval between $A^1$ and

and means having a interval which is lined with 2 to 6 atoms between them in the present invention.

In the above formula (I), examples of hetero-atoms in the spacer having a 2- to 6-atomic chain (2- to 6-membered chain) optionally bonded through a hetero-atom and/or a 5- or 6-membered ring include N, O and S. And, the 5- or 6-membered ring may be carbocyclic one or a heterocyclic one containing 1 to 4 hetero-atoms selected from N, O and S or a saturated ring or an unsaturated ring such as aromatic ring. Examples of such 5- or 6-membered ring include the following;

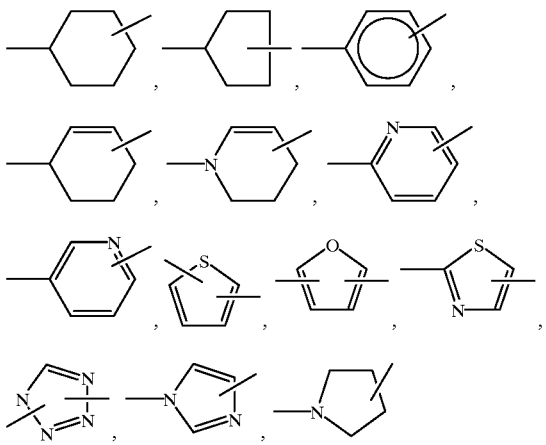

And, the above-mentioned 5- or 6-membered ring is preferably such one as having no bond at the adjacent position on the ring. The above-mentioned 5- or 6-membered ring is preferably such one as having a bond at the second or third position to one another on the ring. Usually, even the ring is saturated or unsaturated, it is regarded as 2- to 3-atomic chain (2- to 3-membered chain), and a group having a 2- to 6-atomic chain as D itself is preferable. As the hetero-atom existing in the spacer shown by D, nitrogen is preferable above all, and, D bonded to a group shown by $A^1$, such as amidino group existing through —NH— group, is especially preferable. And, the above-mentioned 5- or 6-membered ring may be bonded to the adjacent amidino group directly or to a group shown by $A^1$ such as amidino group through —NH— group, and further to a group shown by $A^1$ such as amidino group through methylene chain.

And, D may be such one as the adjacent carbonyl group is bonded directly to the above-mentioned 5- or 6-membered ring, or bonded through methylene chain or bonded through a hetero atom. The methylene chain in D may be substituted with a group of the formula

wherein $R^3$ is a hydrogen atom or a lower ($C_{1-4}$) alkyl group optionally substituted with an optionally substituted phenyl group; and $R^4$ is a lower ($C_{1-4}$) alkyl group optionally substituted with an optionally substituted phenyl group, an optionally substituted phenyl group or benzyloxy group.

Examples of substituents of the optionally substituted phenyl group as the substituent to the lower ($C_{1-4}$) alkyl group of $R^3$ or $R^4$ include lower ($C_{1-4}$) alkyl (e.g. methyl, ethyl), lower ($C_{1-4}$) alkoxy (e.g. methoxy, ethoxy), halogen (e.g. fluoro, chloro, bromo), and hydroxyl group.

Example of the lower ($C_{1-4}$) alkyl group of $R^3$ or $R^4$ include methyl and ethyl.

Preferable typical groups shown by D include those of the formula

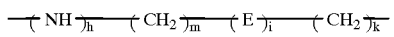

wherein h and i each is 0 or 1; m and k each is 0, 1 or 2; and E is the above-mentioned 5- or 6-membered ring, especially cyclohexane ring, benzene ring, piperidine or a group of the formula

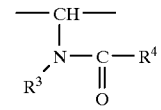

As E, 5- or 6-membered ring is especially preferable. And, as h, 0 or 1, as m, 0, 1 or 2, and as k, 0 are respectively preferable. Among 5- or 6-membered rings shown by E, benzene ring and cyclohexane ring are preferable, and benzene ring is especially preferable.

In the above-mentioned formula (I), groups of the formula

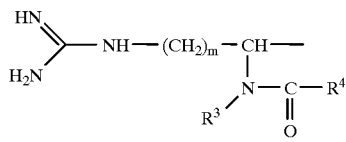

wherein $R^3$, $R^4$ and m are of the same meaning as defined above, are substituted groups derived from arginine or homoarginine.

As D, groups of the formula

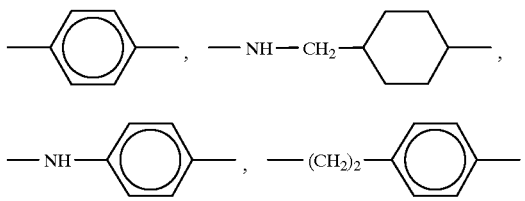

(among others, above all

and

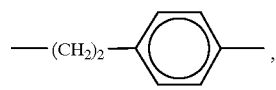

especially

)

are especially preferable.
(in these groups, either of the bonds may be bonded to $A^1$)

In the above formula (I), $R^1$ is a hydrogen atom or a hydrocarbon group.

As the hydrocarbon shown by $R^1$, mention is made of chain-like or cyclic hydrocarbon groups including $C_{1-6}$ alkyl groups (e.g. methyl, ethyl, propyl, isopropyl, butyl, sec-butyl, tert-butyl, pentyl and hexyl), $C_{2-6}$ alkenyl groups (e.g. vinyl, allyl, isopropenyl, butenyl, isobutenyl and sec-butenyl), $C_{2-6}$ alkynyl groups (e.g. propargyl, ethynyl, butynyl and, 1-hexynyl), $C_{3-6}$ cycloalkyl groups (e.g. cyclopropyl, cyclobutyl, cyclopentyl and cyclohexyl), $C_{6-14}$ aryl groups (e.g. phenyl, tolyl, xylyl, 1-naphthyl, 2-naphthyl, biphenyl, 2-indenyl and 2-anthryl, especially phenyl group), and $C_{7-16}$ aralkyl groups (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl and 5-phenylpentyl, especially benzyl group), and as $R^1$, are preferable hydrogen, lower ($C_{1-4}$) alkyl or benzyl (especially hydrogen).

In the above formula (I), $R^2$ is a hydrogen atom or a residual group formed by removing —CH(NH$_2$)COOH from an α-amino acid.

As the group shown by $R^2$, any of the residual groups formed by removing —CH(NH$_2$)COOH from an α-amino acid can be mentioned. And, $R^1$ and $R^2$ may be combined to form a 5- or 6-membered ring. Preferable examples of such 5- or 6-membered ring include rings as shown below,

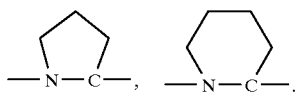

Usually, preferable examples of $R^2$ include residual groups of essential amino acids. Especially preferable examples of $R^2$ include a hydrogen atom, lower ($C_{1-4}$) alkyl groups, lower ($C_{1-4}$) alkyl groups substituted with an optionally substituted phenyl group, lower ($C_{1-4}$) alkyl groups substituted with hydroxyl group and lower ($C_{1-4}$) alkyl groups substituted with carbamoyl group. More specifically, hydrogen, methyl, isopropyl, sec-butyl, isobutyl, hydroxylmethyl, benzyl, p-hydroxybenzyl, p-methoxybenzyl, carbamoylmethyl and carbamoylethyl are mentioned as typical examples.

As substituents optionally substituted on the benzene ring of optionally substituted phenyl group as the substitutent of the lower ($C_{1-4}$) alkyl of the above $R^2$, mention is made of, for example, lower ($C_{1-4}$) alkyl groups (e.g. methyl, ethyl, propyl, isopropyl, n-butyl and sec-butyl), lower ($C_{1-4}$) alkoxy groups (e.g. methoxy and ethoxy), halogen (e.g. chlorine, fluorine and bromine) and hydroxyl group, and the lower ($C_{1-4}$) alkoxy group is preferable.

As the group or atom shown by $R^2$, hydrogen atom or $C_{1-4}$ alkyl group substituted with phenyl group optionally substituted with $C_{1-4}$ alkoxy are preferable, p-hydroxybenzyl, p-methoxybenzyl or hydrogen atom (more preferably p-methoxybenzyl or hydrogen atoms especially hydrogen atom) are more preferable.

In the above-mentioned formula (I), n is an integer of 0 to 8 (preferably 1 to 4 especially 2 or 3).

In the above formula (I), P is a spacer having a 1- to 10-atomic chain optionally bonded through a hetero-atom and/or a 5- or 6-membered ring (provided that the 5- or 6-membered ring is, depending on its bonding position, counted as 2- or 3-atomic chain). The spacer of P means a linear interval between $(CH_2)_n$ and $A^2$, and means having a interval which is lined with 1 to 10 atoms between them in the present invention. As the spacer having 1- to 10-atomic chains (1- to 10-membered chain) optionally bonded through hetero-atoms and/or a 5- or 6-membered ring, mention is made of a divalent hydrocarbon group optionally bonded through 1 to 4 (preferable 1 or 2) groups selected from

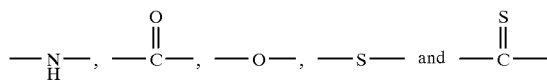

and/or a 5- or 6-membered ring (the 5- or 6-membered ring may be a carbocyclic one or a heterocyclic one containing 1 to 4 hetero-atoms selected from N, O and S, which may be saturated ring or unsaturated one such as aromatic ring; as the carbocyclic one, for example,

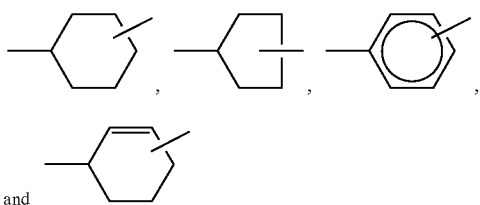

and are mentioned, and benzene ring and cyclohexane ring are preferable, and especially benzene ring is preferable; as the heterocyclic ring, a 5-membered cyclic group containing, besides carbon atoms, 1 to 4 hetero-atoms selected from, for example, oxygen atom, sulfur atom and nitrogen atom, as exemplified by 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl, and 1H- or 2H-tetrazolyl, and, a 6-membered cyclic group containing, besides carbon atoms, 1 to 4 hetero-atoms selected from oxygen atom, sulfur atom and nitrogen atom, as exemplified by 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidinyl, pyranyl, thiopyranyl, 1,4-oxazinyl, 1,4-thiazinyl, 1,3-thiazinyl, piperazinyl, triazinyl, 2- or 4-pyridazinyl, pyrazinyl, and N-oxido-3- or 4-pyridazinyl, and piperazine or piperidine is preferable).

As more preferable spacer having 1- to 10-atomic chains optionally bonded through hetero-atoms and/or a 5- or 6-membered ring, mention is made of a divalent hydrocarbon group optionally bonded through 1 to 4 (preferably 1 or 2) groups selected from

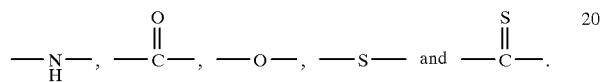

And, in the above-mentioned formula (I), P is groups represented by, for example, the formula,

wherein Z is a one selected from

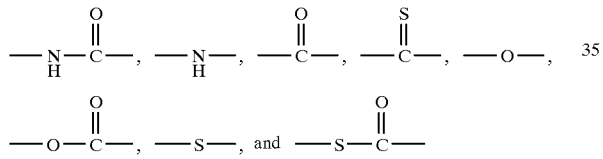

(either bond may be bonded to B) or a bond, and B is a group

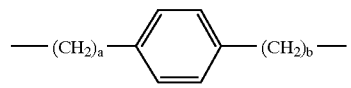

or

(a and b are an integer of 0 to 2 (preferably 0 or 1), and c is an integer of 1 to 5) or a bond (excepting the case where Z and B are both bonds).

Among the groups shown by the above Z, those represented by

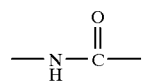

(either of the bonds may be bonded to B) are preferable.

Among the groups shown by the above B, those represented by

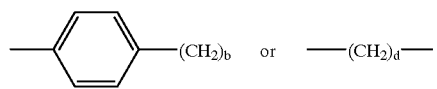

wherein b is an integer of 0 to 2 (preferably 0 or 1), and d is an integer of 1 to 4, are preferable. Further preferable groups shown by the above B include

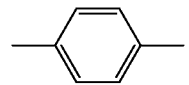

or —$(CH_2)_d$— wherein d is an integer or 1 to 4.

Preferable examples of the optionally amidated carboxyl group shown by Y include groups represented by the formula

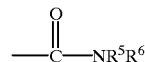

wherein $R^5$ and $R^6$ independently are hydrogen, a lower ($C_{1-6}$) alkyl group (e.g. methyl, ethyl, propyl, butyl and hexyl), a $C_{2-8}$ alkenyl group (e.g. allyl, 2-butenyl and 3-pentenyl), a lower ($C_{1-4}$) alkyl group (e.g. pyridylmethyl) substituted with a 5- or 6-membered heterocyclic group (e.g. a 5-membered cyclic group containing, besides carbon atoms, 1 to 4 hetero-atoms selected from, for example, oxygen atom, sulfur atom and nitrogen atom, as exemplified by 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl, 1H- or 2H-tetrazolyl, and, a 6-membered cyclic group containing, besides carbon atoms, 1 to 4 hetero-atoms selected from oxygen atom, sulfur atom and nitrogen atom, as exemplified by 2-, 3- or 4-pyridyl, N-oxido-2-, 3- or 4-pyridyl, 2-, 4- or 5-pyrimidinyl, N-oxido-3-, 4- or 5-pyrimidinyl, thiomorpholinyl, morpholinyl, piperidinyl, pyranyl, thiopyranyl, 1,4-oxazinyl, 1,4-thiazinyl, 1,3-thiazinyl, piperazinyl, triazinyl, 2- or 4-pyridazinyl, pyrazinyl, and N-oxido-3- or 4-pyridazinyl, preferably pyridyl) or a $C_{6-2}$ aralkyl group (e.g. benzyl, phenethyl and phenyl propyl), and, the aryl groups in the aralkyl group may be unsubstituted or optionally substituted with one or two substituents as exemplified by nitro, halogen (chlorine, fluorine and bromine), lower ($C_{1-4}$) alkyl groups (e.g. methyl and ethyl) and lower ($C_{1-4}$) alkoxy groups (e.g. methoxy, ethoxy and propoxy).

Preferable examples of optionally esterified carboxyl groups shown by Y include groups of the formula

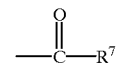

wherein $R^7$ is 1) hydroxyl group, 2) an optionally substituted alkoxy, alkenyloxy or benzyloxy group (e.g. lower ($C_{1-8}$) alkoxy (e.g. methoxy, ethoxy, propoxy), lower ($C_{2-12}$) alkenyloxy (e.g. vinyloxy, allyloxy) or benzyloxy group which may be substituted with hydroxyl group, optionally substituted amino (e.g.

amino, N-lower ($C_{1-4}$) alkylamino (e.g. methylamino), N,N-di-lower ($C_{6-14}$) alkylamino (e.g. dimethylamino), piperidino and morpholino), halogen (e.g. chloro, fluoro, bromo), lower ($C_{1-6}$) alkoxy (e.g. methoxy, ethoxy), lower ($C_{1-6}$) alkylthio (e.g. methylthio, ethylthio), lower ($C_{1-4}$) alkoxy-carbonyl (e.g. methoxycarbonyl, ethoxycarbonyl, propoxycarbonyl, isobutyloxycarbonyl), or optionally substituted dioxolenyl (e.g. 5-methyl-2-oxo-1,3-dioxolen-4-yl)) or 3) a group of the formula —OCH($R^{7a}$)OCOR$^8$ in which $R^{7a}$ is hydrogen, a straight-chain or branched lower ($C_{1-6}$) alkyl group (e.g. methyl, ethyl, n-propyl, isopropyl, n-butyl, isobutyl, sec-butyl, t-butyl, n-pentyl, isopentyl and neopentyl), or a $C_{5-7}$ cycloalkyl group (e.g. cyclopentyl, cyclohexyl and cycloheptyl), and $R^8$ is i) a straight-chain or branched lower ($C_{1-6}$) alkyl group (e.g. methyl, ethyl, n-propyl, isopropyl, n-butyl, isobutyl, sec-butyl, t-butyl, n-pentyl, isopentyl and neopentyl), ii) a lower ($C_{2-8}$) alkenyl group (e.g. vinyl, propenyl, allyl and isopropenyl), iii) a $C_{5-7}$ cycloalkyl group (e.g. cyclopentyl, cyclohexyl and cyclobutyl), iv) a lower ($C_{1-3}$) alkyl group substituted with $C_{5-7}$ cycloalkyl (e.g. cyclopentyl, cyclohexyl and cycloheptyl) or optionally substituted $C_{6-12}$ aryl such as phenyl (e.g. benzyl, p-chlorobenzyl, phenethyl, cyclopentylmethyl and cyclohexylmethyl), v) a lower ($C_{2-3}$) alkenyl group substituted with $C_{5-7}$ cycloalkyl (e.g. cyclopentyl, cyclohexyl and cycloheptyl) or optionally substituted $C_{6-12}$ aryl such as phenyl (e.g. cinnamyl having alkenyl moiety such as vinyl, propenyl, allyl or isopropenyl), vi) an optionally substituted aryl groups such as optionally substituted phenyl group (e.g. phenyl, p-tolyl and naphthyl), vii) a straight-chain or branched lower ($C_{1-6}$) alkoxy group (e.g. methoxy, ethoxy, n-propoxy, isopropoxy, n-butoxy, isobutoxy, sec-butoxy, t-butoxy, n-pentyloxy, isopentyloxy and neopentyloxy), viii) a straight-chain or branched lower ($C_{1-6}$) alkenyloxy group (e.g. allyloxy and isobutenyloxy), ix) a $C_{5-7}$ cycloalkyloxy group (e.g. cyclopentyloxy, cyclohexyloxy and cycloheptyloxy), x) a lower ($C_{1-3}$) alkoxy group substituted with $C_{5-7}$ cycloalkyl groups (e.g. cyclopentyl, cyclohexyl and cycloheptyl) or optionally substituted $C_{6-12}$ aryl such as phenyl (e.g. benzyloxy, phenethyloxy, cyclopentylmethyloxy and cyclohexylmethyloxy, having alkoxy moiety such as methoxy, ethoxy, n-propoxy or isopropoxy), xi) a lower ($C_{2-3}$) alkenyloxy group substituted with $C_{5-7}$ cycloalkyl groups (e.g. cyclopentyl, cyclohexyl and cycloheptyl) or optionally substituted $C_{6-12}$ aryl such as phenyl (e.g. cinnamyloxy having alkenyloxy moiety such as vinyloxy, propenyloxy, allyloxy or isopropenyloxy), xii) an optionally substituted $C_{6-12}$ aryloxy group such as an optionally substituted phenoxy group (e.g. phenoxy, p-nitrophenoxy and naphthoxy).

In the above formula, when the substituent $R^8$ includes an optionally substituted $C_{6-2}$ aryl group, the $C_{6-12}$ aryl group is exemplified by phenyl and naphthyl (preferably phenyl), and, as the substituents of the $C_{6-12}$ aryl group, mention is made of, for example, nitro, halogen (e.g. chlorine, fluorine and bromine), lower ($C_{1-4}$) alkyl (e.g. methyl, ethyl, propyl) and lower ($C_{1-4}$) alkoxy (e.g. methoxy, ethoxy, propoxy), and, among them, unsubstituted phenyl is preferably used.

Preferable examples of Y are a carboxyl group and a lower ($C_{1-4}$) alkoxy-carbonyl group (e.g. carboxyl, ethoxycarbonyl), and a carboxyl group is more preferable.

Among the compounds represented by the abovementioned formula (I) or their salts, the compounds (Ia) of the formula

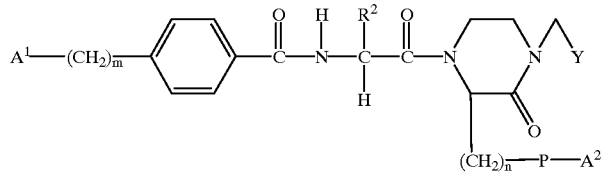

(Ia)

wherein $A^1$ and $A^2$ independently are an optionally substituted amino, amidino or guanidino group, an amidoxime group optionally having a substituent on the oxygen atom, or an optionally substituted oxadiazolyl or thiadiazolyl group, $R^2$ is hydrogen, a lower ($C_{1-4}$) alkyl group, a lower ($C_{1-4}$) alkyl group substituted with an optionally substituted phenyl group, a lower ($C_{1-4}$) alkyl group substituted with hydroxyl group or a lower ($C_{1-4}$) alkyl group substituted with carbamoyl group, P is a divalent hydrocarbon optionally bonded through 1 to 4 groups selected from

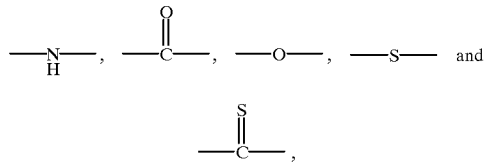

Y is an optionally esterified or amidated carboxyl group, m is an integer of 0 to 2, and n is an integer of 0 to 8, and their salts are preferable.

More preferable examples of the above-mentioned compounds (Ia) and their salts include compounds (Ia) wherein $A^1$ and $A^2$ independently are an unsubstituted amino, amidino or guanidino group, or an optionally substituted 1,2,4-oxadiazol-3-yl or 1,2,4-thiadiazol-3-yl group, $R^2$ is p-hydroxybenzyl, p-methoxybenzyl or hydrogen atom, P is a group of the formula, —Z—B— in which Z is a group selected from

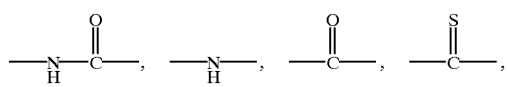

-continued

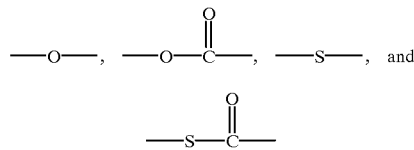

(either of the bonds of them may bonded to B) or a bond, and

B is

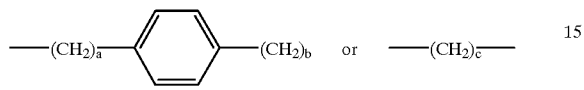

(a and b each is an integer of 0 to 2 (preferably 0 or 1), and c is an integer of 1 to 5) or a bond (excepting the case where Z and B both are a bond)], Y is an optionally esterified or amidated carboxyl group, m is an integer of 0 to 2, and n is an integer of 1 to 4, and their salts.

Furthermore preferable examples of the above-mentioned compounds (Ia) and their salts include compounds (Ia) wherein $A^1$ and $A^2$ independently are unsubstituted amino, amidino or guanidino group, or an optionally substituted 1,2,4-oxadiazol-3-yl or 1,2,4-thiadiazol-3-yl group, $R^2$ is p-hydroxybenzyl, p-methoxybenzyl or hydrogen atom, P is a group of the formula —Z—B— in which Z is

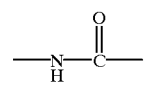

B is a group of the formula

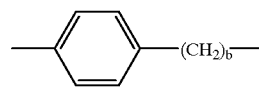

(b is an integer of 0 to 2 (preferably 0 or 1))], Y is an optionally esterified or amidated carboxyl group, m is an integer of 0 to 2, and n is an integer of 1 to 4, or their salts.

Preferable examples of the compound (I) and their salts include compounds (I) wherein $A^1$ and $A^2$ independently are (1) an amidino or guanidino group optionally substituted with $C_{2-8}$ alkoxycarbonyloxy, (2) an amino group optionally substituted with oxadiazolyl optionally substituted with oxo or $C_{1-4}$ alkyl optionally substituted with halogen, or (3) an oxadiazolyl group optionally substituted with oxo or $C_{1-4}$ alkyl optionally substituted with halogen, D is a group of the formula:

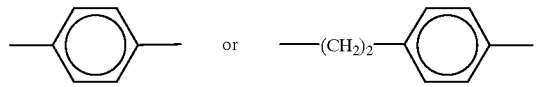

$R^1$ is a hydrogen atom, $R^2$ is a hydrogen atom or a $C_{1-4}$ alkyl group substituted with phenyl optionally substituted with $C_{1-4}$ alkoxy, P is a group of the formula: —Z—B— wherein Z is

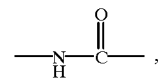

a bond or

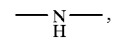

and B is

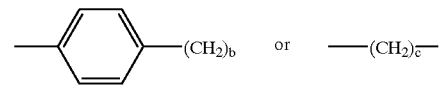

in which b is 0 or 1, and c is an integer of 1 to 5,

Y is a group of the formula:

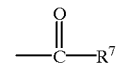

wherein $R^7$ is 1) hydroxy group, 2) a $C_{1-8}$ alkoxy or $C_{2-1}$. alkenyloxy group which may be substituted with $C_{1-4}$ alkoxy-carbonyl or 5-methyl-2-oxo-1,3-dioxolen-4-yl, or 3) a group of the formula: —OCH($R^{7a}$)OCOR$^8$ in which $R^{7a}$ is a hydrogen atom or a $C_{1-6}$ alkyl group, and $R^8$ is a $C_{1-6}$ alkyl group or a $C_{5-7}$ cycloalkyloxy group, and n is an integer of 1 to 4.

More preferable examples of the compound (I) and their salts include compounds (I) wherein $A^1$ and $A^2$ are independently (1) an amidino or guanidino group optionally substituted with methoxycarbonyloxy or (2) an amino group optionally substituted with 5-oxo-1, 2,4-oxodiazol-3-yl or 5-trifluoromethyl-1,2,4-oxadiazol-3-yl, D is

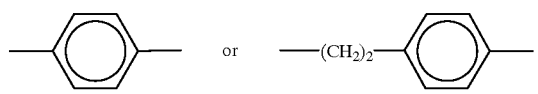

$R^1$ is a hydrogen atom, $R^2$ is a hydrogen atom or p-methoxybenzyl,

P is

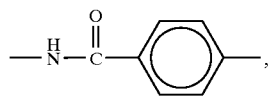

Y is a carboxyl group and
n is 2 or 3.

In the case where the compound of this invention is used as an orally administrable agent, desirable examples of optionally esterified carboxyl groups shown by Y include methoxycarbonyl, ethoxycarbonyl, tert-butoxycarbonyl, propoxycarbonyl, pivaloyloxymethoxycarbonyl, 1-(cyclohexylcarbonyloxy)ethoxycarbonyl, 5-methyl-2-oxo-1,3-dioxolen-4-ylmethoxycarbonyl, acetoxymethyloxycarbonyl, propionyloxymethoxycarbonyl, n-butyloxymethoxycarbonyl, isobutyloxymethoxycarbonyl, 1-(ethoxycarbonyloxy)ethoxycarbonyl, 1-(acetyloxy)ethoxycarbonyl, 1-(isobutyloxy)ethoxycarbonyl, 2-(isobutyloxycarbonyl)-2-propylidenethoxycarbonyl and (3-phthalidylidene)ethoxycarbonyl.

The compounds of this invention have one or more asymmetric carbons in the molecule, and both R-configurated ones and S-configurated ones relative to these asymmetric carbons are included in the present invention.

Examples of the salts of the compounds (I) and (Ia) of this invention include pharmaceutically acceptable salt such as inorganic acid salts such as hydrochloride, hydrobromide, sulfate, nitrate and phosphate, organic acid salts such as acetate, tartrate, citrate, fumarate, maleate, toluenesulfonate and methanesulfonate, metal salts such as sodium salt, potassium salt, calcium salt and aluminum salt, and salts with a base such as triethylamine salt, guanidine salt, ammonium salt, hydrazine salt, quinine salt and cinchonine salt.

Specific examples of preferable compounds include 4-(4-amidinobenzoyl)aminoacetyl-3-[3-(4-amidinobenzoyl)aminopropyl]-2-oxopyperazine-1-acetic acid, 4-(4-amidinobenzoyl)aminoacetyl-3-[4-(4-amidinobenzoyl)aminobutyl]-2-oxopiperazine-1-acetic acid, 4-(4-amidinobenzoyl)aminoacetyl-3-[2-(4-amidinobenzoyl)aminoethyl]-2-oxopiperazine-1-acetic acid, 4-(4-amidinobenzoyl)aminoacetyl-3-[2-(4-amidinophenylaminocarbonyl)ethyl]-2-oxopiperazine-1-acetic acid, 4-(4-amidinobenzoyl)aminoacetyl-3-[3-(4-amidinophenylaminocarbonyl)propyl]-2-oxopiperazine-1-acetic acid, 4-(4-amidinobenzoyl)aminoacetyl-3-[4-(4-amidinophenylaminocarbonyl)butyl]-2-oxopiperazine-1-acetic acid, 4-(4-guanidinobenzoyl)aminoacetyl-3-[2-(4-guanidinobenzoylamino)ethyl)-2-oxopiperazine-1-acetic acid, 4-(4-guanidinobenzoyl)aminoacetyl-3-[3-(4-guanidinobenzoylamino)propyl]-2-oxopiperazine-1-acetic acid, 4-(4-guanidinobenzoyl)aminoacetyl-3-[4-(4-guanidinobenzoylamino)butyl]-2-oxopiperazine-1-acetic acid, 4-(4-amidinobenzoylamino)acetyl-3-[2-(4-guanidinobenzoylamino)ethyl]-2-oxopiperazine-1-aceticacid, 4-(4-amidinobenzoylamino)acetyl-3-[3-(4-guanidinobenzoylamino)propyl]-2-oxopiperazine-1-acetic acid, 4-(4-amidinobenzoylamino)acetyl-3-[4-(4-guanidinobenzoylamino)butyl]-2-oxopiperazine-1-acetic acid, 4-[4-(2-aminoethyl)benzoylamino]acetyl-3-(2-(4-amidinobenzoylamino)ethyl]-2-oxopiperazine-1-acetic acid, 4-[4-(2-aminoethyl)benzoylamino]-3-[3-(4-amidinobenzoylamino)propyl]-2-oxopiperazine-1-acetic acid, and 4-[4-(2-aminoethyl)benzoylamino]acetyl-3-[4-(4-amidinobenzoylamino)butyl]-2-oxopiperazine-1-acetic acid, (S,S)-[3-[3-(4-guanidinobenzoylamino)propyl]-4-[3-(4-methoxyphenyl)-2-[4-(5-trifluoromethyl-[1,2,4]oxadiazol-3-ylamino)benzoylaminojpropionyl]-2-oxopiperazin-1-yl]acetic acid, (S,S)-[4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoyl-amino]propyl]piperazin-1-yl]acetic acid, (S,S)-[4-[3-(4-methoxyphenyl)-2-[4-(5-oxo-4,5-dihydro[1,2,4]oxadiazol-3-ylamino)benzoylamino]propionyl]-2-oxo-3-[4-(5-oxo-4,5-dihydro[1,2,4]oxadiazol-3-ylamino)benzoylamino]-propyl]piperazin-1-yl]acetic acid or (S,S)-4-[2-(4-guanidinobenzoyl)amino-3-(4-methoxyphenyl)propionyl]-3-[3-(4-guanidinobenzoyl)aminopropyl]-2-oxopiperazine-1-acetic acid, or a salt thereof, more preferably, (S)-4-(4-amidinobenzoyl)aminoacetyl-3-{3-(4-amidinobenzoyl)amino}propyl-2-oxopiperazine-1-acetic acid, (S)-4-(4-guanidinobenzoylamino)acetyl-3-[3-(4-guanidinobenzoylamino)]propyl-2-oxopiperazine-1-acetic acid, (S)-4-(4-amidinobenzoylamino)acetyl-3-[2-(4-guanidinobenzoylamino)]ethyl-2-oxopiperazine-1-acetic acid, (S)-4-[4-(2-aminoethyl)benzoylamino]acetyl-3-[3-(4-amidinobenzoylamino)]propyl-2-oxopiperazine-1-acetic acid, (S,S)-[3-[3-(4-guanidinobenzoylamino)propyl]-4-[3-(4-methoxyphenyl)-2-[4-(5-trifluoromethyl-[1,2,4]oxadiazol-3-ylamino)benzoylamino]propionyl]-2-oxopiperazin-1-yl]acetic acid, (S,S)-[4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoyl-amino]propyl]piperazin-1-yl]acetic acid, (S,S)-[4-[3-(4-methoxyphenyl)-2-[4-(5-oxo-4,5-dihydro[1,2,4]oxadiazol-3-ylamino)benzoylamino]propionyl]-2-oxo-3-[4-(5-oxo-4,5-dihydro[1,2,4]oxadiazol-3-ylamino)benzoylamino]-propyl]piperazin-1-yl]acetic acid or (S,S)-4-[2-(4-guanidinobenzoyl)amino-3-(4-methoxyphenyl)propionyl]-3-[3-(4-guanidinobenzoyl)aminopropyl]-2-oxopiperazine-1-acetic acid, or a salt thereof, further more preferably, (S)-4-(4-amidinobenzoyl)aminoacetyl-3-{3-(4-amidinobenzoyl)amino}propyl-2-oxopiperazine-1-acetic acid, (S)-4-(4-guanidinobenzoylamino)acetyl-3-[3-(4-guanidinobenzoylamino)]propyl-2-oxopiperazine-1-acetic acid, (S)-4-(4-amidinobenzoylamino)acetyl-3-[2-(4-guanidinobenzoylamino)]ethyl-2-oxopiperazine-1-acetic acid or (S)-4-[4-(2-aminoethyl)benzoylamino]acetyl-3-[3-(4-amidinobenzoylamino)]propyl-2-oxopiperazine-1-acetic acid trifluoroacetate, or a salt thereof.

The most preferable example is (S)-4-(4-guanidinobenzoylamino)acetyl-3-[3-(4-guanidinobenzoylamino)]propyl-2-oxopiperazine-1-acetic acid or a salt thereof (a pharmaceutically acceptable salt thereof), more preferably (S)-4-(4-guanidinobenzoylamino)acetyl-3-[3-(4-guanidinobenzoylamino)]propyl-2-oxopiperazine-1-acetic acid or a pharmaceutically acceptable acid addition salt thereof, especially preferably (S)-4-(4-guanidinobenzoylamino)acetyl-3-[3-(4-guanidinobenzoylamino)]propyl-2-oxopiperazine-1-acetic acid hydrochloride.

And, another preferable example is 4-(4-guanidinobenzoylamino)acetyl-3-[3-(4-guanidinobenzoylamino)]propyl-2-oxopiperazine-1-acetic acid or a salt thereof.

The compounds (I) and (Ia) of this invention can be produced by, for example, methods as described below, namely, by reacting a compound (II) of the formula

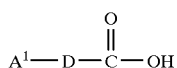

(II)

wherein each symbol is of the same meaning as defined above or, a reactive derivative thereof, or a salt thereof, with a compound (III) of the formula

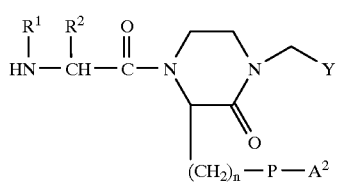

(III)

wherein each symbol is of the same meaning as defined above, or a salt thereof.

Examples of the salt of the compound (II) or (III) include inorganic acid salts such as hydrochloride, hydrobromide, sulfate, nitrate and phosphate, organic acid salts such as acetate, tartrate, citrate, fumarate, maleate, toluenesulfonate and methanesulfonate, metal salts such as sodium salt, potassium salt, calcium salt and aluminum salt, and salts with a base such as triethylamine salt, guanidine salt, ammonium salt, hydrazine salt, quinine salt and cinchonine salt, which are pharmaceutically acceptable ones.

Examples of the reactive derivative of the compound (II) include compounds (II) of the formula

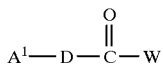

wherein $A^1$ is of the same meaning as defined above, and W is halogen (preferably chlorine) or corresponding acid halides, azides, active esters (esters with alcohol such as pentachlorophenol, 2,4,5-trichlorophenol, 2,4-dinitrophenol, cyanomethylalcohol, paranitrophenol, N-hydroxy-5-norbornene-2,3-dicarboxyimide, N-hydroxysuccinimide, N-hydroxyphthalimide, and N-hydroxybenztriazole).

The condensation reaction as the methods for producing the compounds (I) and (Ia) of this invention can be carried out by an amide-linkage formation reaction in a conventional peptide synthesis, for example, the method using active ester, mixed acid anhydride or acid chloride.

For example, the condensation reaction between the compound (II) and the compound (III) can be conducted by subjecting the compound (II) to condensation with a phenol such as 2,4,5-trichlorophenol, pentachlorophenol, 2-nitrophenol or 4-nitrophenol or an N-hydroxy compound such as N-succinimide, N-hydroxy-5-norbornen-endo-2,3-dicarboxyimide, 1-hydroxybenztriazole or N-hydroxypiperidine in the presence of a reagent such as dicyclohexylcarbodiimide to convert into an active ester thereof, followed by condensation. Alternatively, the compound (II) is allowed to react with isobutyl chloroformate to give a mixed acid anhydride, which is then subjected to condensation.

The condensation between the compound (II) or a reactive derivative thereof and the compound (III) can also be performed by using singly a peptide-formation reagent such as dicyclohexylcarbodiimide, N,N'-carbonyldiimidazole, diphenylphosphoryl azide or diethyl cyanophosphate.

In said condensation reaction, the amidino group, guanidino group or amino group present in the compound (II), a reactive derivative thereof or the compound (III) are preferably present as the salt of an inorganic acid (e.g. hydrogen chloride, sulfuric acid, nitric acid or hydrobromic acid) or protected with tert-butoxycarbonyl group or benzyloxycarbonyl group.

And, in said condensation reaction, the carboxyl group present in the compound (II), a reactive derivative thereof or the compound (III) is desirably present as the salt of an inorganic acid (e.g. hydrogen chloride, sulfuric acid, nitric acid or. hydrobromic acid) or protected with methyl, ethyl, benzyl or tert-butyl group.

And, in said condensation reaction, the hydroxyl group present in the compound (II) a reactive derivative thereof or the compound (III) is desirably present as the salt of an inorganic acid (e.g. hydrogen chloride, sulfuric acid, nitric acid or hydrobromic acid) or protected with benzyl or tert-butyl group.

Any of the above-mentioned condensation reactions can be promoted by the addition of preferably an organic base (e.g. triethylamine, N-methylpiperidine, 4-N,N-dimethylaminopyridine) or an inorganic base (sodium hydrogencarbonate, sodium carbonate, potassium carbonate). The reaction temperature ranges usually from −20 to +50° C., preferably from 0° C. to about +30° C. The reaction time varies depending on kinds of the solvents (including mixing ratio in the case of a mixed solvent) and reaction temperature, which ranges usually from one minute to 72 hours, preferably from about 15 minutes to 5 hours. Examples of solvents usually employed include water, dioxane, tetrahydrofuran, acetonitrile, pyridine, N,N-dimethylformamide, dimethyl sulfoxide, N-methylpyrrolidone, chloroform and methylene chloride, and these can be used singly or as a mixture.

The protective group of the carboxyl group contained in the product of the final method (benzyl group or tert-butyl group, which is the protective group of the carboxyl group of Y in the general formula (I)) can be removed by a per se known method. For example, a compound having a benzyl ester group can be converted to a carboxylic acid derivative by subjecting the compound to hydrogenation in the presence of a precious metal catalyst such as palladium or platinum, and a compound having a tert-butyl ester group can be converted to a carboxylic acid derivative by processing the compound with an acid such as trifluoroacetic acid or hydrogen chloride.

The protective group of the amino group contained in the product in the final method (tert-butoxycarbonyl group or benzyloxycarbonyl group, which is the protective group of the amino group of X' in the below reaction schema) can be removed by a Der se known method. For example, the tert-butoxycarbonyl group can be readily removed by processing the compound containing the group with an acid such as trifluoroacetic acid or hydrogen chloride in an organic solvent e.g. methanol, ethanol, ethyl acetate and dioxane. And, the benzyloxycarbonyl group can be removed by subjecting the compound containing the group to catalytic reduction in the presence of a metal such as platinum, palladium or Raney's nickel or a mixture of such metal and an optional carrier.

While salts of the compound (I) can be obtained by the reaction for producing the compound (I) itself, they can be produced also by adding, upon necessity, an acid, alkali or base.

Thus-obtained object compound (I) of this invention can be isolated from the reaction mixture by a conventional separation and purification means such as extraction, concentration, neutralization, filtration, recapitalization, column chromatography and thin-layer chromatography.

In the compound (I), at least two stereoisomers can be present. These individual isomers or a mixture thereof are included in the scope of the present invention. And, it is also possible to produce these isomers individually.

By conducting the reaction as described using a single isomer of the compound (III), a single optical isomer of the compound (I) can be obtained.

And, when the product is a mixture of two or more isomers, it can be separated into respective isomers by a conventional separation method, for example, a method of causing formation of a salt with an optically active acid (e.g. camphor sulfonic acid, tartaric acid and dibenzoyl tartaric acid), an optically active base (e.g. cinchonine, cinchonidine, quinine, quinidine and α-methylbenzylamine), or various chromatographic means or fractional recrystallization.

The starting compounds (II) and (III) in the present invention are per se known compounds, or can be produced in a manner analogous to per se known methods. While the compound (III) can be produced by a method analogous to per se known methods, it can also be produced by the methods shown by the following reaction scheme.

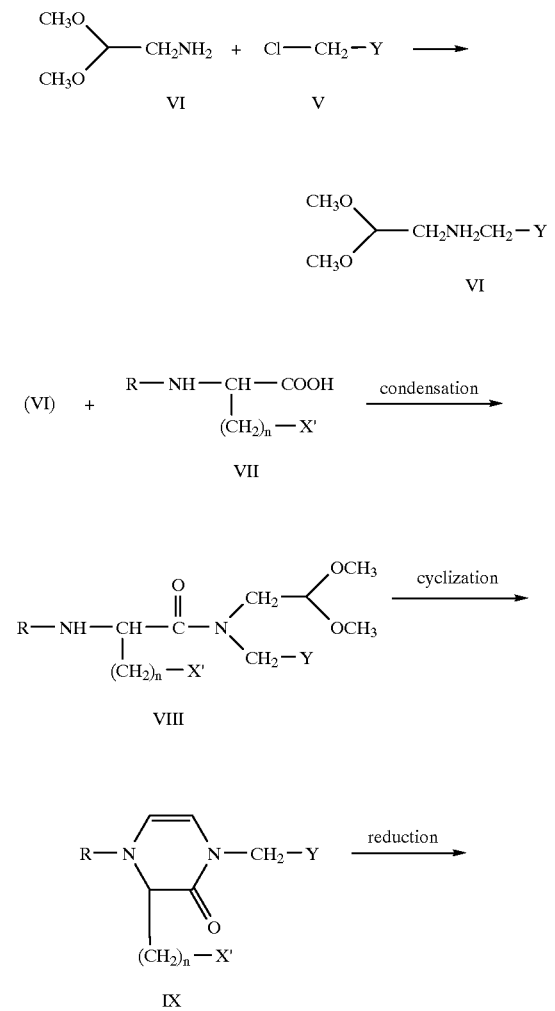

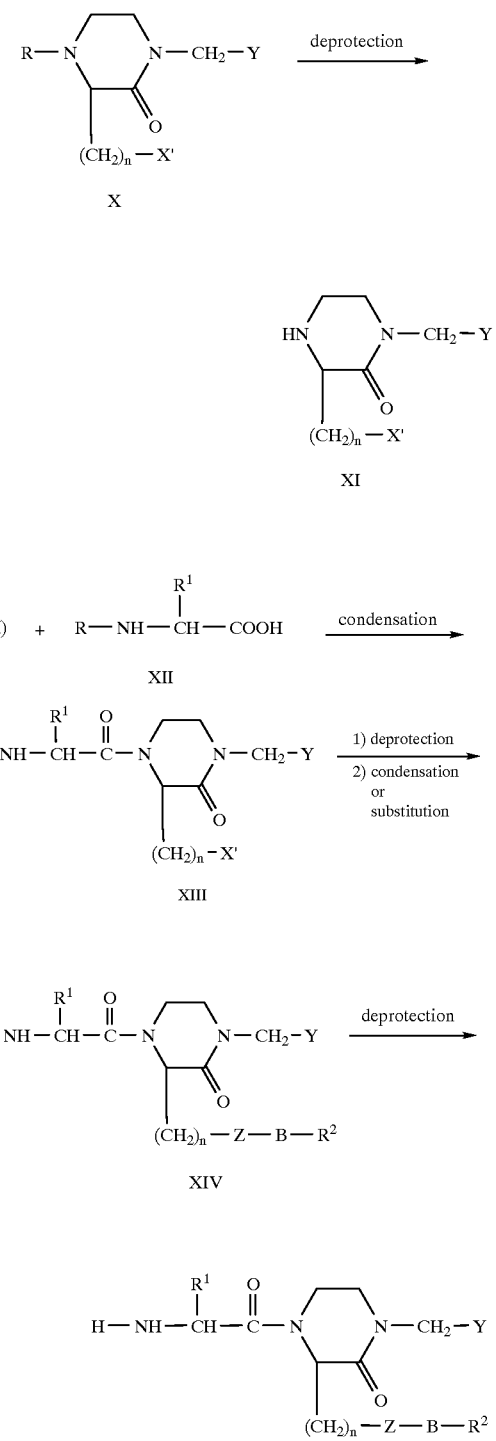

In the above reaction formulae, R is an amino-protective group, and stands for benzyloxycarbonyl group or tert-butoxycarbonyl group. X' stands for a protected amino group (as the protective group, use is made of, for example, benzyloxycarbonyl group and tert-butoxycarbonyl group), a protected carboxyl group (as the protective group, use is made of, for example, methyl, ethyl, benzyl and tert-butyl group), a protected hydroxyl group (as the protective group, use is made of, for example, benzyl group and tert-butyl group) or a protected mercapto group (as the protective group, use is made of, for example, benzyl group and trityl group). Y stands for a protected carboxyl group (as the protective group, use is made of, for example, benzyl or tert-butyl group).

The method of producing the compound (III) shown by the above reaction scheme is explained in further detail. The reaction for obtaining the compound (VI) by reacting the compound (IV) with the compound (V) is a conventional alkylation of amino group. More specifically stating, the compound (IV) is allowed to react with the compound (V) usually at a temperature ranging from 0 to 100° C. for a period ranging from about 15 minutes to 5 hours in the presence of a base (e.g. an inorganic base such as sodium carbonate, potassium carbonate, potassium hydrogencarbonate or cesium fluoride, or an organic base such as triethylamine, pyridine or 4-N,N-dimethylaminopyridine) to give the compound (VI). As the reaction solvent, mention is made of an organic solvent such as acetonitrile, N,N-dimethylformamide, tetrahydrofuran, toluene and methylene chloride.

The subsequent reaction of producing the compound (VIII) by subjecting the compound (VI) to condensation with the the compound (VII) is a conventional peptide-linkage reaction, which can be conducted under substantially the same reaction conditions as those for the condensation reaction of the compound (II) with the compound (III).

Cyclization of the compound (VIII) into the compound (IX) is a cyclization reaction with an acid catalyst. As the catalyst, use is made of, for example, p-toluenesulfonic acid, camphorsulfonic acid and methanesulfonic acid. The compound (IX) can be produced by conducting the reaction usually in a solvent such as toluene, benzene, ethyl acetate or 1,2-dichloroethane at a temperature ranging from 0 to 100° C., preferably from 30 to 80° C.

The subsequent reaction for reducing the compound (IX) to the compound (X) can be conducted by catalytic reduction using, as a catalyst, a metal such as platinum, palladium or Raney nickel, or a mixture of them with an optional carrier, or a reduction using a metallic hydride, for example, sodium borohydride. The above reactions are conducted usually in an organic solvent (e.g. methanol, ethanol, dioxane and ethyl acetate), and the reaction temperature ranges, in general, preferably from about −20 to about 100° C. This reaction can be conducted under normal pressure or under elevated pressure. When R is benzyloxycarbonyl group, the reaction of removing the protective group of R proceeds simultaneously to obtain the compound (XI).

Reactions for removing protective groups in (X) to (XI) and (XVI) to (III) are conventional reactions for removing protective groups of amino groups, and, in the case where R stands for a benzyloxycarbonyl group, the protective group can be removed by catalytic reduction using, as the catalyst, a metal such as platinum, palladium or Raney's nickel or a mixture of the metal with an optional carrier. And, when R stands for tert-butoxycarbonyl group, the protective group can be easily removed by the use of an acid such as trifluoroacetic acid or hydrogen chloride in an organic solvent such as methanol, ethanol, ethyl acetate or dioxane.

The condensation reaction of the compound (XI) with the compound (XII) is an amide-linkage formation reaction, which can be conducted in substantially the same manner as in the condensation of the compound (II) with the compound (III).

The reaction for converting the compound (XIII) to the compound (XIV) can be conducted usually in two steps, i.e. deprotection and condensation or substitution reaction. In the case where X' is a protected amino group, the amino group is deprotected under substantially the same conditions as in the conversion of the compound (X) into the compound (XI), which is then condensed with a corresponding carboxylic acid under substantially the same conditions as in the condensation of the compound (II) with the compound (III), or subjected to substitution reaction with a corresponding halogenide under substantially the same conditions as in the reaction employed for the substitution reaction of the compound (IV) and the compound (V). When X' is a protected carboxyl group, the protecting group can be removed by a per se known method. For example, the protective group is methyl or ethyl ester, it can be removed by allowing a base such as sodium hydroxide, potassium hydroxide or lithium hydroxide to act in an organic solvent such as methanol ethanol, tetrahydrofuran and dioxane. And, a compound having a benzyl ester group, the compound can be converted into a carboxylic acid derivative by subjecting to hydrogenation in the presence of a precious metal catalyst such as palladium and platinum, and a compound having a tert-butyl ester group can be converted into a carboxylic acid derivative by processing with an acid such as trifluoroacetic acid or hydrogen chloride. Thus-obtained carboxylic acid can be led to the compound (XIV) by condensing with a corresponding amine or hydroxy compound by the method employed for the condensation of the compound (II) with the compound (III).

In the above-mentioned methods of producing the compound (I) and its intermediates, compounds to be employed for the reactions may, unless undesirable effects are brought about, be in the form of a salt with, for example, an inorganic acid such as hydrochloride, hydrobromide, sulfate, nitrate or phosphate, an organic acid such as acetate, tartrate, citrate, fumarate, maleate, toluenesulfonate or methanesulfonate, a metal salt such as sodium salt, potassium salt or aluminum salt, or a salt with a base such as triethylamine salt, guanidine salt, ammonium salt, hydrazine salt or quinine salt.

When the compound (I) is obtained in the free form by the above-mentioned production method, it can be converted to a salt thereof by a conventional method, and when the compound (I) is obtained as a salt, it can be converted to the compound (I) by a conventional method.

The compounds of the formula (I) (including their hydrates) are low in toxicity and are used safely, which inhibit both the binding of fibrinogen, fibronectin and von Willebrand factor to the fibrinogen receptor of blood platelets (Glycoprotein IIb/IIIa) and the binding thereof and other adhesive proteins, such as vitronectin collagen and laminin, to the corresponding receptors on the surface of various types of cells.

Hence, the compounds of this invention exert influence on cell—cell and cell-matrix interactions. They prevent, in particular, the development of thrombus and can be used for treatment or prophylaxis of diseases such as angina pectoris, unstable angina, acute myocardial infarction, Kawasaki disease, acute or chronic heart failure, transient ischemic attack (TIA), cerebral apoplexy, cerebral ischemic disturbance in acute phase of cerebral thrombosis, dissecting aneurysm of the aorta, cerebral vasospasm after subarachnoid hemorrhage, acute or chronic renal disease (e.g. acute or chronic renal disease due to overagglutination such as snake venom and immunopathy), chronic and acute glomerulonephrits, diabetic nephropathy and nerve disturbance, nephrotic syndrome, liver diseases, pulmonary embolism, bronchial asthma, pulmonary edema, adult respiratory distress syndrome (ARDS), arteriosclerotic obliteration, peripheral arterial obstruction, deep vein thrombosis, vibration disease, peripheral obstruction complicated with diabetes mellitus, thrombotic thrombocytopenic purpura (TTP), disseminated intravascular coagulation (DIC), sepsis, surgical or infective shock, postoperative and post-delivery trauma, premature separation of placenta, incompatible blood transfusion, systemic lupus erythematosus, Raynaud's disease, inflammations, arteriosclerosis, hemolytic uremic syndrome, symmetric peripheral necrosis, bedsore and hemorrhoids in mammals including humans (e.g. mouse, rat, guinea pig, dog, rabbit and human). And, the compounds (I) of this invention can be used for preventing thrombosis due to cardiopulmonary bypass surgical operation, surgical operation for pump oxygenator, atrial fibrillation or fracture of hip joint, prosthetic valve replacement, artificial blood vessel and organs, or preventing thrombocytopenia during artificial dialysis, and further for secondary prophylaxis of myocardial infarction. The preventing thrombocytopenia during artificial dialysis also means preventing coagulation or non-washable blood in shunt of extracorporeal dialysis.

Further, the compound (I) of this invention can be used for coronary thrombolytic therapy (e.g. enhancing the action of thrombolytic agent such as tissue plasminogen activator (TPA)) and for preventing reobstruction, for preventing reobstruction and restenosis of coronary arteries after PTCA (percutaneous transluminal coronary angioplasty) or stent-indwelling and atherectomy, for preventing reobstruction and restenosis after surgical operation for coronary artery bypass, for preventing ischemic complication (e.g. myocardial infarction, death) after PTCA or coronary thrombolytic therapy, and, besides the compound (I) inhibits metastasis of tumors and can be used as an antitumor agent.

And, in case where the compound of this invention is used together with a pharmaceutical preparation whose pharmacological actions are the same or different from that of the compound of this invention, two or more kinds of drugs may be incorporated into one and the same pharmaceutical preparation, or these components can be incorporated into one and the same pharmaceutical preparation (e.g. powdery preparation and injection) at the time of administration. Further, pharmaceutical preparations independently formulated may be administered to one and the same subject simultaneously or at an optional time lag.

Pharmaceutical compositions containing compounds of the formula (I) (including their hydrates and salts) can be administered orally in the form of, for example, tablets, lacquered tablets, sugar-coated tablets, hard and soft gelatin capsules, solutions, emulsions or suspensions, or rectally in the form of suppositories, or as spray. However, administration can also be performed non-orally, for example in the form of injectable solutions.

Pharmaceutical preparations of the above-mentioned forms can be formulated by respectively conventional methods using, when necessary, adequate excipients.

To prepare tablets, lacquered tablets, sugar-coated tablets and gelatin capsules, an active compound can be mixed with pharmaceutically inert inorganic or organic excipients. Typical examples of such excipients, which can be used for tablets, sugar-coated tablets and gelatin capsules, include lactose, corn starch or derivatives thereof, talc, and stearic acid or salts thereof. Examples of suitable excipients for soft gelatin capsules are vegetable oil, wax, fat, and, semisolid or liquid polyol. However, no excipients whatever are necessary with soft gelatin capsules when the characteristic features of the active compound are appropriate.

Examples of suitable excipients for the preparation of solutions and syrupy preparations are water, polyol, sucrose, invert sugar and glucose. Suitable examples for injectable solution are water, alcohol, polyol, glycerol and vegetable oil.

Suitable examples for suppositories are natural or hardened oil, wax, fat and semiliquid or liquid polyol. The pharmaceutical compositions can additionally contain a preservative, a solubilizer, a stabilizer, a wetting agent, an emulsifier, a sweetener, a colorant, a flavoring, a salt to alter the osmotic pressure, a buffer, a coating agent or an antioxidant.

The dosage of the active compound for controlling or preventing the diseases referred to hereinbefore can vary within a wide range and can, of course, be adjusted to suit the individual circumstances in each particular case. While the dosage varies with the subject diseases, symptoms, subject patients and administration routes, when administered orally to a patient of unstable angina, or, ischemic complication or reobstruction of coronary or restenosis of coronary after PTCA or coronary thrombolytic therapy, a dose of about 1 to 500 mg, preferably about 10 to 200 mg, per day for an adult (60 kg) is appropriate. When administered non-orally to a patient of transient ischemic attack (TIA), unstable angina, or, ischemic complication or reobstruction of coronary or restenosis of coronary after PTCA or coronary thrombolytic therapy, a dose of about 0.05 to 50 mg, preferably about 1 to 20 mg/kg per day to an adult (60 kg), divided into one to three times.

BEST MODE FOR CARRTING OUT THE INVENTION

The following test examples and working examples will describe the present invention in further detail, but they are not intended to limit the present invention in any way.

TEST EXAMPLE 1

Determination of platelet aggregation in vitro

Test Method

Blood was collected from abdominal aorta of guinea pigs under anesthesia with pentobarbital (20 mg/kg, i.p.) using sodium citrate as an anticoagulant (final concentration: 0.315%). The sodium citrate—supplemented blood was centrifuged at 950 rpm for 10 minutes and 2,000 rpm for 10 minutes respectively at room temperature to obtain platelet rich plasma (PRP) and platelet poor plasma (PPP). The number of platelet was counted an automatic platelet counter (Sysmex E2500, Toaiyo-denshi). PRP was diluted with PPP to adjust the number of platelets to be 500,000/$\mu$l. Platelet aggregation was measured as follows, in accordance with Born's method (Nature 194: 927, 1962), using an 8-channel aggregometer (NBS HEMA TRACER VI, Niko Bioscience Inc.): The PRP (250 $\mu$l) was incubated at 37° C. for 2 minutes, to which was then added 25 $\mu$l of a test drug solution. Two minutes later, 25 $\mu$l of an agent (ADP) for causing agglutination. The effect of the test drug was shown by the inhibition rate of the maximum aggregation rate of the test group against that of the control group. ADP was used in the minimum concentration (0.6–1 $\mu$M) capable of obtaining maximum aggregation.

The results are shown in Table 1.

TABLE 1

Inhibitory effect on platelet aggregation in guinea pigs by ADP of the compounds of Working Examples

| W. Ex. No. | Inhibition of platelet aggregation by ADP, $IC_{50}$ (M) |
|---|---|
| 1 | $5.2 \times 10^{-7}$ |
| 2 | $3.7 \times 10^{-8}$ |
| 5 | $1.6 \times 10^{-8}$ |
| 6 | $2.0 \times 10^{-8}$ |
| 7 | $1.9 \times 10^{-8}$ |
| 8 | $1.2 \times 10^{-8}$ |
| 9 | $1.8 \times 10^{-7}$ |
| 10 | $2.0 \times 10^{-7}$ |
| 11 | $2.3 \times 10^{-7}$ |
| 12 | $2.5 \times 10^{-8}$ |
| 13 | $1.1 \times 10^{-7}$ |
| 15 | $5.1 \times 10^{-8}$ |
| 16 | $4.4 \times 10^{-8}$ |
| 17 | $2.4 \times 10^{-7}$ |
| 18 | $1.3 \times 10^{-7}$ |
| 19 | $1.8 \times 10^{-7}$ |
| 22 | $3.8 \times 10^{-6}$ |
| 23 | $1.7 \times 10^{-8}$ |
| 24 | $2.5 \times 10^{-7}$ |
| 25 | $5.4 \times 10^{-8}$ |
| 26 | $8.4 \times 10^{-8}$ |
| 27 | $1.8 \times 10^{-8}$ |
| 28 | $1.9 \times 10^{-8}$ |
| 30 | $1.9 \times 10^{-5}$ |
| 31 | $1.9 \times 10^{-7}$ |
| 32 | $5.3 \times 10^{-8}$ |

TEST EXAMPLE 2

Bleeding time in guinea pigs and determination of ex vivo platelet aggregation inhibitory action Test Method A. Animals: Male Hartley guinea pigs (body weight: about 400 g) were employed. These animals were intravenously infused continuously, under anesthesia with pentobarbital, with a physiological saline solution or receptor-antagonist dissolved in the solution at a dose of 10 μl/kg/min.

B. Determination of bleeding time (BT): After the continuous infusion for 90 minutes, the thigh of each animal was applied with a rubber cuff and charged with 40 mmHg, then given an incised sound with Simplate R (Organon Teknika). Thereafter, at 30 sec. each interval, blood was absorbed into a filter paper. The time until no more blood was absorbed into the filter paper was measured. The bleeding time of normal five guinea pigs was about 276 sec.

C. Collection of blood: After 90 minutes of the continuous infusion, blood was collected from abdominal aorta using sodium citrate (whole blood:3.15% citric acid solution=9:1 by volume). The sodium citrate-supplemented blood was centrifuged at 1000×g for 3 to 5 seconds and 1000×g for 20 minutes to obtain platelet rich plasma (PRP) and platelet poor plasma (PPP). PRP was diluted with PPP to adjust the number of platelets to about 400,000/μl.

D. Platelet aggregation experiment: Platelet aggregation was measured by using an 8-channel photo-extinction type platelet aggregometer (NBS/HEMA TRACER 801, Niko Bioscience). PRP (220 μl) was put in a disposal cuvette equipped with a stirring rod. The PRP was set in the aggregometer and incubated for two minutes at 37° C., to which was added 20 μl of ADP (0.5 to 1 μM), and the changes of transmittance were recorded. The difference of PRP and PPP in photo-extinction was assumed 100%, and, with the maximum photo-extinction rates, the maximum aggregation rates (%) were determined. The effects of the drugs were determined by comparing the maximum aggregation rates (%) of animals continuously infused with a physiological saline solution with those of animals continuously infused with receptor antagonist. The results are shown in Table 2.

TABLE 2

Dosages of compounds of working examples in guinea pigs, bleeding time and ex vivo platelet aggregation inhibition

| W. Ex. No. | Dosage (μg/kg/min) | Bleeding time (sec.) | Inhibitory rate (%) |
|---|---|---|---|
| (physiological saline solution) | — | 276 ± 35 | — |
| 2 | 2 | 308 ± 33 | 100 |
| 15 | 3 | 250 ± 26 | 100 |

REFERENCE EXAMPLE 1

(S)-3-(3-t-Butoxycarbonylaminopropyl)-2-oxopiperazine-1-acetic acid t-butyl ester oxalate In 54.6 cc of acetone were dissolved (2,2-dimethoxyethyl) aminoacetic acid t-butyl ester (6.0 g, 27.7 mmol) and N—Z—Orn(Boc)—OH (10.0 g, 27.7 mmol). To the solution was added, at 15° C. under stirring, 1-ethyl-3-(3-dimethylaminopropyl)-carbodiimide hydrochloride (5.6 g, 29.2 mmol). The mixture was stirred for one hour at room temperature, and concentrated under reduced pressure. The concentrate was dissolved in ethyl acetate, and washed with a 5% aqueous solution of potassium hydrogensulfate and a saturated aqueous solution of sodium hydrogencarbonate. The organic layer was concentrated under reduced pressure to give a pale yellow oily substance. This oily substance and p-toluenesulfonic acid 1.0 hydrate (1.04 g, 5.46 mmol) were dissolved in 137 cc of toluene, and the solution was stirred for two hours at 70° C. The reaction mixture was poured into a saturated aqueous solution of sodium hydrogencarbonate. The mixture was subjected to extraction with ethyl acetate. The organic layer was concentrated under reduced pressure, and purified by means of a silica gel column chromatography (hexane/ethyl acetate=3/2) to give 8.3 g of a pale yellow oily substance. This oily substance (8.3 g, 16.5 mmol) was dissolved in 166 cc of ethyl acetate, to which was added 1.7 g of 10% Pd-C, and then the mixture was stirred for two hours under hydrogen atmosphere. The catalyst was filtered off, and the filtrate was dissolved in 16.6 cc of methanol. To the solution was added oxalic acid 2.0 hydrate (2.1 g, 16.5 mmol), and the mixture was concentrated under reduced pressure. Resulting crystalline product was washed with ethyl acetate to afford 5.1 g (66.8%) of the titled compound as white crystals.

Specific optical rotation: $[\alpha]_D$ −29.3° (c=0.73, $H_2O$) m.p.: 181° C.; Elemental Analysis for $C_{18}H_{33}N_3O_5 \cdot (CO_2H)_2$ (461.511): Calcd.: C, 52.05; H, 7.64; N, 9.10; Found : C, 51.98; H, 7.61; N, 9.20.

REFERENCE EXAMPLE 2

(S)-4-Benzyloxycarbonylaminoacetyl-3-(3-t-butoxycarbonylaminopropyl)-2-oxopiperazine-1-acetic acid t-butyl ester In a saturated aqueous solution of sodium hydrogencarbonate was dissolved (S)-3-(3-t-butoxycarbonylaminopropyl)-2-oxopiperazine-1-acetic acid t-butyl ester oxalate (1.6 g, 3.47 mmol). The solution was subjected to extraction with ethyl acetate, and the extract solution was concentrated under reduced pressure. The concentrate and N—Z—Gly—OH (0.87 g, 4.16 mmol) were dissolved in 16.0 cc of acetone. To the solution was added, at 15° C. under stirring, 1-ethyl-3-(3-dimethylaminopropyl)-carbodiimide hydrochloride (0.87 g, 4.51 mmol). The mixture was stirred for one hour at room temperature, and the reaction mixture was concentrated under reduced pressure. The concentrate was washed with a 5% aqueous solution of potassium hydrogensulfate and a saturated aqueous solution of sodium hydrogencarbonate. The organic layer was concentrated under reduced pressure, and the concentrate was purified by means of a silica gel column chromatography (ethyl acetate) to afford 1.95 g (100%) of the titled compound as a colorless amorphous powdery product.

IR ν max $cm^{-1}$: 3360, 2970, 2930, 1713, 1650, 1513, 1448, 1363, 1246, 1158, 1045, 964, 848, 744, 695; NMR ($CDCl_3$) δ: 1.43(9H,s), 1.46(9H,s), 1.50–2.20(4H,m), 3.02–4.28(10H,m), 4.52–4.80(1H,m), 5.01(1H,dd,J=8.8,4.6 Hz), 5.13(2H,s), 5.64–5.86(1H,m), 7.37(5H,s)

WORKING EXAMPLE 1
(S)-4-(4-Amidinobenzoylamino)acetyl-3-(3-aminopropyl)-2-oxopiperazine-1-acetic acid trifluoroacetate In 13.4 cc of methanol was dissolved (S)-4-benzyloxycarbonylaminoacetyl-3-(3-t-butoxycarbonyl-aminopropyl)-2-oxopiperazine-1-acetic acid t-butyl ester (1.34 g, 2.38 mmol). To the solution was added 0.54 g of 10% Pd-C, and the mixture was stirred for 30 minutes under hydrogen atmosphere. The catalyst was filtered off, and the filtrate was concentrated under reduced pressure. The concentrate and sodium hydrogencarbonate (0.4 g, 4.76 mmol) were dissolved in a mixture of 26.8 cc of water and 13.4 cc of 1,4-dioxane. To the solution was added, at room temperature under stirring, 4-amidinobenzoyl chloride hydrochloride (0.68 g, 3.09 mmol). The mixture was stirred for three hours, then pH of the reaction mixture was adjusted to 4 with 1N HCl, which was concentrated to dryness. The concentrate was dissolved in 3.75 cc of trifluoroacetic acid, and the solution was stirred for 2 hours at room temperature. The reaction mixture was concentrated under reduced pressure, which was purified by means of a CHP-20 (Mitsubishi Chemical Industries, Ltd.) column chromatography (water) to afford 1.0 g (63.3%) of the titled compound as a colorless amorphous powdery product.

Specific optical rotation: $[α]_D$ +35.4° (c=0.75, MeOH); Elemental Analysis for $C_{19}H_{26}N_6O_5.2CF_3CO_2H.H_2O$ (664.515): Calcd.: C, 41.57; H, 4.55; N, 12.65; Found : C, 41.86; H, 4.50; N, 12.60.

WORKING EXAMPLE 2
(S)-4-(4-Amidinobenzoylamino)acetyl-3-{3-(4-amidinobenzoyl)amino}propyl-2-oxopiperazine-1-acetic acid trifluoroacetate In a mixture of 5.0 cc of water and 2.5 cc of 1,4-dioxane were dissolved (S)-4-(4-amidinobenzoylamino)acetyl-3-(3-aminopropyl)-2-oxo-piperazine-1-acetic acid trifluoroacetate (0.5 g, 0.94 mmol) and sodium hydrogencarbonate (0.32 g, 3.76 mmol). To the solution was added, at room temperature under stirring, 4-amidinobenzoyl chloride hydrochloride (0.22 g, 0.99 mmol). The mixture was stirred for two hours, whose pH was adjusted to 4 with 1N HCl, followed by concentration under reduced pressure. The concentrate was purified by means of a CHP-20 column chromatography ($H_2O$ Right→5% $CH_3CN$) to afford 0.34 g (50.7%) of the titled compound as a colorless amorphous powdery product.

Specific optical rotation: $[α]_D$ +41.9° (c=0.73, MeOH); Elemental Analysis for $C_{27}H_{32}N_8O_6.CF_3CO_2H.2H_2O$ (714.653): Calcd.: C, 48.74; H, 5.22; N, 15.68; Found : C, 48.52; H, 5.22; N, 15.57.

REFERENCE EXAMPLE 3
(S)-3-(4-t-Butoxycarbonylaminobutyl)-2-oxopiperazine-1-acetic acid t-butyl ester oxalate In substantially the same manner as in Reference Example 1, the titled compound was synthesized by using N—Lys(Boc)—OH.

Specific optical rotation: $[α]_D$ −29.0° (c=1.02, DMSO) m.p.: 170–172° C.; Elemental Analysis for $C_{19}H_{35}N_3O_5.(CO_2H)_2$ (475.540): Calcd.: C, 53.04; H, 7.84; N, 8.84; Found : C, 52.75; H, 7.65; N, 8.66.

REFERENCE EXAMPLE 4
(S)-4-Benzyloxycarbonylaminoacetyl-3-(4-t-butoxycarbonylaminobutyl)-2-oxopiperazine-1-acetic acid t-butyl ester In substantially the same manner as in Reference Example 2, the titled compound was synthesized by using (S)-3-(4-t-butoxycarbonylaminobutyl)-2-oxopiperazine-1-acetic acid t-butyl ester oxalate.

IR ν max $cm^{-1}$: 3400, 2990, 2945, 1713, 1657, 1520, 1458, 1368, 1253, 1166, 1070, 745, 700; NMR($CDCl_3$) δ: 1.42(9H,s), 1.46(9H,s), 1.18–2.12(6H,m), 2.92–4.28(10H, m), 4.48–4.84(1H,m), 5.02(1H,dd,J=8.6,4.8 Hz), 5.13(2H, s), 5.60–5.88(1H,m), 7.36(5H,s)

WORKING EXAMPLE 3
(S)-4-(4-Amidinobenzoylamino)acetyl-3-(4-aminobutyl)-2-oxopiperazine-1-acetic acid trifluoroacetate In substantially the same manner as in Working Example 1, the titled compound was synthesized by using (S)-[4-benzyloxycarbonylaminoacetyl-3-(4-t-butoxycarbonylamino-butyl)-2-oxopiperazin-1-yl)-acetic acid t-butyl ester.

Specific optical rotation: $[α]_D$ +46.8° (c=1.01, $H_2O$); Elemental Analysis for $C_{20}H_{28}N_6O_5.1.7CF_3CO_2H.2H_2O$ (662.394): Calcd.: C, 42.43; H, 5.13; N, 12.69; Found : C, 42.53; H, 4.88; N, 12.78.

WORKING EXAMPLE 4
(S)-4-(4-Amidinobenzoylamino)acetyl-3-{4-(4-amidinobenzoylamino)butyl}-2-oxopiperazine-1-acetic acid monotrifluoroacetate monohydrochloride In substantially the same manner as in Working Example 2, the titled compound was synthesized by using (S)-4-(4-amidinobenzoylamino)acetyl-3-(4-aminobutyl)-2-oxopiperazine-1-acetic acid trifluoroacetate.

Specific optical rotation: $[α]_D$ +44.3° (c=1.01, $H_2O$); Elemental Analysis for $C_{28}H_{34}N_8O_6.CF_3CO_2H.HCl.3H_2O$ (783.157): Calcd.: C, 46.01; H, 5.41; N, 14.31; Found : C, 46.23; H, 5.22; N, 14.54.

REFERENCE EXAMPLE 5
(S,S)-4-{2-Benzyloxycarbonylamino-3-(4-methoxyphenyl)propionyl}-3-(3-t-butoxycarbonylaminopropyl)-2-oxopiperazine-1-acetic acid t-butyl ester In substantially the same manner as in Reference Example 2, the titled compound was synthesized by using N—Z—Tyr(OMe)—OH.

IR ν max $cm^{-1}$: 3360, 2975, 2925, 1710, 1643, 1512, 1448, 1360, 1245, 1152, 1033, 743, 696; NMR($CDCl_3$) δ: 1.41(9H,s), 1.44(9H,s), 1.30–2.10(3H,m), 2.20–2.44(1H,m), 2.80–3.84(10H,m), 3.77(3H,s), 4.23(1H,d,J=17.2 Hz), 4.50–4.85(1H,m), 4.93(1H,dd,J=6.2,7.0 Hz), 5.09(2H,dd,J= 12.0,16.4 Hz), 5.67(1H,d,J=8.8 Hz), 6.80(2H,d,J=8.8 Hz), 7.09(2H,d,J=8.8 Hz), 7.35(5H,s) WORKING EXAMPLE 5

(S,S)-4-{2-(4-Amidinobenzoylamino)-3-(4-methoxyphenyl)-propionyl}-3-(3-aminopropyl)-2-oxopiperazine-1-acetic acid trifluoroacetate In substantially the same manner as in Working Example 1, the titled compound was synthesized by using (S,S)-4-{2-benzyloxycarbonylamino-3-(4-methoxyphenyl) propionyl}-3-(3-t-butoxycarbonylaminopropyl)-2-oxopiperazine-1-acetic acid t-butyl ester.

Specific optical rotation: $[\alpha]_D$ +78.2° (c=0.62, H$_2$O); Elemental Analysis for $C_{27}H_{34}N_6O_6 \cdot CF_3CO_2H \cdot 3H_2O$ (706.672): Calcd.: C, 49.29; H, 5.85; N, 11.89; Found : C, 49.53; H, 5.68; N, 11.90.

WORKING EXAMPLE 6

(S,S)-4-{2-(4-Amidinobenzoylamino)-3-(4-methoxyphenyl)-propionyl}-3-{3-(4-amidinobenzoylamino)propyl}-2-oxopiperazine-1-acetic acid trifluoroacetate In substantially the same manner as in Working Example 2, the titled compound was synthesized by using (S,S)-4-{2-(4-amidinobenzoylamino)-3-(4-methoxyphenyl) propionyl}-3-(3-aminopropyl)-2-oxopiperazine-1-acetic acid trifluoroacetate.

Specific optical rotation: $[\alpha]_D$ +52.8° (c=0.76, MeOH); Elemental Analysis for $C_{35}H_{40}N_8O_7 \cdot CF_3CO_2H \cdot 3H_2O$ (852.820): Calcd.: C, 52.11; H, 5.55; N, 13.14; Found : C, 52.27; H, 5.50; N, 13.26.

REFERENCE EXAMPLE 6

(S,S)-4-{2-Benzyloxycarbonylamino-3-(4-methoxyphenyl)-propionyl}-3-(4-t-butoxycarbonylaminobutyl)-2-oxopiperazine-1-acetic acid t-butyl ester In substantially the same manner as in Reference Example 2, the titled compound was synthesized by using (S)-3-(4-t-butoxycarbonylaminobutyl)-2-oxopiperazine-1-acetic acid t-butyl ester oxalate and N—Z—Tyr(OMe)—OH.

IR ν max cm$^{-1}$: 3345, 2975, 2930, 1712, 1646, 1512, 1447, 1364, 1244, 1155, 1034, 743, 696; NMR(CDCl$_3$) δ: 1.43(9H,s), 1.44(9H,s), 1.00–2.45(6H,m), 2.80–3.90(10H, m), 3.78(3H,s), 4.23(1H,d,J=17.4 Hz), 4.70–5.10(2H,m), 5.10(2H,d,J=2.4 Hz), 5.74(1H,d,J=8.8 Hz), 6.81(2H,d,J=8.6 Hz), 7.10(2H,d,J=8.6 Hz), 7.35(5H,s)

WORKING EXAMPLE 7

(S,S)-4-{2-(4-Amidinobenzoylamino)-3-(4-methoxyphenyl)propionyl}-3-(4-aminobutyl)-2-oxopiperazine-1-acetic acid trifluoroacetate In substantially the same manner as in Working Example 1, the titled compound was synthesized by using (S,S)-[4-{2-benzyloxycarbonylamino-3-(4-methoxyphenyl)-propionyl}-3-(4-t-butoxycarbonylaminobutyl)-2-oxopiperazin-1-yl]-acetic acid t-butyl ester.

Specific optical rotation: $[\alpha]_D$ +53.1° (c=0.64, MeOH); Elemental Analysis for $C_{28}H_{36}N_6O_6 \cdot CF_3CO_2H \cdot 3H_2O$ (720.699): Calcd.: C, 50.00; H, 6.01; N, 11.66; Found : C, 49.87; H, 5.77; N, 11.45.

WORKING EXAMPLE 8

(S,S)-4-{2-(4-Amidinobenzoylamino)-3-(4-methoxyphenyl)propionyl}-3-{4-(4-amidinobenzoylamino) butyl}-2-oxopiperazine-1-acetic acid hydrochloride In substantially the same manner as in Working Example 2, the titled compound was synthesized by using (S,S)-4-{2-(4-amidinobenzoylamino)-3-(4-methoxyphenyl) propionyl}-3-(4-aminobutyl)-2-oxopiperazine-1-acetic acid trifluoroacetate.

Specific optical rotation: $[\alpha]_D$ +54.5° (c=0.88, H$_2$O); Elemental Analysis for $C_{36}H_{42}N_8O_7 \cdot HCl \cdot 6H_2O$ (843.329): Calcd.: C, 51.27; H, 6.57; N, 13.29; Found : C, 51.24; H, 6.37; N, 13.26.

REFERENCE EXAMPLE 7

(S)-4-Benzyloxycarbonylaminoacetyl-3-{3-(6-tbutoxycarbonylaminohexanoylamino)propyl}-2-oxopiperazine-1-acetic acid In 3.0 cc of trifluoroacetic acid was dissolved (S)-4-benzyloxycarbonylaminoacetyl-3-(3-t-butoxycarbonylaminopropyl)-2-oxopiperazine-1-acetic acid t-butyl ester (0.6 g, 1.07 mmol) produced in Reference Example 2. The solution was stirred for 30 minutes at room temperature, which was concentrated under reduced pressure. In 2.1 cc of DMF were dissolved 6-t-butoxyaminocaproic acid (0.26 g, 1.12 mmol), 1-ethyl-3-(3-dimethylaminopropyl)-carbodiimide hydrochloride (0.22 g, 1.14 mmol) and 1-hydroxybenzotriazole (0.15 g, 1.12 mmol). The solution was stirred for one hour, to which was added 2.1 cc of a DMF solution of the concentrate obtained above and triethylamine (0.3 cc, 2.14 mmol). The mixture was stirred for 4 hours at room temperature. The reaction mixture was diluted with ethyl acetate, which was washed with a 5% aqueous solution of potassium hydrogensulfate and a saturated aqueous solution of sodium hydrogencarbonate. The organic layer was concentrated under reduced pressure, which was purified by means of a silica gel column chromatography (ethyl acetate/methanol/acetic acid=20/10/0.6) to afford 0.42 g (y. 63.3%) of the titled compound as a colorless amorphous powdery product.

IR ν max cm$^{-1}$: 3320, 2930, 1643, 1533, 1448, 1203, 1173, 1046; NMR(CDCl$_3$) δ: 1.42(9H,s), 1.20–2.09(10H, m), 2.17(2H,t,J=7.3 Hz), 2.92–4.20(12H,m), 4.80–4.98(1H, m), 5.11(2H,s), 7.22–7.44(5H,m)

WORKING EXAMPLE 9

(S)-4-(4-Axmidinobenzoylamino)acetyl-3-{3-(6-aminohexanoylamino)propyl}-2-oxopiperazine-1-acetic acid trifluoroacetate In 8.4 cc of methanol was dissolved (S)-4-benzyloxycarbonylaminoacetyl-3-{3-(6-t-butoxycarbonylaminohexanoylamino)propyl}-2-oxopiperazine-1-acetic acid (0.42g, 0.68 mmol). To the solution was added 0.17 g of 10% Pd-C, and the mixture was stirred for one hour under hydrogen atmosphere. The catalyst was filtered off, and the filtrate was concentrated under reduced pressure. The concentrate and sodium hydrogencarbonate (0.18 g, 2.14 mmol) were dissolved in a mixture of 8.4 cc of water and 4.2 cc of 1,4-dioxane. To the solution was added, while stirring at room temperature, 4-amidinobenzoyl chloride hydrochloride (0.20 g, 0.93 mmol). The mixture was stirred for one hour, then the pH of the reaction mixture was adjusted to 4 with 1N HCl, followed by concentration to dryness. The concentrate was dissolved in 4.3 cc of trifluoroacetic acid, and the solution was stirred for one hour at room temperature. The reaction mixture was concentrated under reduced pressure, which was purified by means of a CHP-20 column chromatography (water→5% CH$_3$CN) to afford 0.26 g (y. 55%) of the titled compound as a colorless amorphous powdery product.

Specific optical rotation: $[\alpha]_D$ +42.7° (c=0.99, MeOH); Elemental Analysis for $C_{25}H_{37}N_7O_6 \cdot 1.1CF_3CO_2H \cdot 2H_2O$ (693.067): Calcd.: C, 47.14; H, 6.12; N, 14.15; Found : C, 47.30; H, 5.82; N, 14.40.

REFERENCE EXAMPLE 8

(S)-4-Benzyloxycarbonylaminoacetyl-3-{3-(5-t-butoxycarbonylaminopentanoylamino)propyl}-2-oxopiperazine-1-acetic acid In substantially the same manner as in Reference Example 7, the titled compound was synthesized by using 5-t-butoxyaminovaleric acid.

IR ν max cm$^{-1}$: 3370, 2940, 1650, 1533, 1455, 1254, 1170, 1050; NMR(CDCl$_3$) δ: 1.42(9H,s), 1.28–2.08(8H,m), 2.18(2H,t,J=7.0 Hz), 3.03(2H,t,J=6.8 Hz), 3.10–4.20(10H, m), 4.82–5.00(1H,m), 5.11(2H,s), 7.22–7.52(5H,m)

WORKING EXAMPLE 10

(S)-4-(4-Amidinobenzoylamino)acetyl-3-{3-(5-aminopentanoylamino)propyl}-2-oxopiperazine-1-acetic acid trifluoroacetate In substantially the same manner as in Working Example 9, the titled compound was synthesized by using (S)-4-benzyloxycarbonylaminoacetyl-3-{3-(5-t-butoxycarbonylaminopentanoylamino)propyl}-2-oxopiperazine-1-acetic acid.

Specific optical rotation: [α]$_D$ +46.0° (c=1.01, MeOH); Elemental Analysis for C$_{24}$H$_{35}$N$_7$O$_6$·CF$_3$CO$_2$H·2.5H$_2$O (676.646): Calcd.: C, 46.15; H, 6.11; N, 14.49; Found : C, 46.43; H, 6.15; N. 14.20.

REFERENCE EXAMPLE 9

(S)-4-Benzyloxycarbonylaminoacetyl-3-{3-(4-t-butoxycarbonylaminobutanoylamino)propyl}-2-oxopiperazine-1-acetic acid In substantially the same manner as in Reference Example 7, the titled compound was synthesized by using 4-t-butoxyaminobutyric acid.

IR ν max cm$^{-1}$: 3350, 2930, 1642, 1530, 1452, 1252, 1170, 1050; NMR(CDCl$_3$) δ: 1.42(9H,s), 1.30–2.10(4H,m), 1.73(2H,t,J=7.2 Hz), 2.18(2H,t,J=7.5 Hz), 3.04(2H,t,J=6.8 Hz), 3.10–4.20(10H,m), 4.83–4.97(1H,m), 5.11(2H,s), 7.22–7.50(5H,m)

WORKING EXAMPLE 11

(S)-4-(4-Amidinobenzoylamino)acetyl-3-{3-(4-aminobutanoylamino)propyl}-2-oxopiperazine-1-acetic acid trifluoroacetate In substantially the same manner as in Working Example 9, the titled compound was synthesized by using (S)-4-benzyloxycarbonylaminoacetyl-3-{3-(4-t-butoxycarbonylaminobutanoylamino)propyl}-2-oxopiperazine-1-acetic acid.

Specific optical rotation: [α]$_D$ +47.9° (c=1.00, H$_2$O); Elemental Analysis for C$_{23}$H$_{33}$N$_7$O$_6$·1.5CF$_3$CO$_2$H·2H$_2$O (710.623): Calcd.: C, 43.95; H, 5.46; N, 13.80; Found : C, 44.23; H, 5.63; N, 13.52.

WORKING EXAMPLE 12

(S,S)-4-{2-(4-Amidinobenzoylamino)-3-(4-methoxyphenyl)propionyl}-3-(4-guanidinobutyl)-2-oxopiperazine-1-acetic acid hydrochloride In 2.0 cc of trifluoroacetic acid was dissolved (S,S)-4-{2-benzyloxycarbonylamino-3-(4-methoxyphenyl)propionyl}-3-(4-t-butoxycarbonylaminobutyl)-2-oxopiperazine-1-acetic acid t-butyl ester (0.6 g, 0.86 mmol). The solution was stirred for one hour at room temperature, and the reaction mixture was concentrated under reduced pressure. An aqueous solution (5.6 cc) of the concentrate and sodium hydrogencarbonate (0.22 g, 2.57 mmol) was added to 5.6 cc of an aqueous solution of S-methylisothiourea sulfate (0.48 g, 1.71 mmol) and 2N NaOH (0.86 cc, 1.71 mmol). The mixture was stirred for 14 hours at room temperature. Resulting precipitates were collected by filtration, washed with water and dried. This solid product was dissolved in 5.8 cc of methanol, to which was added 0.12 g of 10% Pd-C, and the mixture was stirred for one hour under hydrogen atmosphere. The catalyst was filtered off, and the filtrate was concentrated under reduced pressure. The concentrate was purified by means of a CHP-20 column chromatography (water→5% CH$_3$CN→10% CH$_3$CN) to afford (S,S)-4-{2-amino-3-(4-methoxyphenyl)propionyl}-3-(4-guanidinobutyl)-2-oxopiperazine-1-acetic acid. This intermediate (0.16 g, 0.36 mmol) and sodium hydrogencarbonate (0.09 g, 1.07 mmol) were dissolved in a mixture of 3.2 cc of water and 1.6 cc of 1,4-dioxane. To the solution was added, under stirring at room temperature, 4-amidinobenzoylchloride hydrochloride (0.10 g, 0.46 mmol). The mixture was stirred for 1.5 hour, then, pH of the reaction mixture was adjusted to 4, followed by concentration under reduced pressure. The concentrate was purified by means of a CHP-20 column chromatography (water→5% CH$_3$CN) to afford 0.16 g (y. 27.3%) of the titled compound as a colorless amorphous powdery product.

Specific optical rotation: [α]$_D$ +62.7° (c=0.99, MeOH); Elemental Analysis for C$_{29}$H$_{38}$N$_8$O$_6$·HCl·3H$_2$O (685.176): Calcd.: C, 50.84; H, 6.62; N, 16.35; Found : C, 50.76; H, 6.47; N, 16.11.

WORKING EXAMPLE 13

(S)-4-(4-Amidinobenzoylamino)acetyl-3-{3-(4-guanidinobutanoylamino)propyl}-2-oxopiperazine-1-acetic acid hydrochloride In 6.6 cc of trifluoroacetic acid was dissolved (S)-4-benzyloxycarbonylaminoacetyl-3-{3-(4-t-butoxycarbonylaminobutanoylamino)propyl}-2-oxopiperazine-1-acetic acid (0.33 g, 0.56 mmol). The solution was stirred for one hour at room temperature, then the reaction mixture was concentrated under reduced pressure. An aqueous solution (3.3 cc) of the concentrate and sodium hydrogencarbonate (0.14 g, 1.68 mmol) was added to 3.3 cc of an aqueous solution of S-methyl isothiourea sulfate (0.93 g, 3.35 mmol) and 2N NaOH (1.68 cc, 3.35 mmol). The mixture was stirred for 14 hours at room temperature. The reaction mixture was concentrated under reduced pressure. The concentrate was purified by means of a CHP-20 column chromatography (H$_2$O→5% CH$_3$CN→10% CH$_3$CN→15% CH$_3$CN) to give (S)-[4-(benzyloxycarbonylamino)-acetyl-3-{3-(4-guanidino-butylamino)-propyl}-2-oxopiperazin-1-yl]-acetic acid. This intermediate was dissolved in 6.0 cc of methanol, to which was added 0.30 g of 10% Pd-C, and the mixture was stirred for one hour under hydrogen atmosphere. The catalyst was filtered off, and the filtrate was concentrated under reduced pressure. The concentrate and sodium hydrogencarbonate (0.19 g, 2.23 mmol) were dissolved in a mixture of 6.0 cc of water and 3.0 cc of 1,4-dioxane. To the solution was added, while stirring at room temperature, 4-amidinobenzoylchloride hydrochloride (0.16 g, 0.73 mmol). The mixture was stirred for one hour, whose pH was adjusted to 4 with 1N HCl, followed by concentration under reduced pressure. The concentrate was purified by means of a CHP-20 column chromatography (H$_2$O) to afford 0.09 g (y.24.7%) of the titled compound as a colorless amorphous powdery product.

Specific optical rotation: [α]$_D$ +48.4° (c=0.96, H$_2$O); Elemental Analysis for C$_{24}$H$_{35}$N$_9$O$_6$·2HCl·3.5H$_2$O (681.572): Calcd.: C, 42.29; H, 6.51; N, 18.50; Found : C, 42.34; H, 6.59; N, 18.28.

REFERENCE EXAMPLE 10

4-(N-Benzyloxycarbonyl)glycyl-1-t-butoxycarbonylmethyl-2-oxopiperazine-3-acetic acid In a mixture of 5 ml of water and 5 ml of methanol was dissolved 1.46 g of 4-(N-benzyloxycarbonyl)glycyl-1-t- butoxycarbonylmethyl-2-oxopiperazine-3-acetic acid methyl ester. To the solution was added 190 mg of lithium hydroxide monohydrate at 0° C. in the course of five minutes. The mixture was stirred for one hour at the same temperature, then for further one hour at room temperature. With a 5% aqueous solution of potassium hydrogensulfate, pH of the reaction mixture was adjusted to 7. The reaction mixture was concentrated under reduced pressure to eliminate methanol. To the concentrate was further added 5% potassium hydrogensulfate to adjust the pH to 3, which was subjected to extraction with ethyl acetate. The extract solution was dried over anhydrous magnesium sulfate, followed by concentration under reduced pressure to afford 1.1 g of the titled compound as a colorless oily product.

NMR(CDCl$_3$) δ: 1.452(9H,s), 2.80–4.65(10H,m), 5.10 (2H,s), 5.82(1H,m), 6.03(1H,m), 7.33(5H,s); IR ν max' cm$^{-1}$: 3000, 1730, 1660, 1465, 1370, 1230, 1160.

REFERENCE EXAMPLE 11

3-(4-Amidinophenyl)aminocarbonylmethyl-4-(N-benzyloxycarbonyl)glycyl-2-oxopiperazine-1-acetic acid t-butyl ester In 5 ml of pyridine were dissolved 820 mg of 4-(N-benzyloxycarbonyl)glycyl-1-t-butoxycarbonylmethyl-2-oxopiperazine-3-acetic acid produced in Reference Example 5 and 370 mg of 4-aminobenzamidine dihydrochloride. To the solution were added 370 mg of dicyclohexyl carbodiimide and 10 mg of 4-dimethylaminopyridine. The mixture was stirred for 24 hours at the same temperature. Insolubles were filtered off, and the filtrate was concentrated under reduced pressure to give a crude product, which was dissolved in a 1% aqueous solution of hydrochloric acid. The solution was subjected to a CHP-20 column chromatography. Fractions eluted with 5% acetonitrile-water were collected and freeze-dried to afford 550 mg of the titled compound as a colorless powdery product.

NMR(DMSO$_{d-6}$) δ: 1.42(9H,s), 2.83–4.44(13H,m), 5.02 (2H,s), 7.34(5H,s), 7.78–7.82(4H,m), 9.03–9.25(3H,m); IR ν max' cm$^{-1}$: 3325, 1730, 1680, 1640, 1480, 1365, 1260, 1155.

WORKING EXAMPLE 14

(S)-4-[N-(4-Amidinobenzoylamino)acetyl]-3-(4-amidinophenyl)aminocarbonylmethyl-2-oxopiperazine-1-acetic acid In 15 ml of methanol was dissolved 930 mg of 3-(4-amidinophenyl)aminocarbonylmethyl-4-(N-benzyloxycarbonyl)glycyl-2-oxopiperazine-1-acetic acid t-butyl ester produced in Reference Example 6. To the solution was added 100 mg of 10% Pd-C, and the mixture was stirred for one hour under hydrogen atmosphere. The catalyst was filtered off, and the filtrate was concentrated under reduced pressure to give an oily substance. The oily substance and 350 mg of sodium hydrogencarbonate were dissolved in a mixture of 25 ml of water and 15 ml of dioxane. To the solution was added, while stirring vigorously at room temperature, 307 mg of 4-amidinobenzoic acid in the course of 5 minutes. The reaction mixture was concentrated to give a crude product, which was dissolved in 5 ml of dichloromethane. To the solution was added 5 ml of trifluoroacetic acid at room temperature, and the mixture was stirred for one hour. The reaction mixture was concentrated under reduced pressure to give a crude product, which was purified by means of a CHP-20 column chromatography to afford 490 mg of the titled compound as a colorless powdery product.

Specific optical rotation: $[\alpha]_D^{23}$ +57.5° (c=0.9, H$_2$O); Elemental Analysis for C$_{25}$H$_{28}$N$_8$O$_6$·CF$_3$CO$_2$H·2.7H$_2$O: Calcd.: C, 46.41; H, 4.96; N, 16.04; Found : C, 46.56; H, 4.80; N, 15.84.

WORKING EXAMPLE 15

(S)-4-(4-Guanidinobenzoylamino)acetyl-3-[3-(4-guanidinobenzoylamino)]propyl-2-oxopiperazine-1-acetic acid hydrochloride In 4.9 ml of trifluoroacetic acid was dissolved 0.7 g of (S)-4-benzyloxycarbonylaminoacetyl-3-(3-t-butoxycarbonylamino)propyl-2-oxopiperazine-1-acetic acid t-butyl ester produced in Reference Example 2. The solution was stirred for one hour at room temperature. The reaction mixture was concentrated under reduced pressure, and then subjected to azeotropic distillation with toluene several times. The residue was subjected to a CHP-20 (Mitsubishi Chemical Industries, Ltd.) column chromatography. Fractions eluted with 20% acetonitrile/water were combined and concentrated to give (S)-4-benzyloxycarbonylaminoacetyl-3-(3-amino)propyl-2-ox-opiperazine-1-acetic acid as a crude product. This crude product was dissolved in 12.0 ml of methanol, to which was added 250 mg of 10% Pd-C, and then the mixture was stirred for one hour under hydrogen atmosphere. The catalyst was filtered off, and the filtrate was concentrated under reduced pressure. The concentrate and 836 mg of sodium hydrogencarbonate were dissolved in a mixture of 7.0 ml of 1,4-dioxane and 14.0 ml of water. To the solution was added, while stirring at room temperature, 1.27 g of 4-guanidinobenzoic acid N-hydroxy-5-norbornene-2,3-dicarboxylic acid imidoester hydrochloride. The mixture was stirred for one hour, then pH of the reaction mixture was adjusted to 3 to 4 with 1N hydrochloric acid, followed by concentration under reduced pressure. The concentrate was subjected to CHP-20 column chromatography (eluted with 5% CH$_3$CN/H$_2$O). Relevant fractions were combined and freeze-dried to afford 0.48 g of the titled compound as a colorless amorphous powdery product.

Specific optical rotation: $[\alpha]_D^{20}$ +56.3° (c=1.017, H$_2$O); Elemental Analysis for C$_{27}$H$_{34}$N$_{10}$O$_6$·1.0HCl·3.5H$_2$O: Calcd.: C, 46.72; H, 6.10; N, 20.18; Found : C, 46.56; H, 6.17; N, 20.05.

REFERENCE EXAMPLE 12

(S)-3-(2-t-Butoxycarbonylamino)ethyl-2-oxopiperazine-1-acetic acid t-butyl ester oxalate In 200 ml of acetonitrile were dissolved 26 g of (S)-N$^2$-benzyloxycarbonyl-N$^4$-t-butoxycarbonyl-2,4-diaminobutanoic acid and 15.5 g of N-(2,2-dimethoxyethyl) glycine t-butyl ester. To the solution was added, while stirring at room temperature, 19 g of 1-ethyl-3-(3-dimethylaminopropyl)carbodiimide hydrochloride. The mixture was stirred for further two hours at the same temperature. The reaction mixture was then concentrated to leave an oily substance, which was dissolved in ethyl acetate. The solution was washed with a 5% aqueous solution of potassium hydrogensulfate and, then, with a saturated aqueous solution of sodium hydrogencarbonate. The solution was dried over anhydrous magnesium sulfate and concentrated under reduced pressure. The concentrate was dissolved in 500 ml of toluene, to which was added 1.4 g of p-toluenesulfonic acid. The mixture was stirred for 3 hours at 70° C., which was cooled to room temperature and washed with a saturated aqueous solution of sodium hydrogencarbonate. The mixture was dried over anhydrous magnesium sulfate, which was then concentrated under reduced pressure. The concentrate was dissolved in 500 ml of methanol, to which was added 10 g of 10% Pd-C. The mixture was stirred for 10 hours at room temperature under hydrogen atmosphere. The catalyst was filtered off. To the filtrate was added 6.4 g of oxalic acid, and the mixture was concentrated under reduced pressure to give a crude crystalline product. This crude product was recrystallized from methanol/ethyl acetate to afford 9.5 g of the titled compound as colorless crystals.

m.p.: 165–169° C.; Elemental Analysis for $C_{17}H_{31}N_5O_5 \cdot (CO_2H)_2$: Calcd.: C, 51.00; H, 7.43; N, 9.39; Found : C, 50.78; H, 7.59; N, 9.14.

REFERENCE EXAMPLE 13
(S)-4-(Benzyloxycarbonylamino)acetyl-3-(2-t-butoxycarbonylamino)ethyl-2-oxopiperazine-1-acetic acid t-butyl ester In 20 ml of dichloromethane was suspended 900 mg of (S)-3-(2-t-butoxycarbonylaminoethyl)-2-oxopiperazine-1-acetic acid t-butyl ester oxalate produced in Reference Example 12. To the suspension was added 20 ml of a saturated aqueous solution of sodium hydrogencarbonate, and the mixture was vigorously stirred for 10 minutes. The organic layer was separated and dried over anhydrous magnesium sulfate, to which were added 420 mg of N-benzyloxycarbonyl glycine and 500 mg of 1-ethyl-3-(3-dimethylaminopropyl)carbodiimide hydrochloride. The mixture was stirred for 2 hours at room temperature. The reaction mixture was concentrated under reduced pressure. The concentrate was dissolved in ethyl acetate, which was washed with 5% aqueous solution of potassium hydrogensulfate and a saturated aqueous solution of sodium hydrogencarbonate. The concentrate was dried over anhydrous magnesium sulfate, which was concentrated under reduced pressure. The concentrate was purified by means of a silica gel chromatography (eluent: ethyl acetate-hexane=3:1) to afford 1.05 g of the titled compound as a colorless oily product.

IR ν max cm$^{-1}$: 3450, 1705, 1655, 1640, 1500, 1450, 1360, 1240, 1160; NMR(CDCl$_3$) δ: 1.43(9H,s), 1.46(9H,s), 2.05–2.33(1H,m), 2.73–2.95(1H,m), 3.15–4.20(10H,m), 5.05(1H,dd,J=3 Hz), 5.13(2H,s), 5.30(1H,brs), 5.83(1H, brs), 7.36(5H,s).

WORKING EXAMPLE 16
(S)-4-(4-Amidinobenzoylamino)acetyl-3-[2-(4-guanidinobenzoylamino)]ethyl-2-oxopiperazine-1-acetic acid hydrochloride In 5 ml of trifluoroacetic acid was dissolved 550 mg of (S)-4-(N-benzyloxycarbonylamino)acetyl-3-(2-t-butoxycarbonylamino)ethyl-2-oxopiperazine-1-acetic acid t-butyl ester produced in Reference Example 13. The solution was stirred for one hour at room temperature. The reaction mixture was concentrated to give an oily substance. This oily substance and 400 mg of sodium hydrogencarbonate were dissolved in a mixture of 25 ml of water and 25 ml of dioxane. To the solution was added, while stirring at room temperature, 250 mg of 4-guanidinobenzoyl chloride hydrochloride. The reaction mixture was adjusted to pH 7 with 1N HCl, to which was added 100 mg of 10% Pd-C. The mixture was stirred for one hour under hydrogen atmosphere. The catalyst was filtered off. To the filtrate were added 30 ml of dioxane and 400 mg of sodium hydrogencarbonate. To the mixture was added, while stirring vigorously, 230 mg of 4-amidinobenzoic acid hydrochloride. The reaction mixture was adjusted to pH 3 with 1N HCl, which was concentrated under reduced pressure to half of its initial volume. The concentrate was purified by means of a CHP-20 column (5% acetonitrile/water) to afford 250 mg of the titled compound as a colorless amorphous solid product.

Specific optical rotation: $[\alpha]_D^{20}$ +26.112° (c=0.450, MeOH); Elemental Analysis for $C_{26}H_{31}N_9O_6 \cdot HCl \cdot 5H_2O$: Calcd.: C, 45.12; H, 6.12; N, 18.21; Found : C, 45.61; H, 6.06; N, 18.22.

REFERENCE EXAMPLE 14
(S)-4-Benzyloxycarbonylaminoacetyl-3-t-butoxycarbonylaminomethyl-2-oxopiperazine-1-acetic acid t-butyl ester In substantially the same manner as in Reference Example 1 and 2, the titled compound was produced as a colorless oily product by using (S)-$N^2$-benzyloxycarbonyl-$N^3$-t-butoxycarbonyl-2,3-diaminopropanoic acid.

H$^1$-NMR(CDCl$_3$) δ: 1.38(9H,s), 1.47(9H,s), 3.19–4.20 (10H,m), 4.90–5.05(2H,m), 5.13(2H,s), 5.82(1H,brs), 7.36 (5H,s).

WORKING EXAMPLE 17
(S)-4-(4-Amidinobenzoylamino)acetyl-3-aminomethyl-2-oxopiperazine-1-acetic acid dihydrochloride The titled compound was produced as a colorless amorphous powdery product by subjecting (S)-4-benzyloxycarbonylaminoacetyl-3-t-butoxycarbonylaminomethyl-2-oxopiperazine-1-acetic acid t-butyl ester produced in Reference Example 14 to substantially the same procedure as in Working Example 1.

Specific optical rotation: $[\alpha]_D^{20}$ +44.9° (c=0.655, MeOH); Elemental Analysis for $C_{17}H_{22}N_6O_5 \cdot 2HCl \cdot 4H_2O$: Calcd.: C, 38.14; H, 6.02; N, 15.70; Found : C, 38.11; H, 5.65; N, 15.70.

WORKING EXAMPLE 18
(S)-4-(4-Amidinobenzoylamino)acetyl-3-(4-amidinobenzoylamino)methyl-2-oxopiperazine-1-acetic acid hydrochloride (S)-4-(4-Amidinobenzoylamino)acetyl-3-aminomethyl-2-oxopiperazine-1-acetic acid dihydrochloride produced in Working Example 17 was subjected to substantially the same procedure as in Working Example 2 to afford the titled compound as a colorless amorphous powdery product.

Specific optical rotation: $[\alpha]_D^{20}$ +60.2° (c=0.535, MeOH); Elemental Analysis for $C_{25}H_{28}N_8O_6 \cdot HCl \cdot 3H_2O$: Calcd.: C, 47.89; H, 5.63; N, 17.87; Found : C, 47.63; H. 5.36; N, 17.81.

WORKING EXAMPLE 19
(S)-4-(4-Amidinobenzoylamino)acetyl-3-[2-(4-amidinobenzoylamino)]ethyl-2-oxopiperazine-1-acetic acid trifluoroacetate (S)-4-(Benzyloxycarbonylamino)acetyl-3-(2-t-butoxycarbonylamino)ethyl-2-oxopiperazine-1-acetic acid t-butyl ester produced in Reference Example 13 was subjected to substantially the same procedure as in Working Example 1 and 2 to afford the titled compound as a colorless amorphous powdery product.

Specific optical rotation: $[\alpha]_D^{20}$ +30.299° (c=0.470, H$_2$O); Elemental Analysis for $C_{26}H_{30}N_8O_6 \cdot CF_3CO_2H \cdot 3H_2O$: Calcd.: C, 46.80; H, 5.19; N, 15.59; Found : C, 46.67; H, 4.99; N, 15.39.

WORKING EXAMPLE 20
(S)-4-(4-Guanidinobenzoylamino)acetyl-3-[2-(4-guanidinobenzoylamino)]ethyl-2-oxopiperazine-1-acetic acid trifluoroacetate (S)-4-(benzyloxycarbonylamino)acetyl-3-(2-t-butoxycarbonylamino)ethyl-2-oxopiperazine-1-acetic acid t-butyl ester produced in Reference Example 13 was subjected to substantially the same procedure as in Working Example 15 to afford the titled compound as a colorless amorphous powdery product.

Specific optical rotation: $[\alpha]_D^{20}$ +35.207° (c=0.650, H$_2$O); Elemental Analysis for C$_{26}$H$_{32}$N$_{10}$O$_6$.CF$_3$CO$_2$H.3H$_2$O: Calcd.: C, 44.92; H, 5.25; N, 18.71; Found : C, 44.95; H, 5.54; N, 18.69.

WORKING EXAMPLE 21

(R)-4-(4-Amidinobenzoylamino)acetyl-3-(3-amino)propyl-2-oxopiperazine-1-acetic acid trifluoroacetic acid Z—D—Orn(Boc)—OH was subjected to substantially the same procedure as in Reference Example 1, 2 and Working Example 1 to afford the titled compound as a colorless amorphous powdery product.

Specific optical rotation: $[\alpha]_D^{20}$ −35.6° (c=0.519, MeOH); Elemental Analysis for C$_{19}$H$_{26}$N$_6$O$_5$.2CF$_3$CO$_2$H.1.5H$_2$O: Calcd.: C, 41.02; H, 4.64; N, 12.48; Found : C, 41.16; H, 4.47; N, 12.60.

WORKING EXAMPLE 22

(R)-4-(4-Amidinobenzoylamino)acetyl-3-[3-(4-amidinobenzoylamino)]propyl-2-oxopiperazine-1-acetic acid trifluoroacetate (R)-4-(4-Amidinobenzoylamino)acetyl-3-(3-amino)-propyl-2-oxopiperazine-1-acetic acid trifluoroacetic acid produced in Working Example 21 was subjected to substantially the same procedure as in Working Example 2 to afford the titled compound as a colorless amorphous powdery product.

Specific optical rotation: $[\alpha]_D^{20}$ −41.6° (c=0.495, MeOH); Elemental Analysis for C$_{27}$H$_{32}$N$_8$O$_6$.CF$_3$CO$_2$H.4H$_2$O: Calcd.: C, 46.40; H, 5.51; N, 14.93; Found : C, 46.66; H, 5.20; N, 14.90.

WORKING EXAMPLE 23

(S)-4-(4-Amidinobenzoylamino)acetyl-3-[3-(4-guanidinobenzoylamino)]propyl-2-oxopiperazine-1-acetic acid trifluoroacetate (S)-4-(Benzyloxycarbonylamino)acetyl-3-(3-t-butoxycarbonylamino)propyl-2-oxopiperazine-1-acetic acid t-butyl ester produced in Reference Example 2 was subjected to substantially the same procedure as in Working Example 18 to afford the titled compound as a colorless amorphous powdery product.

Specific optical rotation: $[\alpha]_D^{20}$ +48.6° (c=1.017, H$_2$O); Elemental Analysis for C$_{27}$H$_{33}$N$_9$O$_6$.1.1CF$_3$CO$_2$H.1.5H$_2$O: Calcd.: C, 48.00; H, 5.30; N, 16.97; Found : C, 47.91; H, 5.11; N, 17.22.

WORKING EXAMPLE 24

(S)-4-(4-Amidinobenzoylamino)acetyl-3-(4-amidinophenylaminocarbonyl)ethyl-2-oxopiperazine-1-acetic acid trifluoroacetate (S) -4-Benzyloxycarbonylaminoacetyl-1-t-butoxycarbonylmethyl-2-oxopiperazine-3-propanoic acid methyl ester was subjected to substantially the same procedure as in Reference Example 10, 11 and Working Example 14 to afford the titled compound as a colorless amorphous powdery product.

Specific optical rotation: $[\alpha]_D^{20}$ +59.625° (c=0.360, H$_2$O); Elemental Analysis for C$_{26}$H$_{30}$N$_8$O$_6$.CF$_3$CO$_2$H.4H$_2$O: Calcd.: C, 45.65; H, 5.34; N, 15.21; Found : C, 45.70; H, 5.10; N, 14.91.

WORKING EXAMPLE 25

(S)-4-(4-Amidinobenzoylamino)acetyl-3-(4-amidinomethylbenzoylamino)methyl-2-oxopiperazine-1-acetic acid dihydrochloride (S)-4-Benzyloxycarbonylaminoacetyl-3-t-butoxycarbonylaminomethyl-2-oxopiperazine-1-acetic acid t-butyl ester produced in Reference Example 14, N-hydroxysuccinimide active ester of 4-amidinomethyl benzoic acid hydrochloride and 4-amidinobenzoyl chloride hydrochloride were subjected to substantially the same procedure as in Working Example 16 to afford the titled compound as a colorless amorphous powdery product.

Elemental Analysis for C$_{26}$H$_{30}$N$_8$O$_6$.2HCl.4.5H$_2$O: Calcd.: C, 44.32; H, 5.87; N, 15.90; Found : C, 44.23; H, 5.74; N, 15.88.

WORKING EXAMPLE 26

(S)-4-(4-Amidinobenzoylamino)acetyl-3-(4-guanidinomethylbenzoylamino)methyl-2-oxopiperazine-1-acetic acid dihydrochloride (S)-4-Benzyloxycarbonylaminoacetyl-3-t-butoxycarbonylaminomethyl-2-oxopiperazine-1-acetic acid t-butyl ester produced in reference Example 14, N-hydroxysuccinimide active ester of 4-guanidinomethyl benzoic acid hydrochloride and 4-amidinobenzoyl chloride hydrochloride were subjected to substantially the same procedure as in Working Example 16 to afford the titled compound as a colorless amorphous powdery product.

Specific optical rotation: $[\alpha]_D^{20}$ +47.2° (c=0.553, H$_2$O); Elemental Analysis for C$_{26}$H$_{31}$N$_9$O$_6$.2HCl.3H$_2$O: Calcd.: C, 45.09; H, 5.67; N, 18.20; Found : C, 45.32; H, 5.55; N, 18.10.

WORKING EXAMPLE 27

(S,S)-4-[2-(4-Amidinobenzoylamino)-3-(4-methoxyphenyl)]propionyl-3-[3-(6-aminohexanoylamino)]propyl-2-oxopiperazine-1-acetic acid trifluoroacetate (S,S)-4-[2-Benzyloxycarbonylamino-3-(4-methoxyphenyl)]propionyl-3-(3-t-butoxycarbonylamino)propyl-2-oxopiperazine-1-acetic acid t-butyl ester produced in Reference Example 5 was subjected to substantially the same procedure as in Reference Example 7 and Working Example 9 to afford the titled compound as a colorless amorphous powdery product.

Specific optical rotation: $[\alpha]_D^{20}$ +57.3° (c=0.678, MeOH); Elemental Analysis for C$_{33}$H$_{45}$N$_7$O$_7$.CF$_3$CO$_2$H.2.5H$_2$O: Calcd.: C, 51.85; H, 6.34; N, 12.09; Found : C, 52.02; H, 6.25; N, 12.04.

WORKING EXAMPLE 28

(S,S)-4-[2-(4-Amidinobenzoylamino)-3-(4-methoxyphenyl)]propionyl-3-[4-(2-aminoacetylamino)]butyl-2-oxopiperazine-1-acetic acid trifluoroacetate (S,S)-4-[2-Benzyloxycarbonylamino-3-(4-methoxyphenyl)]propionyl-3-(4-t-butoxycarbonylamino)butyl-2-oxopiperazine-1-acetic acid t-butyl ester produced in Reference Example 6 and N-t-butoxycarbonyl glycine were subjected to substantially the same procedure as in Reference Example 7 and Working Example 9 to afford the titled compound as a colorless amorphous powdery product.

Specific optical rotation: $[\alpha]_D^{20}$ +59.8° (c=0.644, MeOH); Elemental Analysis for C$_{30}$H$_{39}$N$_7$O$_7$.CF$_3$CO$_2$H.2.5H$_2$O: Calcd.: C, 50.00; H, 5.90; N, 12.75; Found : C, 49.95; H, 5.72; N, 12.87.

REFERENCE EXAMPLE 15

4-(Amino-hydroxyimino)benzoic acid methyl ester

In 200 ml of methanol were dissolved 16.5 g of 4-cyanobenzoic acid methyl ester and 7.2 g of hydroxylamine hydrochloride. To the solution was added 8.82 g of sodium hydrogencarbonate at room temperature. The mixture was heated for 3 hours under reflux. The reaction mixture was cooled, to which was added 400 ml of water. Resulting crystalline precipitate was collected by filtration, which was washed with water and ether, followed by drying under reduced pressure to afford 16.1 g of the titled compound as colorless needles.

m.p.: 170–172° C.; Elemental Analysis for $C_9H_{10}N_2O_3$: Calcd.: C, 55.67; H, 5.19; N, 14.43; Found : C, 55.57; H, 5.22; N, 14.39.

REFERENCE EXAMPLE 16
4-(2,5-Dihydro-5-oxo-1,2,4-oxadiazol-3-yl)benzoic acid

In 30 ml of dioxane were suspended 5.83 g of 4-(amino-hydroxyimino)benzoic acid methyl ester produced in Reference Example 15 and 6 g of N,N'-carbonyldiimidazole, which was stirred for 30 minutes at 110° C. The reaction mixture was concentrated to dryness. The concentrate was dissolved in water, which was adjusted to pH 4 with acetic acid. Then, resulting crystals were collected by filtration and dissolved in 60 ml of 2N NaOH. The solution was stirred overnight at room temperature. To the reaction mixture was added acetic acid to adjust its pH to 4. Resulting crystalline precipitate was collected by filtration and washed with water, followed by recrystallization from dimethylformamide/ethyl acetate to afford 4.3 g of the titled compound as a colorless crystalline product.

m.p.: not lower than 300° C.; Elemental Analysis for $C_9H_6N_2O_4$: Calcd.: C, 52.44; H, 2.93; N, 13.59; Found : C, 52.14; H, 3.29; N, 13.89.

WORKING EXAMPLE 29
(S)-4-[4-(2,5-Dihydro-5-oxo-1,2,4-oxadiazol-3-yl) benzoylamino]acetyl-3-{3-[4-(2,5-dihydro-5-oxo-1,2,4-oxadiazol-3-yl)benzoylamino]}propyl-2-oxopiperazine-1-acetic acid ammonium salt In 50 ml of methanol was dissolved 1 g of (S)-4-(benzyloxycarbonylamino)acetyl-3-(3-t-butoxycarbonylamino)propyl-2-oxopiperazine-1-acetic acid t-butyl ester produced in Reference Example 2. To the solution was added 0.2 g of 10% Pd-C, and the mixture was stirred for one hour under hydrogen streams. The catalyst was filtered off, and the filtrate was concentrated under reduced pressure. To the concentrate was added 4-(2,5-dihydro-5-oxo-1,2,4-oxadiazol-3-yl)benzoic acid produced in Reference Example 16. The mixture was dissolved in 20 ml of dimethylformamide. To the solution was added 0.36 g of 1-ethyl-3-(3-dimethylaminopropyl) carbodiimide hydrochloride, and the mixture was stirred for 3 hours at room temperature. The reaction mixture was concentrated under reduced pressure. The concentrate was purified by means of a silica gel column chromatography (eluted with ethyl acetate—25% methanol/ethyl acetate) to give an oily product. This product was dissolved in 6 ml of trifluoroacetic acid, which was stirred for 2 hours at room temperature. The reaction mixture was concentrated under reduced pressure. The concentrate was dissolved in 8 ml of dimethylformamide, to which was added 1.25 ml of triethylamine. To the mixture was added a dimethylformamide solution of the active ester prepared from 0.33 g of 4-(2,5-dihydro-5-oxo-1,2,4-oxadiazol-3-yl) benzoic acid, 0.23 g of N-hydroxysuccinimide and 0.42 g of dicyclohexyl carbodiimide. The mixture was stirred for 3 hours at room temperature. Insolubles were filtered off, and the filtrate was concentrated under reduced pressure. The concentrate was dissolved in water, to which was added acetic acid to adjust the pH to 4. Then, resulting precipitate was collected by filtration, which was dissolved in water. To the solution was added ammoniacal water to adjust the pH to 8, which was subjected to an XAD-2 column. Fractions eluted with 10% acetonitrile/water were combined and freeze-dried to afford 0.114 g of the titled compound as a colorless amorphous powdery product.

Specific optical rotation: $[\alpha]_D^{20}$ +49.9° (c=0.522, MeOH); Elemental Analysis for $C_{29}H_{31}N_9O_{10} \cdot 3.5H_2O$: Calcd.: C, 47.80; H, 5.26; N, 17.30; Found : C, 47.87; H, 5.12; N, 17.81.

REFERENCE EXAMPLE 17
4-Cyanobenzoic acid t-butyl ester

In 612 ml of methylene chloride were suspended 45.0 g of 4-cyanobenzoic acid and 3.1 ml of conc. sulfuric acid. To the suspension was added, while stirring at 0° C., 310 ml of isobutene. The mixture was stirred for 13 days. The reaction mixture was neutralized with a saturated aqueous solution of sodium hydrogencarbonate, which was subjected to extraction with ethyl acetate. The organic layer was concentrated under reduced pressure. Resulting precipitate was collected by filtration and washed with hexane. The filtrate and the washing were combined, which was concentrated under reduced pressure. The concentrate was purified by means of a silica gel chromatography (hexane/ethyl acetate=10/1), followed by crystallization from methylene chloride/petroleum ether to afford 43.1 g of the titled compound as a white crystalline product.

NMR(CDCl$_3$) δ: 1.61(9H,s), 7.72(2H,d,J=8.8 Hz), 8.08 (2H,d,J=8.8 Hz)

REFERENCE EXAMPLE 18
4-(Amino-hydroxyimino)methyl-benzoic acid t-butyl ester

In a mixture of 21.2 ml of t-butanol and 2.1 ml of water were dissolved 4.3 g of 4-cyanobenzoic t-butyl ester, 1.84 g of hydroxylamine hydrochloride and 2.31 g of sodium hydrogencarbonate. The solution was stirred for 2 hours at 80° C. To the reaction mixture was added water, and the mixture was subjected to extraction with ethyl acetate. The organic layer was concentrated under reduced pressure. The concentrate was purified by means of a silica gel column chromatography (hexane/ethyl acetate=1/1), followed by crystallization from hexane to afford 4.41 g of the titled compound as colorless needles.

m.p.: 153–155° C.; Elemental Analysis for $C_{12}H_{16}N_2O_3$: Calcd.: C, 61.00; H, 6.83; N, 11.86; Found : C, 61.03; H, 6.70; N, 11.90.

REFERENCE EXAMPLE 19
4-(Amino-methoxycarbonyloxyiminomethyl)benzoic acid t-butyl ester In 8.46 ml of 1,4-dioxane were dissolved 1.0 g of 4-(amino-hydroxyimino)methyl-benzoic acid t-butyl ester and 292 mg of potassium carbonate. To the solution was added, while stirring at 0° C., 343 μL of methyl chloroformate. The mixture was stirred for one hour at room temperature. To the reaction mixture was added water. Resulting crystalline precipitate was collected by filtration and washed with water to afford 1.22 g of the titled compound as a white crystalline product.

m.p.: 157–159° C.; Elemental Analysis for $C_{14}H_{18}N_2O_5$: Calcd.: C, 57.14; H, 6.16; N, 9.52; Found : C, 56.98; H, 6.21; N, 9.30.

REFERENCE EXAMPLE 20
4-(Amino-methoxycarbonyloxyiminomethyl)benzoic acid trifluoroacetate In 4.0 ml of trifluoroacetic acid was dissolved 1.0 g of 4-(amino-methoxycarbonyloxyiminomethyl)benzoic acid t-butyl ester. The solution was stirred for one hour at room temperature. The reaction mixture was concentrated under reduced pressure. The concentrate was subjected to azeotropic distillation with toluene to afford 0.80 g of the titled compound as a colorless amorphous powdery product.

Elemental Analysis for $C_{10}H_{10}N_2O_5 \cdot CF_3CO_2H$ (352.2233): Calcd.: C, 40.92; H, 3.15; N, 7.95; Found : C, 41.21; H, 2.98; N. 7.96.

WORKING EXAMPLE 30

(S)-4-[4-(Amino-methoxycarbonyloxyiminomethyl) benzoylamino]acetyl-3-{3-[4-(amino-methoxycarbonyloxyiminomethyl)-benzoylamino]}propyl-2-oxopiperazine-1-acetic acid (S)-4-(Benzyloxycarbonylamino)acetyl-3-(3-t-butoxycarbonylamino)propyl-2-oxopiperazine-1-acetic acid t-butyl ester produced in Reference Example 2 and 4-(amino-methoxycarbonyloxyiminomethyl)benzoic acid trifluoroacetate produced in Reference Example 20 were subjected to substantially the same procedure as in Working Example 15 to afford the titled compound as a colorless amorphous powdery product.

Specific optical rotation: $[\alpha]_D^{20}$ +50.5° (c=1.018, MeOH); Elemental Analysis for $C_{31}H_{36}N_8O_{12} \cdot 2H_2O$: Calcd.: C, 49.73; H, 5.38; N, 14.97; Found : C, 49.54; H, 5.19; N, 14.87.

WORKING EXAMPLE 31

(S)-4-(4-Amidinobenzoylamino)acetyl-3-{3-[4-(amino-methxoycarbonyloxyiminomethyl)benzoylamino]}propyl-2-oxopiperazine-1-acetic acid hydrochloride (S)-4-(Benzyloxycarbonylamino)acetyl-3-(3-t-butoxycarbonylamino)propyl-2-oxopiperazine-1-acetic acid t-butyl ester produced in Reference Example 2, 4-(amino-methoxycarbonyloxyiminomethyl)benzoic acid trifluoroacetate produced in Reference Example 20 and 4-amidinobenzoic acid were subjected to substantially the same procedure as in Working Example 16 to afford the titled compound as a colorless amorphous powdery product.

Specific optical rotation: $[\alpha]_D^{20}$ +47.5° (c=1.00, $H_2O$); Elemental Analysis for $C_{29}H_{34}N_8O_9 \cdot HCl \cdot 3H_2O$: Calcd.: C, 47.77; H, 5.67; N, 15.37; Found : C, 47.51; H, 5.68; N, 15.27.

REFERENCE EXAMPLE 21

(S)-3-[3-(4-Amidinobenzoylamino)]propyl-4-benzyloxycarbonylaminoacetyl-2-oxopiperazine-1-acetic acid In 6.8 ml of trifluoroacetic acid was dissolved 1.35 g of (S)-4-benzyloxycarbonylaminoacetyl-3-(3-t-butoxycarbonylaminopropyl)-2-oxopiperazine-1-acetic acid t-butyl ester produced in Reference Example 2. The solution was stirred for one hour at room temperature, which was then concentrated under reduced pressure. The concentrate was dissolved in a mixture of 20 ml of water and 10 ml of dioxane. To the solution were added 806 mg of sodium hydrogencarbonate and then 683 mg of 4-amidinobenzoyl chloride hydrochloride. The mixture was stirred vigorously for 30 minutes. The reaction mixture was concentrated to give a crude product, which was purified by means of a CHP-20 column (eluted with 20% acetonitrile/water) to afford 1.0 g of the titled compound as a colorless amorphous powdery product.

Specific optical rotation: $[\alpha]_D^{20}$ +106.6° (c=0.478, 1.1N HCl); Elemental Analysis for $C_{27}H_{32}N_6O_7 \cdot 2H_2O$: Calcd.: C, 55.09; H, 6.16; N, 14.28; Found : C, 55.36; H, 6.10; N, 14.35.

WORKING EXAMPLE 32

(S)-4-[4-(2-Aminoethyl)benzoylamino]acetyl-3-[3-(4-amidinobenzoylamino))propyl-2-oxopiperazine-1-acetic acid trifluoroacetate In 20 ml of methanol was dissolved 300 mg of (S)-3-[3-(4-amidinobenzoylamino)]propyl-4-benzyloxycarbonylaminoacetyl-2-oxopiperazine-1-acetic acid produced in Reference Example 21. To the solution was added 120 mg of 10% Pd-C, and the mixture was stirred for one hour at room temperature in hydrogen streams. The catalyst was filtered off, and the filtrate was concentrated under reduced pressure to give an oily product, which was dissolved in 5 ml of dimethylformamide. To the solution was added 5 ml of activated-ester solution in dimethylformamide which was prepared from 94 mg of N-hydroxysuccinimide and 173 mg of 4-(2-t-butoxycarbonylaminoethyl)benzoic acid in the presence of 167 mg of 1-ethyl-3-(3-dimethylaminopropyl)carbodiimide hydrochloride. The mixture was stirred for two hours at room temperature. The reaction mixture was concentrated to give an oily product, which was dissolved in 7 ml of trifluoroacetic acid. The solution was stirred for one hour at room temperature. The reaction mixture was concentrated under reduced pressure to give a crude product, which was purified by means of a CHP-20 column (eluted with 10% acetonitrile/water) to afford 110 mg of the titled compound as a colorless amorphous powdery product.

Specific optical rotation: $[\alpha]_D^{20}$ +41.7° (c=1.018, MeOH); Elemental Analysis for $C_{28}H_{35}N_7O_6 \cdot 1.1CF_3CO_2H \cdot 4H_2O$: Calcd.: C, 47.53; H, 5.82; N, 12.85; Found: C, 47.64; H, 5.60; N, 12.72.

WORKING EXAMPLE 33

(S)-4-(4-Amidinobenzoylamino)acetyl-3-[3-(4-amidinobenzoylamino)]propyl-2-oxopiperazine-1-acetic acid hydrochloride In 5 ml of 0.5N hydrochloric acid was dissolved 1 g of (S)-4-(4-amidinobenzoylamino)acetyl-3-[3-(4-amidinobenzoylamino)]propyl-2-oxopiperazine-1-acetic acid trifluoroacetate produced in Working Example 2. The solution was stirred for 5 minutes at 0° C., which was allowed to be adsorbed on a CHP-20 column. The column was washed with water until the eluate showed neutral pH. The column was then subjected to elution with 10% acetonitrile/water. Fractions of the eluate were combined and freeze-dried to afford 0.7 g of the titled compound as a colorless amorphous powdery product.

Specific optical rotation: +51.3° (c=1.018, $H_2O$); Elemental Analysis for $C_{27}H_{32}N_8O_6 \cdot HCl \cdot 5H_2O$: Calcd.: C, 46.92; H, 6.27; N, 16.21; Found : C, 47.13; H, 6.14; N, 16.23.

REFERENCE EXAMPLE 22

N-(4-t-butoxycarbonylphenyl)-N'-ethoxycarbonyl thiourea

In 150 ml of isopropyl ether was dissolved 13.51 g of 4-amino-benzoic acid t-butyl ester. To the solution was added, while stirring at room temperature, 9.83 g of ethoxycarbonyl isothiocyanate. The mixture was stirred for two hours, then the resulting crystalline precipitate was collected by filtration, followed by recrystallization from isopropyl ether to give 21.83 g of the title compound as colorless needles.

m.p.: 119–120° C.; Elemental Analysis for $C_{15}H_{20}N_2O_4S$: Calcd.: C, 55.54; H, 6.21; N, 8.64; Found : C, 55.56; H, 6.06; N, 8.65.

REFERENCE EXAMPLE 23

N-(4-butoxycarbonylphenyl)-N'-ethoxycarbonyl-S-methyl isothiourea

In 80 ml of tetrahydrofuran was dissolved 21.7 g of N-(4-t-butoxycarbonylphenyl)-N'-ethoxycarbonyl thiourea produced in Reference Example 22. To the solution was added, while stirring on an ice-bath, 2.68 g of 60% oil sodium hydride which was previously washed with hexane. To the mixture was added dropwise a solution of 9.5 g of methyl iodide in 30 ml of hexane. Then, the mixture was stirred for one hour under the same conditions. The reaction mixture was concentrated under reduced pressure, which was dissolved in ethyl acetate. The solution was washed with water, which was then concentrated under reduced pressure. The concentrate was recrystallized from hexane to give 20 g of the titled compound as colorless needles.

m.p.: 67–68° C.; Elemental Analysis for $C_{16}H_{22}N_2O_4S$ Calcd.: C, 56.78; H, 6.55; N, 8.28; Found : C, 56.63; H, 6.31; N, 8.15.

REFERENCE EXAMPLE 24
3-(4-t-Butoxycarbonylphenylamino)-1,2,4-oxadiazolin-4H-5-one In 350 ml of methanol were dissolved 22.8 g of N-(4-butoxycarbonylphenyl)-N'-ethoxycarbonyl-S-methyl isothiourea and 14 g of hydroxylamine hydrochloride. To the solution was added dropwise, while stirring on an ice-bath, 18 g of triethylamine. The mixture was stirred for further 14 hours at room temperature. The reaction mixture was concentrated under reduced pressure. The concentrate was dissolved in ethyl acetate, and the solution was washed with 1N hydrochloric acid. The organic layer was concentrated under reduced pressure to give a crude product, which was recrystallized from ethyl acetate—hexane to afford 7.8 g of the title compound as colorless prisms.

m.p.: 271–272° C. (decomp.); Elemental Analysis for $C_{13}H_{15}N_3O_4.1/10H_2O$: Calcd.: C, 55.95; H, 5.49; N, 15.06; Found : C, 55.81; H, 5.47; N, 15.05.

REFERENCE EXAMPLE 25
3-(4-Carboxyphenylamino)-1,2,4-oxazolin-4H-5-one

In 70 ml of 1N NaOH was dissolved 7.7 g of 3-(4-t-butoxycarbonylphenylamino)-1,2,4-oxadiazolin-4H-5-one produced in Reference Example 24. The solution was stirred for 1.5 hour at 115° C. The reaction mixture was cooled, which was neutralized with 2N HCl. The resulting precipitate was subjected to extraction with ethyl acetate. The extract solution was concentrated under reduced pressure to give a crude crystalline product, which was washed with ethyl acetate to afford 5.36 g of the title compound as yellow crystals.

m.p.: 272–273° C. (decomp.); Elemental Analysis for $C_9H_7N_3O_4$; Calcd.: C, 47.59; H, 3.40; N, 18.50; Found : C, 47.76; H, 3.39; N, 18,57.

REFERENCE EXAMPLE 26
4-Carboxyphenyl cyanamide

In 180 ml of tetrahydrofuran was dissolved 17.12 g of 4-amino(N-hydroxyimino)methylbenzoic acid methyl ester. To the solution was added 12.12 g of triethylamine. To the mixture was added dropwise, on an ice-bath, 12.65 g of methanesulfonyl chloride. The mixture was stirred for one hour under the same conditions, followed by concentration under reduced pressure. To the concentrate was added methanol. The resulting crystalline precipitate was collected by filtration, which was dissolved in 100 ml of methanol. To the solution was added, while stirring at room temperature, 100 g of water containing 12 g of sodium hydroxide. Methanol was distilled off under reduced pressure. To the residue was added 700 ml of water. To the mixture was added, while stirring at room temperature, 80 ml of 4N HCl. The resulting crystalline precipitate was collected by filtration to give 13.12 g of the title compound as a colorless crystalline product.

m.p.: not lower than 300° C.; Elemental Analysis for $C_8H_6N_2O_2$; Calcd.: C, 59.26; H, 3.73; N, 17.28; Found : C, 58.97; H, 3.82; N, 17.04.

REFERENCE EXAMPLE 27
N-(4-carboxyphenyl)-N'-hydroxyguanidine

In 150 ml of methanol was dissolved 6.56 g of 4-carboxyphenyl cyanamide produced in Reference Example 26. To the solution were added, while stirring at room temperature, 6.1 g of hydroxylamine hydrochloride and 8.88 g of triethylamine. The mixture was stirred for two hours. The resulting crystalline precipitate was collected by filtration to afford 4.45 g of the title compound as a colorless crystalline product.

m.p.: 200–202° C. (decomp.); Elemental Analysis for $C_8H_9N_3O_3$; Calcd.: C, 48.78; H, 4.71; N, 21.33; Found : C, 48.55; H, 4.69; N, 21.09.

REFERENCE EXAMPLE 28
3-(4-Carboxyphenylamino)-5-trifluoromethyl-1,2,4-oxadiazole In 100 ml of tetrahydrofuran was dissolved 4.0 g of N-(4-carboxyphenyl)-N'-hydroxyguanidine produced in Reference Example 27. To the solution was added, while stirring at 0° C., 6.75 g of anhydrous trifluoroacetic acid. The mixture was stirred for 1.5 hour under the same conditions, followed by concentration under reduced pressure. To the concentrate was added water. The resulting crystalline product was collected by filtration, which was recrystallized from ethyl acetate—hexane to afford 3.5 g of the title compound as a colorless crystalline product.

m.p.: 244–246° C.; Elemental Analysis for $C_{10}H_6N_3O_3F_3$: Calcd.: C, 43.97; H, 2.21; N, 15.38; Found : C, 44.06; H, 2.31; N, 15.28.

REFERENCE EXAMPLE 29
4-t-Butoxycarbonyl benzaldoxime

In 100 ml of methanol were dissolved 20.5 g of 4-cyanobenzoic acid t-butyl ester and 13.9 g of hydroxylamine. To the solution was added, while stirring at room temperature, 128 g of triethylamine, and the mixture was stirred for one hour at 85° C. The reaction mixture was concentrated under reduced pressure. The concentrate was dissolved in ethyl acetate, and the solution was washed with water. The organic layer was concentrated under reduced pressure to give a crude product, which was recrystallized from isopropyl ether to afford 11.45 g of the title compound as a colorless crystalline product.

m.p.: 113–114° C.; Elemental Analysis for $C_{12}H_{16}N_2O_3.1/10H_2O$: Calcd.: C, 60.54; H. 6.86; N, 11.77; Found : C, 60.77; H, 6.79; N, 11.57.

REFERENCE EXAMPLE 30
4-t-Butoxycarbonyl phenyl cyanamide

In 150 ml of ethyl acetate was dissolved 16.3 g of 4-t-butoxycarbonyl benzaldoxime produced in Reference Example 29. To the solution was added 13.7 ml of triethylamine. To the mixture was added dropwise, on an ice-bath, 9.92 g of methanesulfonyl chloride. The mixture was stirred for 0.5 hour under the same conditions. The reaction mixture was washed with water. The organic layer was concentrated under reduced pressure to leave an oily product. The oily product was dissolved in 150 ml of tetrahydrofuran, to which was added, while stirring at room temperature, 75 ml of 2N NaOH, followed by stirring for 0.5 hour. Tetrahydrofuran was then distilled off under reduced pressure. The residual solution was neutralized with 2N HCl, which was then subjected to extraction with ethyl acetate, followed by concentration under reduced pressure. The concentrate was recrystallized from hexane-isopropyl ether to afford the title compound as colorless crystals.

m.p.: 94–95° C.; Elemental Analysis for $C_{12}H_{14}N_2O_2.1/10H_2O$: Calcd.: C, 65.50; H, 6.50; N, 12.73; Found : C, 65.51; H, 6.51; N, 12.52.

REFERENCE EXAMPLE 31
N-(4-t-butoxycarbonylphenyl)-N'-methoxycarbonyloxyguanidine In 120 ml of methanol were dissolved 8.72 g of 4-t-butoxycarbonylphenyl cyanamide produced in Reference Example 30 and 5.56 g of hydroxylamine hydrochloride. To the solution was added dropwise 8.80 g of triethylamine at −25° C. The reaction mixture was then warmed up to room temperature and concentrated under reduced pressure. The concentrate was dissolved in ethyl acetate to which was washed with water. To the organic layer were added, at −10° C., 3.26 g of pyridine and 3.78 g of methyl chlorocarbonate. The temperature of the reaction mixture was reverted to room temperature. Then, the reaction mixture was washed with water, and the organic layer was concentrated under reduced pressure to give a crude product. The crude product was recrystallized from isopropyl ether to afford 9.39 g of the title compound as colorless crystals.

m.p.: 122–126° C.; Elemental Analysis for $C_{14}H_{19}N_3O_5$; Calcd.: C, 54.36; H, 6.19; N, 13.58; Found : C, 54.29; H, 6.02; N, 13.41.

REFERENCE EXAMPLE 32
N-(4-carboxyphenyl)-N'-methoxycarbonyloxyguanidine

In 25 ml of trifluoroacetic acid was dissolved 9.2 g of N-(4-t-butoxycarbonylphenyl)-N'-methoxycarbonyloxyguanidine produced in Reference Example 31. The solution was stirred for two hours at room temperature. The reaction mixture was concentrated under reduced pressure, to which was added 100 ml of water. To the mixture was added sodium hydrogencarbonate to adjust the pH to 6. The resulting crystalline precipitate was collected by filtration, followed by recrystallization from tetrahydrofuranethyl acetate to afford 4.53 g of the title compound as a colorless crystalline product.

m.p.: 174–175° C.; Elemental Analysis for $C_{10}H_{11}N_3O_5$; Calcd.: C, 47.43; H, 4.38; N, 16.59; Found : C, 47.17; H, 4.33; N, 16.44.

WORKING EXAMPLE 34
(S)-2-oxo-4-(4-(5-oxo-4,5-dihydro[1,2,4]oxadiazol-3-ylamino)benzoyl]aminoacetyl-3-[4-(5-oxo-4,5-dihydro[1,2,4]oxadiazol-3-ylamino)benzoyl]aminopropylpiperazine-1-acetic acid In 5 ml of trifluoroacetic acid was dissolved 500 mg of (S)-4-benzyloxycarbonylaminoacetyl-3-(3-t-butoxycarbonylaminopropyl)-2-oxopiperazine-1-acetic acid t-butyl ester. The solution was stirred for one hour at room temperature. The reaction mixture was concentrated under reduced pressure to leave an oily product, which was dissolved in 10 ml of methanol. To the solution was added 10 mg of 10% palladium-carbon. The mixture was stirred for one hour at room temperature under hydrogen atmosphere. The catalyst was filtered off, and the filtrate was concentrated under reduced pressure to leave a crude product of (S)-4-aminoacetyl-3-aminopropyl-2-oxopiperazine-1-acetic acid. This product was dissolved in a mixture of 10 ml of water and 10 ml of dioxane. To the solution was added 400 mg of sodium hydrogencarbonate. Subsequently, 420 mg of 3-(4-carboxyphenylamino)-1,2,4-oxadiazolin-4H-5-one produced in Reference Example 25 and 250 mg of N-hydroxysuccinimide were dissolved in 5 ml of dimethylformamide. To the solution was added 450 mg of dicyclohexyl carbodiimide. The mixture was stirred for 3 hours at room temperature, followed by concentration under reduced pressure to leave an oily substance. This substance was dissolved in 5 ml of dioxane, which was added to the solution of (S)-4-aminoacetyl-3-aminopropyl-2-oxopiperazine-1-acetic acid prepared as above. The mixture was stirred for 6 hours at room temperature. The reaction mixture was neutralized with 1N HCl, which was then concentrated under reduced pressure to give a crude product, followed by purification by means of a sephadex LH-20 column to afford 230 mg of the title compound as a colorless amorphous powdery product.

Specific optical rotation: $[\alpha]_D^{20}$ 51.9° (C=0.27, DMSO); Elemental Analysis for $C_{29}H_{30}N_{10}O_{10} \cdot H_2O$: Calcd.: C, 50.00; H, 4.63; N, 20.11; Found : C, 49.79; H, 4.91; N, 19.96.

WORKING EXAMPLE 35
(S)-2-oxo-4-[4-(5-trifluoromethyl[1,2,4]-oxadiazol-3-ylamino)benzoyl]aminoacetyl-3-[4-(5-trifluoromethyl[1,2,4]-oxadiazol-3-ylamino)benzoyl]propylpiperazine-1-acetic acid Using (S)-4-benzyloxycarbonylaminoacetyl-3-(3-t-butoxycarbonylaminopropyl)-2-oxopiperazine-1-acetic acid t-butyl ester produced in Reference Example 2 and 3-(4-carboxyphenylamino)-5-trifluoromethyl-1,2,4-oxadiazole produced in Reference Example 28, the title compound was produced as a colorless amorphous powdery product by substantially the same procedure as in Working Example 34.

Specific optical rotation: $[\alpha]_D^{20}$ 39.7° (C=0.25, DMSO); Elemental Analysis for $C_{31}H_{28}N_{10}O_8F_6 \cdot H_2O$: Calcd.: C, 46.51; H, 3.78; N, 17.49; Found : C, 46.44; H, 3.97; N, 17.26.

WORKING EXAMPLE 36
(S)-4-[4-(N-methoxycarbonyloxyguanidino)benzoylaminoacetyl]-3-[3-(N-methoxycarbonyloxyguanidino)benzoylamino]propyl-2-oxopiperazine-1-acetic acid Employing (S)-4-benzyloxycarbonylaminoacetyl-3-(3-t-butoxycarbonylaminopropyl)-2-oxopiperazine-1-acetic acid t-butyl ester produced in Reference Example 2 and N-(4-carboxyphenyl)-N'-methoxycarbonyloxyguanidine produced in Reference Example 32, the title compound was produced as a colorless amorphous powdery product by substantially the same procedure as in Working Example 34.

Specific optical rotation: $[\alpha]_D^{20}$ 31.20° (C=0.28, DMSO); Elemental Analysis for $C_{31}H_{38}N_{10}O_{12} \cdot 2H_2O$: Calcd.: C, 47.81; H, 5.44; N, 17.99; Found : C, 47.63; H, 5.71; N. 17.83.

REFERENCE EXAMPLE 33
(S)-4-(N-t-butoxycarbonylamino)acetyl-3-(3-t-butoxycarbonylamino)propyl-2-oxopiperazine-1-acetic acid In 10 ml of trifluoroacetic acid was dissolved 1.5 g of (S)-4-benzyloxycarbonylaminoacetyl-3-(3-t-butoxycarbonylaminopropyl)-2-oxopiperazine-1-acetic acid t-butyl ester. The solution was stirred for one hour at room temperature. The reaction mixture was concentrated under reduced pressure to leave an oily substance, which was dissolved in a mixture of 10 ml of water and 10 ml of dioxane. To the solution were added 400 mg of sodium hydrogencarbonate and 700 mg of di-t-butyl dicarbonate. The mixture was stirred for 3 hours at room temperature. Dioxane was distilled off under reduced pressure to leave an aqueous solution, which was washed with ethyl acetate, followed by adjusting the pH to 3 with the addition of potassium hydrogensulfate. The reaction mixture was subjected to extraction with ethyl acetate. The extract solution was dried over anhydrous magnesium sulfate, followed by concentration under reduced pressure to leave 1.2 g of the title compound as colorless crystals.

m.p.: 107–109° C.; Elemental Analysis for $C_{21}H_{36}N_4O_8$; Calcd.: C, 53.38; H, 7.68; N, 11.86; Found : C, 53.35; H, 7.73; N, 11.95.

REFERENCE EXAMPLE 34

(S)-4-(N-benzyloxycarbonylamino)acetyl-3-(3-benzyloxycarbonylamino)propyl-2-oxopiperazine-1-acetic acid In 10 ml of trifluoroacetic acid was dissolved 2.0 g of (S)-4-benzyloxycarbonylaminoacetyl-3-(3-t-butoxycarbonylaminopropyl)-2-oxopiperazine-1-acetic acid t-butyl ester. The solution was stirred for one hour at room temperature. The reaction mixture was concentrated under reduced pressure to leave an oily substance, which was dissolved in a mixture of 10 ml of water and 10 ml of dioxane. To the solution were added 600 mg of sodium hydrogencarbonate and 550 mg of carbobenzoxy chloride. The mixture was stirred for one hour at room temperature. Dioxane was distilled off under reduced pressure to leave an aqueous solution, which was washed with ethyl acetate. To the aqueous solution was added potassium hydrogencarbonate to adjust the pH to 3.5, followed by extraction with ethyl acetate. The extract solution was dried over anhydrous magnesium sulfate, which was then concentrated under reduced pressure to afford 1.5 g of the title compound as a colorless amorphous powdery product.

Elemental Analysis for $C_{27}H_{32}N_4O_8$; Calcd.: C, 59.99; H, 5.97; N, 10.36; Found : C, 60.13; H, 5.87; N, 10.22.

WORKING EXAMPLE 37

(S)-4-(4-guanidinobenzoylamino)acetyl-3-[3-(4-guanidinobenzoylamino)]propyl-2-oxopiperazine-1-acetic acid pivaloyloxymethyl ester dihydrochloride In 5 ml of dimethylformamide were dissolved 500 mg of (S)-4-(N-benzyloxycarbonylamino)acetyl-3-(3-benzyloxycarbonylamino)propyl-2-oxopiperazine-1-acetic acid produced in Reference Example 34, 128 mg of potassium carbonate and 463 mg of potassium iodide. To the solution was added, at room temperature, 420 mg of pivaloyloxy methyl chloride. The mixture was stirred for 12 hours at room temperature. The reaction mixture was concentrated under reduced pressure to leave an oily substance, which was dissolved in ethyl acetate. The solution was washed with 10% aqueous solution of potassium hydrogen sulfate and a saturated aqueous solution of sodium hydrogencarbonate, followed by concentration under reduced pressure. The concentrate was dissolved in 10 ml of methanol, to which was added 100 mg of 10% palladium-carbon. The mixture was stirred for one hour under hydrogen atmosphere. Then, the catalyst was filtered off, and the filtrate was concentrated to leave an oily substance. The oily substance was dissolved in a mixture of 20 ml each of water and dioxane. To the solution were added 400 mg of sodium hydrogencarbonate and 750 mg of 4-guanidinobenzoic acid 3,5-dioxo-4-azatricyclo[5,2,1,0,2,6]deca-8-en-4-ylester hydrochloride. The mixture was stirred for 3 hours at room temperature. Dioxane was distilled off under reduced pressure to leave an aqueous solution, to which was added hydrochloric acid to adjust the pH to 5, followed by purifying by means of a CHP-20 column to afford 240 mg of the title compound as a colorless amorphous powdery product.

Specific optical rotation: $[\alpha]_D^{20}$ 56.23° (C=0.27, H$_2$O); Elemental Analysis for $C_{33}H_{44}N_{10}O_8 \cdot 2HCl \cdot H_2O$: Calcd.: C, 49.56; H, 6.05; N, 17.51; Found : C, 49.31; H, 6.33; N, 17.24.

WORKING EXAMPLE 38

(S)-4-(4-guanidinobenzoylamino)acetyl-3-[3-(4-guanidinobenzoylamino)]propyl-2-oxopiperazine-1-acetic acid 1-(cyclohexyloxycarbonyloxy)ethyl ester dihydrochloride Employing (S)-4-(N-benzyloxycarbonylamino)acetyl-3-(3-benzyloxycarbonylamino)propyl-2-oxopiperazine-1-acetic acid produced in Reference Example 34 and 1-(cyclohexyloxycarbonyloxy)ethyl chloride, the title compound was produced as a colorless amorphous powdery product by substantially the same procedure as in Working Example 37.

Specific optical rotation: $[\alpha]_D^{20}$ 52.5° (C=0.50, H$_2$O); Elemental Analysis for $C_{36}H_{48}N_{10}O_9 \cdot 2HCl \cdot 3H_2O$: Calcd.: C, 48.49; H, 6.33; N, 15.71; Found : C, 48.35; H, 6.33; N, 15.52.

WORKING EXAMPLE 39

(S)-4-(4-guanidinobenzoylamino)acetyl-3-[3-(4-guanidinobenzoylamino)]propyl-2-oxopiperazine-1-acetic acid 5-methyl-2-oxo-1,3-dioxolen-4-ylmethyl ester dihydrochloride In 5 ml of dimethylformamide were dissolved 300 mg of (S)-4-(N-t-butoxycarbonylamino)acetyl-3-(3-t-butoxycarbonylamino)propyl-2-oxopiperazine-1-acetic acid produced in Reference Example 33 and 62 mg of sodium hydrogencarbonate. To the solution was added 115 mg of 5-methyl-2-oxo-1,3-dioxolen-4-ylmethyl bromide, and the mixture was stirred for 5 hours at room temperature. The reaction mixture was concentrated under reduced pressure to leave an oily substance, which was dissolved in ethyl acetate. The solution was washed with a 10% aqueous solution of sodium hydrogencarbonate and a saturated aqueous solution of sodium hydrogencarbonate, followed by concentration under reduced pressure. The concentrate was dissolved in 5 ml of trifluoroacetic acid and stirred for one hour at room temperature, followed by concentration under reduced pressure to leave an oily substance. The oily substance was dissolved in 20 ml each of water and dioxane, to which were added 400 mg of sodium hydrogencarbonate and 500 mg of 4-guanidinobenzoic acid 3,5-dioxo-4-azatricyclo[5,2,2,0,2,6]deca-8-en-4-yl ester hydrochloride. The mixture was stirred for 3 hours at room temperature. Dioxane was distilled off under reduced pressure to leave an aqueous solution, to which was added 1N HCl to adjust the pH to 3.5, followed by purification by means of a CHP-20 column to afford 115 mg of the title compound as a colorless amorphous powdery product.

Specific optical rotation: $[\alpha]_D^{20}$ 43.70° (C=1.0, MeOH); Elemental Analysis for $C_{32}H_{38}N_{10}O_9 \cdot 2HCl \cdot 3H_2O$: Calcd.: C, 46.10; H, 5.56; N, 16.80; Found : C, 46.43; H, 5.41; N, 16.58.

WORKING EXAMPLE 40

(S)-4-(4-guanidinobenzoylamino)acetyl-3-[3-(4-guanidinobenzoylamino)]propyl-2-oxopiperazine-1-acetic acid 2-(isobutyloxycarbonyl)-2-propylidene ethyl ester di-trifluoroacetate Employing (S)-4-(N-t-butoxycarbonylamino)acetyl-3-(3-t-butoxycarbonylamino)propyl-2-oxopiperazine-1-acetic acid produced in Reference Example 33 and 2-(isobutyloxycarbonyl)-2-propylidene ethyl bromide, the title compound was produced as a colorless amorphous powdery product by substantially the same procedure as in Working Example 39.

Specific optical rotation: $[\alpha]_D^{20}$ 47.34° (C=0.48, H$_2$O); Elemental Analysis for $C_{37}H_{50}N_{10}O_8 \cdot 2CF_3CO_2H \cdot 2H_2O$: Calcd.: C, 47.95; H, 5.50; N, 13.64; Found : C, 48.05; H, 5.51; N, 13.54.

WORKING EXAMPLE 41

(S)-4-(4-guanidinobenzoylamino)acetyl-3-[3-(4-guanidinobenzoylamino)]propyl-2-oxopiperazine-1-acetic acid ethyl ester dihydrochloride Employing (S)-4-(N-t-butoxycarbonylamino)acetyl-3-(3-t-butoxycarbonylamino)propyl-2-oxopiperazine-1-acetic acid produced in Reference Example 33 and ethyl iodide, the titled compound was produced as a colorless amorphous powdery product by substantially the same procedure as in Working Example 39.

Specific optical rotation: $[\alpha]_D^{20}$ 49.30° (C=0.47, $H_2O$); Elemental Analysis for $C_{29}H_{38}N_{10}O_6 \cdot 2HCl \cdot 2H_2O$: Calcd.: C, 47.61; H, 6.06; N, 19.14; Found : C, 47.29; H, 6.35; N, 18.88.

REFERENCE EXAMPLE 35

(S,S)-[4-[2-benzyloxycarbonylamino-3-(4-methoxyphenyl) propionyl]-3-(3-tert-butoxycarbonylaminopropyl)-2-oxopiperazin-1-yl]acetic acid tert-butyl ester
(another name: (S,S)-4-[2-benzyloxycarbonylamino-3-(4-methoxyphenyl)propionyl]-3-(3-tertbutoxycarbonylaminopropyl)-2-oxopiperazine-1-acetic acid tert-butyl ester)

In 50 ml of water was dissolved 4.2 g of (S)-[3-(3-tert-butoxycarbonylamino)propyl-2-oxopiperazin-1-yl]acetic acid tert-butyl ester-oxalate (another name: (S)-3-(3-tert-butoxycarbonylamino)propyl-2-oxopiperazine-1-acetic acid tert-butyl ester.oxalate) produced in Reference Example 3. To the solution was added 2.3 g of $NaHCO_3$. The mixture was subjected to extraction twice with 50 ml each portion of dichloromethane. The extract solution was dried ($Na_2SO_4$), followed by concentration under reduced pressure. To the concentrate was added 3 g of Z—Tyr(OMe)—OH, which was dissolved in 150 ml of dichloromethane. To the solution was added 1.92 g of WSC, which was stirred for two hours at room temperature. Dichloromethane was distilled off under reduced pressure, and the residue was subjected to extraction with ethyl acetate. The ethyl acetate layer was washed with a 3% aqueous solution of $KHSO_4$ and a saturated aqueous solution of $NaHCO_3$, which was dried ($Na_2SO_4$), followed by concentration under reduced pressure. The concentrate was purified by means of a silica gel chromatography (Hexane/AcOEt=1:2-AcOEt) to give 5.88 g of the title compound.

$^1$H-NMR(CDCl$_3$) δ: 1.35–2.10(4H,m), 1.41(9H,s), 1.46 (9H,s), 2.30(1H,m), 2.80–3.85(7H,m), 3.41(1H,d,J=17.4 Hz), 3.78(3H,s), 4.24(1H,d,J=17.4 Hz), 4.75(2H,m), 4.94 (1H,t,J=6.5 Hz), 5.10(2H,q,J=12.4 Hz), 5.69(1H,d,J=8.2 Hz), 6.80(2H,d,J=8.6 Hz), 7.09(2H,d,J=8.6 Hz), 7.35(5H,s).

REFERENCE EXAMPLE 36

(S,S)-[3-(3-aminopropyl)-4-[2-benzyloxycarbonylamino-3-(4-methoxyphenyl)propionyl]-2-oxopiperazin-1-yl)]]acetic acid
(another name: (S,S)-3-(3-aminopropyl)-4-[2-benzyloxycarbonylamino-3-(4-methoxyphenyl)propionyl]-2-oxopiperazine-1-acetic acid)

In 20 ml of toluene was suspended 5.7 g of (S,S)-[4-[2-benzyloxycarbonylamino-3-(4-methoxyphenyl)propionyl]-3-(3-tert-butoxycarbonylaminopropyl)-2-oxopiperazin-1-yl]acetic acid tert-butyl ester (another name: (S,S)-4-[2-benzyloxycarbonylamino-3-(4-methoxyphenyl)propionyl]-3-(3-tert-butoxycarbonylaminopropyl)-2-oxopiperazine-1-acetic acid tert-butyl ester) produced in Reference Example 35. The suspension was stirred under ice-cooling, to which was then added 20 ml of trifluoroacetic acid. The mixture was stirred for two hours at room temperature, to which was added toluene, followed by concentration under reduced pressure. The concentrate was dissolved in 30 ml of water, whose pH was adjusted to 5 with a conc. aqueous ammonia, followed by purification by means of an XAD-2 column chromatography (eluting with $H_2O \rightarrow 50\%$ $CH_3CN$ water) to afford 4.3 g of the title compound.

$^1$H-NMR(CD$_3$OD) δ: 1.40–2.10(4H,m), 2.32(1H,m), 2.80–4.00(7H,m), 3.16(1H,d,J=16.5 Hz), 3.77(3H,s), 4.61–4.85(2H,m), 4.72(1H,d,J=16.5 Hz), 5.05(2H,q,J=12.3 Hz), 6.82(2H,d,J=8.4 Hz), 7.11(2H,d,J=8.4 Hz), 7.32(5H,s).

REFERENCE EXAMPLE 37

(S,S)-[4-[2-benzyloxycarbonylamino-3-(4-methoxyphenyl) propionyl]-3-(3-benzyloxycarbonylaminopropyl)-2-oxopiperazin-1-yl]acetic acid
(another name: (S,S)-4-[2-benzyloxycarbonylamino-3-(4-methoxyphenyl)propionyl]-3-(3-benzyloxycarbonylaminopropyl)-2-oxopiperazine-1-acetic acid)

In 100 ml of a 50% aqueous solution of dioxane was dissolved 3.8 g of (S,S)-[3-(3-aminopropyl)-4-[2-benzyloxycarbonylamino-3-(4-methoxyphenyl)propionyl]-2-oxopiperazin-1-yl]acetic acid (another name: (S,S)-3-(3-aminopropyl)-4-[2-benzyloxycarbonylamino-3-(4-methoxyphenyl)propionyl]-2-oxopiperazine-1-acetic acid) produced in Reference Example 36. To the solution was added 1.52 g of $NaHCO_3$, to which was added dropwise, under ice-cooling, 1.24 ml of Z-chloride. The mixture was stirred for 1.5 hour at room temperature. Dioxane was distilled off. To the residue was added a 3% aqueous solution of $KHSO_4$ to adjust the pH to 2. The mixture was subjected to extraction with ethyl acetate. The extract solution was washed with a saturated aqueous solution of $NaHCO_3$ and dried ($Na_2SO_4$), followed by concentration under reduced pressure. To the concentrate was added ether. The mixture was subjected to decantation twice to afford 4 g of the title compound.

$^1$H-NMR(CDCl$_3$) δ: 1.40–2.05(4H,m), 2.22(1H,m), 2.75 (9H,m), 3.74(3H,s), 4.65–5.20(6H,m), 5.52(1H,t,J=5.5 Hz), 5.94(1H,d,J=8.6 Hz), 6.78(2H,d,J=8.6 Hz), 7.05(2H,d,J=8.6 Hz), 7.31(10H,s).

REFERENCE EXAMPLE 38

(S,S)-(4-[2-benzyloxycarbonylamino-3-(4-methoxyphenyl) propionyl)-3-(3-benzyloxycarbonylaminopropyl)-2-oxopiperazin-1-yl]acetic acid tert-butyl ester
(another name: (S,S)-4-[2-benzyloxycarbonylamino-3-(4-methoxyphenyl)propionyl]-3-(3-benzyloxycarbonylaminopropyl)-2-oxopiperazine-1-acetic acid tert-butyl ester)

In 50 ml of dichloromethane were dissolved 1.7 g of (S,S)-[4-[2-benzyloxycarbonylamino-3-(4-methoxyphenyl) propionyl]-3-(3-benzyloxycarbonylaminopropyl)-2-oxopiperazin-1-yl]acetic acid (another name: (S,S)-4-[2-benzyloxycarbonylamino-3-(4-methoxyphenyl)propionyl]-3-(3-benzyloxycarbonylaminopropyl)-2-oxopiperazine-1-acetic acid) produced in Reference Example 37, 2 ml of tert-butanol and 1.6 g of 4-dimethylaminopyridine. To the solution was then added 0.6 g of WSC, and the mixture was stirred for 24 hours at room temperature. Dichloromethane was distilled off, and the residue was subjected to extraction with ethyl acetate. The ethyl acetate layer was washed with water and a saturated aqueous saline solution, which was then dried ($Na_2SO_4$), followed by concentration under reduced pressure. The concentrate was purified by means of a silica gel column chromatography (AcOEt), followed by crystallization from ether/hexane to afford 1.02 g of the title compound as colorless crystals.

m.p.: 138–140° C.; Specific optical rotation: $[\alpha]_D^{20}$ +49.7° (C=0.431, MeOH); Elemental Analysis for $C_{39}H_{48}N_4O_9$(716.832): Calcd.: C, 65.35; H, 6.75; N, 7.82; Found : C, 65.17; H, 6.69; N, 7.91.

REFERENCE EXAMPLE 39

(S,S)-[4-[2-benzyloxycarbonylamino-3-(4-methoxyphenyl) propionyl]-3-[3-(4-guanidinobenzoylamino)propyl]-2-oxopiperazin-1-yl]acetic acid hydrochloride (another name: (S,S)-4-[2-benzyloxycarbonylamino-3-(4-methoxyphenyl)propionyl]-3-[3-(4-guanidinobenzoylamino)propyl]-2-oxopiperazine-1-acetic acid hydrochloride)

In 50 ml of a 50% aqueous solution of dioxane was dissolved 0.5 g of (S,S)-[3-(3-aminopropyl)-4-[2-benzyloxycarbonylamino-3-(4-methoxyphenyl)propionyl]-2-oxopiperazin-1-yl]acetic acid (another name: (S,S)-3-(3-aminopropyl)-4-[2-benzyloxycarbonylamino-3-(4-methoxyphenyl)propionyl]-2-oxopiperazine-1-acetic acid) produced in Reference Example 37. To the solution was added 0.24 g of $NaHCO_3$, to which was then added 0.377 g of 4-guanidinobenzoic acid 3,5-dioxo-4-azatricyclo[5,2,1,0,2,6]deca-8-en-4-yl ester hydrochloride. The mixture was stirred for two hours at room temperature. The pH of the reaction mixture was adjusted to 3 with 1N-HCl, followed by distilling off dioxane. The residue was purified by means of a column chromatography (eluting with $H_2O$→10% aqueous solution of $CH_3CN$→a 20% aqueous solution of $CH_3CN$→a 50% aqueous solution of $CH_3CN$) to afford 0.43 g of the title compound.

$^1$H-NMR($CD_3OD$) δ: 1.50–2.10(4H,m), 2.45(1H,m), 2.80–4.25(9H,m), 3.77(3H,s), 4.60–5.00(2H,m), 5.00(2H,s), 6.83(2H,d,J=8.5 Hz), 7.13(2H,d,J=8.5 Hz), 7.30(5H,s), 7.35 (2H,d,J=8.5 Hz), 7.92(2H,d,J=8.5 Hz).

WORKING EXAMPLE 42

(S,S)-[3-[3-(4-guanidinobenzoylamino)propyl]-4-[3-(4-methoxyphenyl)-2-[4-( 5-trifluoromethyl-[1,2,4]oxadiazol-3-ylamino)benzoylamino]propionyl]-2-oxopiperazin-1-yl] acetic acid hydrochloride (another name: (S,S)-3-[3-(4-guanidinobenzoylamino)-propyl]-4-[3-(4-methoxyphenyl)-2-[4-(5-trifluoromethyl-[1,2,4]oxadiazol-3-ylamino)benzoylamino]propionyl]-2-oxopiperazine-1-acetic acid hydrochloride)

In 40 ml of methanol was dissolved (S,S)-[4-[2-benzyloxycarbonylamino-3-(4-methoxyphenyl)propionyl]-3-[3-(4-guanidinobenzoylamino)propyl]-2-oxopiperazin-1-yl]acetic acid hydrochloride (another name: (S,S)-4-[2-benzyloxycarbonylamino-3-(4-methoxyphenyl)propionyl]-3-[3-(4-guanidinobenzoylamino)propyl]-2-oxopiperazine-1-acetic acid hydrochloride) produced in Reference Example 39. To the solution was added 0.2 g of 10% Pd-C. The mixture was subjected to catalytic reduction for two hours at room temperature. The catalyst was filtered off, and the filtrate was concentrated under reduced pressure, which was dissolved in 50 ml of a 50% aqueous solution of dioxane. To the solution was added dropwise, while maintaining the pH at alkaline side, a dioxane solution of the acid chloride prepared from 4-(5-trifluoromethyl-[1,2,4]oxadiazol-3-ylamino)benzoic acid and oxazolyl chloride. The mixture was stirred for 30 minutes at room temperature. The pH of the reaction mixture was adjusted to 3 with 1N-HCl, then the reaction mixture was concentrated to dryness. The concentrate was purified by means of a silica gel chromatography (AcOEt:AcOH:$H_2O$=8:1:1), to which was added ether to give 0.17 g of the title compound as a colorless powdery product.

Specific optical rotation: $[α]_D^{20}$ +42.8° (C=0.94, DMSO); Elemental Analysis for $C_{37}H_{39}N_{10}O_8F_3$·HCl·0.1$Et_2O$ (852.649): Calcd.: C, 52.68; H, 5.08; N, 16.43; Found : C, 52.62; H, 5.01; N, 16.58.

REFERENCE EXAMPLE 40

(S,S)-[4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoyl-aminogpropyl]piperazin-1-yl]acetic acid tert-butyl ester (another name: (S,S)-4-[3-(4-methoxyphenyl)-2-[4-(5-trifluoromethyl[1,2,4]]oxadiazol-3-ylamino)benzoylamino]propionyl]-2-oxo-3-[3-[4-(5-trifluoromethyl[1,2,4]oxadiazol-3-ylaminobenzoyl-amino]propyl]piperazine-1-acetic acid tert-butyl ester)

In 50 ml of methanol was dissolved 0.54 g of (S,S)-[4-[2-benzyloxycarbonylamino-3-(4-methoxyphenyl)propionyl]-3-(3-benzyloxycarbonylaminopropyl)-2-oxopiperazin-1-yl]acetic acid tert-butyl ester (another name: (S,S)-4-(2-benzyloxycarbonylamino-3-(4-methoxyphenyl)-propionyl]-3-(3-benzyloxycarbonylaminopropyl)-2-oxopiperazine-1-acetic acid tert-butyl ester) produced in Reference Example 38. To the solution was added 0.25 g of 10% Pd-C. The mixture was subjected to catalytic reduction for two hours. The catalyst was filtered off, and the filtrate was concentrated to dryness under reduced pressure. To the concentrate were added 0.41 g of 4(5-trifluoromethyl-[1,2,4]oxadiazol-3-ylamino)benzoic acid and 0.1 g of 4-dimethyl aminopyridine. The mixture was dissolved in 30 ml of acetonitrile. To the solution was added 0.39 g of WSC, and the mixture was stirred for 20 hours. Acetonitrile was distilled off, and the residue was subjected to extraction with ethyl acetate. The extract solution was washed with a 3% aqueous solution of $KHSO_4$ and a saturated aqueous solution of NaCl, which was dried ($Na_2SO_4$), followed by concentration under reduced pressure. The concentrate was purified by means of a silica gel chromatography (AcOEt) to afford 0.44 g of the title compound.

$^1$H NMR($CD_3OD$) δ: 1.45(9H,s), 1.50–2.10(4H,m), 2.47 (1H,m), 2.95–4.20(9H,m), 3.77(3H,s), 4.80–5.20(2H,m), 6.86(2H,d,J=8.6 Hz), 7.20(2H,d,J=8.6 Hz), 7.41(2H,d,J=8.8 Hz), 7.42(2H,d,J=8.8 Hz), 7.72(2H,d,J=8.8 Hz), 7.77(2H,d, J=8.8 Hz).

WORKING EXAMPLE 43

(S,S)-4-[3-(4-methoxyphenyl)-2-[4-(5-trifluoromethyl[1,2,4]oxadiazol-3-ylamino)benzoylaminolpropionyl]-2-oxo-3-[3-[4-(5-trifluoromethyl[1,2,4]oxadiazol-3-ylaminobenzoyl-amino]propyl)piperazin-1-yl]acetic acid (another name: (S,S)-4-[3-(4-methoxyphenyl)-2-[4-(5-trifluoromethyl[1,2,4]oxadiazol-3-ylamino)benzoylamino] propionyl]-2-oxo-3-[3-[4-(5-trifluoromethyl[1,2,4] oxadiazol-3-ylaminobenzoyl-amino]propyl]piperazine-1-acetic acid)

In 6 ml of trifluoroacetic acid was dissolved, under ice-cooling, 0.44 g of (S,S)-[4-[3-(4-methoxyphenyl)-2-[4-(5-trifluoromethyl[1,2,4]oxadiazol-3-ylamino) benzoylamino]propionyl]-2-oxo-3-[3-[4-(5-trifluoromethyl [1,2,4]oxadiazol-3-ylaminobenzoyl-amino]propyl] piperazin-1-yl]acetic acid tert-butyl ester (another name: (S,S)-4-[3-(4-methoxyphenyl)-2-[4-(5-trifluoromethyl[1,2, 4]oxadiazol-3-ylamino)benzoylamino]propionyl]-2-oxo-3-[3-[4-(5-trifluoromethyl[1,2,4]oxadiazol-3-ylaminobenzoyl-amino]propyl]piperazine-1-acetic acid tert-butyl ester) produced in Reference Example 40. The solution was stirred for two hours at room temperature. The reaction mixture was added to toluene, which was twice concentrated to dryness under reduced pressure. The concentrate was dissolved in a small volume of ethyl acetate. To the solution was added ether to give 0.38 g of the title compound as a powdery product.

Specific optical rotation: $[α]_D^{20}$ +0.7° (C=1.043, DMSO); Elemental Analysis for $C_{39}H_{36}N_{10}O_9F_6$·2$H_2O$·0.2AcOEt (956.419): Calcd.: C, 49.08; H, 4.38; N, 14.64; Found : C, 50.17; H, 4.17; N, 14.35.

REFERENCE EXAMPLE 41

(S,S)-[4-(3-(4-methoxyphenyl)-2-[4-(5-oxo-4,5-dihydro[1,2,4]oxadiazol-3-ylamino)benzoyiamino]propionyl]-2-oxo- 3-[4-(5-oxo- 4,5-dihydro[1,2,4]oxadiazol-3-ylamino) benzoylamino]-propyl]piperazin-1-yl]acetic acid tert-butyl ester
(another name: (S,S)-4-[3-(4-methoxyphenyl)-2-[4-(5-oxo-4,5-dihydro[1,2,4]oxadiazol-3-ylamino)benzoylamino] propionyl]-2-oxo-3-[4-(5-oxo-4,5-dihydro[1,2,4]oxadiazol-3-ylamino)benzoylamino]-propyl]piperazine-1-acetic acid tert-butyl ester)

In 50 ml of methanol was dissolved 0.54 g of (S,S)-[4-[2-benzyloxycarbonylamino-3-(4-methoxyphenyl) propionyl]-3-(3-benzyloxycarbonylaminopropyl)-2-oxopiperazin-1-yl)acetic acid tert-butyl ester (another name: (S,S)-4-[2-benzyloxycarbonylamino-3-(4-methoxyphenyl)-propionyl]-3-(3-benzyloxycarbonylaminopropyl)-2-oxopiperazine-1-acetic acid tert-butyl ester) produced in Reference Example 38. To the solution was added 0.25 g of 10% Pd-C. The mixture was subjected to catalytic reduction for two hours. The catalyst was filtered off, and the filtrate was concentrated to dryness under reduced pressure. To the concentrate was added 0.33 g of 4-(5-oxo-4,5-dihydro[1,2,4]oxadiazol-3-ylamino)benzoic acid. The mixture was dissolved in 10 ml of N,N-dimethylformamide, and the solution was stirred under ice-cooling. N,N-dimethylformamide was distilled off under reduced pressure. To the residue was added water, whose pH was adjusted to 2 with a 3% aqueous solution of $KHSO_4$. The solution was subjected to extraction with ethyl acetate containing a small volume of N,N-dimethylformamide. The extract solution was washed with a saturated aqueous solution of NaCl, which was dried ($Na_2SO_4$), followed by concentration under reduced pressure. The concentrate was purified by means of a silica gel chromatography (AcOEt AcOEt/AcOH/$H_2O$=8:1:1) to afford 0.52 g of the title compound.

$^1$H-NMR(CD$_3$OD) δ: 1.44(9H,s), 1.50–2.10(4H,m), 2.48 (1H,m), 2.90–4.20(9H,m), 3.75(3H,s), 4.80–5.20(2H,m), 6.84(2H,d,J=8.4 Hz), 7.18(2H,d,J=8.4 Hz), 7.33(2H,d,J=8.8 Hz), 7.35(2H,d,J=8.8 Hz), 7.71(2H,d,J=8.8 Hz), 7.74(2H,d, J=8.8 Hz).

WORKING EXAMPLE 44
(S,S)-[4-[3-(4-methoxyphenyl)-2-[4-(5-oxo-4,5-dihydro[1,2,4]oxadiazol-3-ylamino)benzoylamino]propionyl]-2-oxo-3-[4-(5-oxo-4,5-dihydro[1,2,4]oxadiazol-3-ylamino) benzoylamino]-propyl]piperazin-1-yl]acetic acid
(another name: (S,S)-4-[3-(4-methoxyphenyl)-2-[4-(5-oxo-4,5-dihydro[1,2,4]oxadiazol-3-ylamino)benzoylamino] propionyl]-2-oxo-3-[4-(5-oxo-4,5-dihydro[1,2,4]oxadiazol-3-ylamino)benzoylamino]-propyl]piperazine-1-acetic acid)

In 6 ml of trifluoroacetic acid was dissolved, under ice-cooling, 0.62 g of (S,S)-[4-[3-(4-methoxyphenyl)-2-[4-(5-oxo-4,5-dihydro[1,2,4]oxadiazol-3-ylamino) benzoylamino]propionyl]-2-oxo-3-[4-(5-oxo-4,5-dihydro[1,2,4]oxadiazol-3-ylamino)benzoylamino]propyl]piperazin-1-yl]acetic acid tert-butyl ester (another name: (S,S)-4-[3-(4-methoxyphenyl)-2-[4-(5-oxo-4,5-dihydro[1,2,4] oxadiazol-3-ylamino)benzoylamino]propionyl]-2-oxo-3-[4-(5-oxo-4,5-dihydro[1,2,4]oxadiazol-3-ylamino) benzoylamino]propyl]piperazine-1-acetic acid tert-butyl ester) produced in Reference Example 41. The solution was stirred for two hours at room temperature. To the reaction mixture was added toluene. The mixture was twice concentrated to dryness under reduced pressure. The concentrate was dissolved in a small volume of methanol, to which was then added ethyl acetate to afford 0.43 g of the title compound as a powdery product.

Specific optical rotation: $[\alpha]_D^{20}$ +7.5° (C=0.983, DMSO); Elemental Analysis for $C_{37}H_{38}N_{10}O_{11} \cdot 1.5H_2O \cdot 0.5AcOEt$ (869.846): Calcd.: C, 53.85; H, 5.21; N, 16.10; Found : C, 53.71; H, 5.05; N, 15.97.

REFERENCE EXAMPLE 42
(S,S)-[4-[2-[4-(3-methoxycarbonyloxyguanidino) benzoylamino-3-(4-methoxyphenyl)propionyl]-3-[3-[4-(3-methoxycarbonyloxyguanidino)benzoyl]amino]propyl-2-oxopiperazin-1-yl]acetic acid tert-butyl ester
(another name: (S,S)-4-[2-[4-(3-methoxycarbonyloxyguanidino)benzoylamino-3-(4-methoxyphenyl)propionyl]-3-[3-[4-(3-methoxycarbonyloxyguanidino)benzoyl]amino]propyl-2-oxopiperazine-1-acetic acid tert-butyl ester)

In 50 ml of methanol was dissolved 0.5 g of (S,S)-[4-[2-benzyloxycarbonylamino-3-(4-methoxyphenyl-propionyl]-3-(3-benzyloxycarbonylaminopropyl)-2-oxopiperazin-1-yl] acetic acid tert-butyl ester (another name: (S,S)-4-[2-benzyloxycarbonylamino-3-(4-methoxyphenylpropionyl]-3-(3-benzyloxycarbonylaminopropyl)-2-oxopiperazine-1-acetic acid tert-butyl ester) produced in Reference Example 38. To the solution was added 0.25 g of 10% Pd-C, and the mixture was subjected to catalytic reduction for two hours. The catalyst was filtered off, and the filtrate was concentrated to dryness under reduced pressure. To the concentrate was added 0.38 g of 4-(3-methoxycarbonyloxyguanidino) benzoic acid. The mixture was dissolved in 10 ml of N,N-dimethylformamide. The solution was stirred under ice-cooling, to which was then added 0.21 ml of triethylamine. To the mixture was further added 0.25 g of diethyl cyanophosphate, followed by stirring for one hour under ice-cooling. To the reaction mixture was added 1 ml of acetic acid. The mixture was subjected to distillation under reduced pressure. The residue was purified by means of a silica gel chromatography (AcOEt→AcOEt/AcOH/$H_2O$=18:1:1) to afford 0.51 g of the title compound.

$^1$H-NMR(CD$_3$OD) δ: 1.44(9H,s), 1.50–2.10(4H,m), 2.48 (1H,m), 2.90–4.20(9H,m), 3.76(3H,s), 3.84(6H,s), 4.80–5.20(2H,m), 6.84(2H,d,J=8.6 Hz), 7.18(2H,d,J=8.6 Hz), 7.33(4H,d,J=8.6 Hz), 7.67(4H,d,J=8.6 Hz).

WORKING EXAMPLE 45
(S,S)-[4-[2-[4-(3-methoxycarbonyloxyguanidino) benzoylamino-3-(4-methoxyphenyl)propionyl]-3-[3-[4-(3-methoxycarbonyloxyguanidino)benzoyl]amino]propyl-2-oxopiperazin-1-yl]acetic acid
(another name: (S,S)-4-[2-[4-(3-methoxycarbonyloxyguanidino)benzoylamino-3-(4-methoxyphenyl)propionyl]-3-[4-(3-methoxycarbonyloxyguanidino)benzoyl]amino]propyl-2-oxopiperazine-1-acetic acid)

In 6 ml of trifluoroacetic acid was dissolved, under ice-cooling, 0.51 g of (S,S)-[4-[2-[4-(3-methoxycarbonyloxyguanidino)benzoylamino-3-(4-methoxyphenyl)propionyl]-3-[4-(3-methoxycarbonyloxyguanidino)benzoyl]amino]propyl-2-oxopiperazin-1-yl]acetic acid tert-butyl ester (another name: (S,S)-4-[2-[4-(3-methoxycarbonyloxyguanidino) benzoylamino-3-(4-methoxyphenyl)propionyl]-3-[3-[4-(3-methoxycarbonyl-oxyguanidino)benzoyl]amino]propyl-2-oxopiperazine-1-acetic acid tert-butyl ester) produced in Reference Example 42. The solution was stirred for two hours at room temperature. To the reaction mixture was added toluene, which was twice subjected to concentration to dryness under reduced pressure. The concentrate was dissolved in a 50% aqueous methanol, which was purified by means of a CHP-20 column chromatography ($H_2O$→20% aqueous methanol→50% aqueous methanol 75% aqueous methanol) to afford 0.2 g of the title compound as a powdery product.

Specific optical rotation: $[\alpha]_D^{20}$ +9.7° (C=1.04, DMSO); Elemental Analysis for $C_{39}H_{46}N_{10}O_{13} \cdot 0.5H_2O$ (871.862):

Calcd.: C, 53.73; H, 5.43; N, 16.07; Found : C, 53.76; H, 5.46; N, 16.09.

WORKING EXAMPLE 46
(S,S)-4-[2-(4-guanidinobenzoyl)amino-3-(4-methoxyphenyl)propionyl]-3-[3-(4-guanidinobenzoyl)aminopropyl]-2-oxopiperazine-1-acetic acid hydrochloride In 5 ml of methanol was dissolved 250 mg of (S,S)-3-(3-aminopropyl)-4-[2-benzyloxycarbonylamino-3-(4-methoxyphenyl)propionyl]-2-oxopiperazine-1-acetic acid produced in Reference Example 36. To the solution was added 100 mg of 10% Pd-C, and the mixture was stirred for one hour at room temperature in hydrogen atmosphere. The catalyst was filtered off, and the filtrate was concentrated under reduced pressure to leave an oily substance. The oily substance was dissolved in a mixture of 10 ml of dioxane and 10 ml of water. To the solution were added 210 mg of sodium hydrogencarbonate and 450 mg of 4-guanidinobenzoic acid 3,5-dioxo-4-azatricyclo[5,2,1,0,2,6]deca-8-en-4-ylester. The mixture was stirred for one hour at room temperature. The pH of the reaction mixture was adjusted to 3 with 1N HCl, then dioxane was distilled off under reduced pressure. The remaining aqueous solution was subjected to a CHP-20 column. The fraction eluted with 10% acetonitrile/water was freeze-dried to afford 130 mg of the title compound as an amorphous powdery product.

Elemental Analysis for $C_{35}H_{42}N_{10}O_7 \cdot 2H_2O$: Calcd.: C, 53.40; H, 6.02; N, 17.79; Found : C, 53.11; H, 5.86; N, 18.06.

WORKING EXAMPLE 47
(S)-[3-[3-(4-amidinobenzoylamino)propyl]-4-[[4-(iminomethoxycarbonylaminomethyl)benzoylamino]acetyl]-2-oxopiperazin-1-yl]acetic acid hydrochloride
(another name: (S)-3-[3-(4-amidinobenzoylamino)propyl]-4-[[4-(iminomethoxycarbonylaminomethyl)benzoylamino]-acetyl]-2-oxopiperazine-1-acetic acid hydrochloride)

In a mixture of 1,4-dioxane (2.0 ml) and $H_2O$ (2.0 ml) was dissolved (S)-[4-[(4-amidinobenzoylamino)acetyl]-3-[3-(4-amidinobenzoylamino)propyl]-2-oxopiperazin-1-yl]acetic acid hydrochloride (another name: (S)-4-[(4-amidinobenzoylamino)acetyl]-3-[3-(4-amidinobenzoylamino)propyl]-2-oxopiperazine-1-acetic acid hydrochloride) produced in Working Example 2 (0.17 g, 0.29 mmol). To the solution was gradually added, under ice-cooling, a 2N aqueous solution of sodium hydroxide (0.46 ml, 0.91 mmol). To the mixture was then added gradually chlorocarbonic acid methyl ester (0.053 ml, 0.69 mmol), which was stirred for 30 minutes. The reaction mixture was adjusted to pH 3 with a 1N HCl, which was concentrated under reduced pressure. The concentrate was purified by means of a column chromatography (CHP-20, $H_2O$-5% $CH_3CNaq$-10% $CH_3CNaq$-15% $CH_3CNaq$), which was led to hydrochloride with 1N HCl to afford the title compound (0.20 g, 91% ) as a colorless powdery product.

Specific optical rotation: $[\alpha]_D^{20}$ +49.7° (C=0.984, MeOH); Elemental Analysis for $C_{29}H_{34}N_8O_8 \cdot 2.0HCl \cdot 2.5H_2O \cdot 1.0MeOH$ (772.640): Calcd.: C, 46.64; H, 5.87; N, 14.50; Found : C, 46.34; H, 5.62; N, 14.26.

WORKING EXAMPLE 48
(S,S)-[4-[2-[4-(3-methoxycarbonylguanidino)benzoylamino]-3-(4-methoxyphenyl)propionyl]-3-[3-[4-(3-methoxycarbonyl-guanidino)benzoylamino]propyl]-2-oxopiperazin-1-yl]acetic acid hydrochloride
(another name: (S,S)-4-[2-[4-(3-methoxycarbonylguanidino)benzoylamino]-3-(4-methoxyphenyl)propionyl]-3-[3-[4-(3-methoxycarbonyl-guanidino)benzoylamino]propyl]-2-oxopiperazine-1-acetic acid hydrochloride)

In a mixture of 1,4-dioxane (5.2 ml) and $H_2O$ (5.2 ml) was dissolved (S,S)-[4-[2-(4-guanidinobenzoylamino)-3-(4-methoxyphenyl)propionyl]-3-[3-(4-guanidinobenzoylamino)propyl]-2-oxopiperazin-1-yl]acetic acid (another name: (S,S)-4-[2-(4-guanidinobenzoylamino)-3-(4-methoxyphenyl)propionyl]-3-[3-(4-guanidinobenzoylamino)propyl]-2-oxopiperazine-1-acetic acid) (0.52 g, 0.73 mmol) produced in Working Example 46. To the solution were added, under ice-cooling, a 2N aqueous solution of sodium hydroxide (4.35 ml, 8.70 mmol) and chlorocarbonic acid methyl ester (0.55 ml, 7.25 mmol) while keeping the pH range of the reaction system at not higher than 10. The mixture was stirred for 30 minutes, whose pH was adjusted to 7 with 1N HCl, followed by concentration under reduced pressure. The concentrate was dissolved in $H_2O$ (5.0 ml), to which was added, under ice-cooling, lithium hydroxide (0.20 g, 4.78 mmol). The mixture was stirred for two hours at 0° C., to which was added 1N HCl to adjust the pH to 3, followed by concentration under reduced pressure. The concentrate was purified by means of a column chromatography [(CHP-20, 10% $CH_3CNaq$-15% $CH_3CNaq$-20% $CH_3CNaq$-25% $CH_3CNaq$) and (LH-20, $H_2O$)] to afford the title compound (0.28 g, 39% ).

Specific optical rotation: $[\alpha]_D^{20}$ +64.4° (C=1.041, MeOH); Elemental Analysis for $C_{39}H_{46}N_{10}O_{11} \cdot 2.0HCl \cdot 4.5H_2O$ (984.845): Calcd.: C, 47.56; H, 5.83; N, 14.22; Found : C, 47.40; H, 5.55; N, 14.33.

REFERENCE EXAMPLE 43
(S,S)-[4-[2-benzyloxycarbonylamino-3-(4-methoxyphenyl)propionyl]-3-(3-benzyloxycarbonylaminopropyl)-2-oxopiperazin-1-yl]acetic acid 1-cyclohexyloxycarbonyloxy ethyl ester
(another name: (s,S)-4-[2-benzyloxycarbonylamino-3-(4-methoxyphenyl)propionyl]-3-(3-benzyloxycarbonylaminopropyl)-2-oxopiperazine-1-acetic acid 1-cyclohexyloxycarbonyloxy ethyl ester).

In DMF (5.8 ml) were dissolved (S,S)-[4-[2-benzyloxycarbonylamino-3-(4-methoxyphenyl)propionyl]-3-(3-benzyloxycarbonylaminopropyl)-2-oxopiperazin-1-yl] acetic acid (another name: (S,S)-4-[2-benzyloxycarbonylamino-3-(4-methoxyphenyl)propionyl]-3-(3-benzyloxycarbonylaminopropyl)-2-oxopiperazine-1-acetic acid) (0.58 g, 0.88 mmol) and triethylamine (0.49 ml, 3.52 mmol). To the solution were added, while stirring at room temperature, carbonic acid 1-chloroethyl ester cyclohexyl ester (0.73 g, 3.52 mmol) and potassium iodide (0.58 g, 3.52 mmol). The mixture was stirred for 38 hours at room temperature, which was then poured into water. To the mixture was added ethyl acetate, and the mixture was shaken for extraction. The organic layer was dried over anhydrous magnesium sulfate, followed by concentration under reduced pressure. The concentrate was purified by means of a silica gel column chromatography (hexane/ethyl acetate= 2/5) to afford the title compound (0.43 g, 59% ) as a colorless amorphous powdery product.

IR $\nu$ max $cm^{-1}$: 3410, 2930, 1755, 1710, 1645, 1510, 1450, 1240, 1075; NMR(CD$_3$OD) δ: 1.10–2.10(14H,m), 1.52(3H,d,J=5.4 Hz), 2.80–5.20(15H,m), 3.77(3H,s), 5.07 (2H,s), 5.09(2H,s), 5.64(1H,d,J=7.8 Hz), 6.67–6.87(2H,m), 7.08(2H,d,J=8.4 Hz), 7.33(10H,s).

WORKING EXAMPLE 49
(S,S)-[4-[2-(4-guanidinobenzoylamino)-3-(4-methoxyphenyl)propionyl]-3-[3-(4- guanidinobenzoylamino)propyl]-2-oxopiperazin-1-yl]acetic acid 1-cyclohexyloxycarbonyloxyethyl ester (another name: (S,S)-4-[2-(4-guanidinobenzoylamino)-3-(4-methoxyphenyl)propionyl]-3-[3-(4-guanidinobenzoylamino)propyl]-2-oxopiperazine-1-acetic acid 1-cyclohexyloxycarbonyloxyethyl ester) In methanol (8.6 ml) were dissolved (S,S)-[4-[2-benzyloxycarbonylamino-3-(4-methoxyphenyl)propionyl]-3-(3-benzyloxycarbonylaminopropyl)-2-oxopiperazin-1-yl] acetic acid 1-cyclohexyloxycarbonyloxyethyl ester (another name: (S,S)-4-[2-benzyloxycarbonylamino-3-(4-methoxyphenyl)propionyl]-3-(3-benzyloxycarbonylaminopropyl)-2-oxopiperazine-1-acetic acid 1-cyclohexyloxycarbonyloxyethyl ester) (0.43 g, 0.52 mmol) produced in Reference Example 43 and acetic acid (0.062 ml, 1.09 mmol). To this solution was added 10% Pd-C (0.17 g), and the mixture was stirred for one hour under hydrogen atmosphere. The catalyst was filtered off, and the filtrate was concentrated under reduced pressure. The concentrate was dissolved in a mixture of 1,4-dioxane (4.3 ml) and $H_2O$ (8.6 ml). To the solution were added, while stirring at room temperature, sodium hydrogencarbonate (0.22 g, 2.59 mmol) and 4-guanidinobenzoic acid N-hydroxy-5-norbornene-2,3-dicarboxyimide ester (0.43 g, 1.14 mmol). One hour later, the pH of the reaction system was adjusted to 3 with 1N HCl, followed by concentration under reduced pressure. The concentrate was purified by means of a column chromatography [(CHP-20, 10% $CH_3CNaq$-15% $CH_3CNaq$-20% $CH_3CNaq$) and (LH-20, $H_2O$)] to afford the title compound (0.073 g, 14%) as a colorless amorphous powdery product.

Specific optical rotation: $[\alpha]_D^{20}$ +63.4° (C=1.009, MeOH); Elemental Analysis for $C_{44}H_{56}N_{10}O_{10} \cdot 2.0HCl \cdot 3.0H_2O$ (1011.957): Calcd.: C, 52.22; H, 6.37; N, 13.84; Found: C, 52.38; H, 6.07; N, 13.81.

REFERENCE EXAMPLE 44

(S,S)-[3-(3-t-butoxycarbonylaminopropyl)-4-[2-[4-(1,3-dimethoxycarbonylguanidino)benzoylamino]-3-(4-methoxyphenyl)propionyl]-2-oxopiperazin-1-yl]acetic acid t-butyl ester (another name: (S,S)-3-(3-t-butoxycarbonylaminopropyl)-4-[2-(4-(1,3-dimethoxycarbonylguanidino)benzoylamino]-3-(4-methoxyphenyl)propionyl]-2-oxopiperazine-1-acetic acid t-butyl ester)

In methanol (6.6 ml) was dissolved (S,S)-[4-[2-benzyloxycarbonylamino-3-(4-methoxyphenyl)propionyl]-3-(3-t-butoxycarbonylaminopropyl)-2-oxopiperazin-1-yl] acetic acid t-butyl ester (another name: (S,S)-4-[2-benzyloxycarbonylamino-3-(4-methoxyphenyl)propionyl]-3-(3-t-butoxycarbonylaminopropyl)-2-oxopiperazine-1-acetic acid t-butyl ester) (0.66 g, 0.97 mmol) produced in Reference Example 5. To the solution was added 10% Pd-C (0.26 g), and the mixture was stirred for one hour under hydrogen atmosphere. The catalyst was filtered off, and the filtrate was concentrated under reduced pressure. The concentrate was dissolved in a mixture of 1,4-dioxane (6.6 ml) and $H_2O$ (6.6 ml). To the solution were added, at room temperature, 4-guanidinobenzoic acid N-hydroxy-5-norbornene-2,3-dicarboximide ester (0.55 g, 1.45 mmol) and sodium hydrogencarbonate (0.12 g, 1.45 mmol). One hour later, the pH of the reaction system was adjusted with 1N HCl, and the reaction mixture was concentrated under reduced pressure. The concentrate was purified by means of a column chromatography (CHP-20, $H_2O$-5% $CH_3CNaq$-10% $CH_3CNaq$-15% $CH_3CNaq$-25% $CH_3CNaq$-30% $CH_3CNaq$) to afford (S,S)-[3-(3-t-butoxycarbonylaminopropyl)-4-[2-(4-guanidinobenzoylamino)-3-(4-methoxyphenyl)propionyl]-2-oxopiperazin-1-yl]acetic acid t-butyl ester (another name: (S,S)-3-(3-t-butoxycarbonylaminopropyl)-4-[2-(4-guanidinobenzoylamino)-3-(4-methoxyphenyl)propionyl]-2-oxopiperazine-1-acetic acid t-butyl ester) (0.50 g, 73%) as a colorless amorphous powdery product. This product was dissolved in 1,4-dioxane (5.0 ml), to which were added, while stirring at 0° C. and keeping the pH of the reaction system at 10 or below, 2N NaOH (2.46 ml, 4.93 mmol) and chlorocarbonic acid methyl ester (0.27 ml, 3.52 mmol). The mixture was stirred for 30 minutes at 0° C., whose pH was adjusted to 3 with 1N HCl, followed by shaking together with ethyl acetate for extraction. The organic layer was dried over anhydrous magnesium sulfate, followed by concentration under reduced pressure. The concentrate was purified by means of a silica gel column chromatography (hexane/ethyl acetate=1/10) to afford the title compound (0.42 g, 72%) as a colorless amorphous powdery product.

IR ν max $cm^{-1}$ (KBr): 3400, 2970, 1730, 1640, 1510, 1490, 1435, 1362, 1245, 1155, 1025, 948; NMR($CD_3OD$) δ: 1.39(9H,s), 1.46(9H,s), 1.20–1.65(2H,m), 1.65–2.06(2H,m), 2.41–2.64(1H,m), 2.88–4.18(7H,m), 3.46(2H,s), 3.59(1H,d, J=17.2 Hz), 3.72(3H,s), 3.77(3H,s), 4.08(1H,d,J=17.2 Hz), 4.78–4.97(1H,m), 5.11(1H,dd,J=6.2,9.2 Hz), 6.85(2H,d,J= 8.4 Hz), 7.19(2H,d,J=8.4 Hz), 7.30(2H,d,J=8.4 Hz), 7.84 (2H,d,J=8.4 Hz).

REFERENCE EXAMPLE 45

(S,S)-[3-(3-t-butoxycarbonylaminopropyl)-4-[2-[4-(3-methoxycarbonylguanidino)benzoylamino]-3-(4-methoxyphenyl)propionyl]-2-oxopiperazin-1-yl]acetic acid t-butyl ester (another name: (S,S)-3-(3-t-butoxycarbonylaminopropyl)-4-[2-[4-(3-methoxycarbonylguanidino)benzoylamino]-3-(4-methoxyphenyl)propionyl]-2-oxopiperazine-1-acetic acid t-butyl ester)

In a mixture of methanol (4.1 ml) and $H_2O$ (0.41 ml) was dissolved (S,S)-[3-(3-t-butoxycarbonylaminopropyl)-4-[2-[4-(1,3-dimethoxy-carbonylguanidino)benzoylamino]-3-(4-methoxyphenyl)-propionyl]-2-oxopiperazin-1-yl]acetic acid t-butyl ester (another name: (S,S)-3-(3-t-butoxycarbonylaminopropyl)-4-[2-[4-(1,3-dimethoxycarbonylguanidino)benzoylamino]-3-(4-methoxyphenyl)-propionyl]-2-oxopiperazine-1-acetic acid t-butyl ester) (0.41 g, 0.50 mmol) produced in Reference Example 44. To the solution was added, under ice-cooling, lithium hydroxide.1.0 hydrate (22.9 mg, 0.55 mmol). The mixture was stirred for 30 minutes at 0° C., followed by adjusting the pH to 4 with 1N HCl. The reaction mixture was concentrated under reduced pressure. The concentrate was purified by means of a silica gel column chromatography (ethyl acetate/methanol=10/1) to afford the title compound (0.36 g, 95%) as a colorless amorphous powdery product.

IR ν max $cm^{-1}$ (KBr): 3400, 2970, 1733, 1640, 1508, 1435, 1360, 1240, 1150; NMR($CD_3OD$) δ: 1.39(9H,s), 1.46(9H,s), 1.20–2.05(4H,m), 2.42–2.64(1H,m), 2.84–4.20 (9H,m), 3.68(3H,s), 3.77(3H,s), 4.80–5.00(1H,m), 5.10(1H, dd,J=9.0,6.4 Hz), 6.84(2H,d,J=8.8 Hz), 7.18(2H,d,J=8.8 Hz), 7.45(2H,d,J=8.8 Hz), 7.82(2H,d,J=8.8 Hz).

WORKING EXAMPLE 50

(S,S)-[3-[3-(4-guanidinobenzoylamino)propyl]-4-[2-[4-(3-methoxycarbonylguanidino)benzoylamino]-3-(4-methoxyphenyl)propionyl]-2-oxopiperazin-1-yl]acetic acid hydrochloride (another name: (S,S)-3-[3-(4-guanidinobenzoylamino) propyl]-4-[2-[4-(3-methoxycarbonylguanidino)

benzoylamino]-3-(4-methoxyphenyl)propionyl]-2-oxopiperazine-1-acetic acid hydrochloride)

In methylene chloride (2.0 ml) was dissolved (S,S)-[3-(3-t-butoxycarbonylaminopropyl)-4-[2-[4-(3-methoxycarbonylguanidino)benzoylamino]-3-(4-methoxyphenyl)propionyl]-2-oxopiperazin-1-yl]acetic acid t-butyl ester (another name: (S,S)-3-(3-t-butoxycarbonylaminopropyl)-4-[2-[4-(3-methoxycarbonylguanidino)benzoylamino]-3-(4-methoxyphenyl)propionyl]-2-oxopiperazine-1-acetic acid t-butyl ester) (0.35 g, 0.46 mmol) produced in Reference Example 45. To the solution was added, while stirring at room temperature, trifluoroacetic acid (2.0 ml). Two hours later, the reaction mixture was concentrated under reduced pressure. The concentrate was dissolved in a mixture of 1,4-dioxane (3.5 ml) and H$_2$O (7.0 ml). To this solution were added, at room temperature, 4-guanidinobenzoic acid N-hydroxy-5-norbornene-2,3-dicarboximide ester (0.19 g, 0.50 mmol) and sodium hydrogencarbonate (0.19 g, 2.28 mmol). One hour later, the pH of the reaction system was adjusted to 2 with a 1N aqueous solution of hydrochloric acid. The reaction mixture was concentrated under reduced pressure. The concentrate was purified by means of a column chromatography (CHP-20, H$_2$O-5% CH$_3$CNaq-10% CH$_3$CNaq-15% CH$_3$CNaq-20% CH$_3$CNaq-25% CH$_3$CNaq), which was processed with a 1N aqueous solution of hydrochloric acid to lead to the corresponding hydrochloride, i.e. the title compound (0.29 g, 69%) as a colorless amorphous powdery product.

Specific optical rotation: $[\alpha]_D^{20}$ +69.9° (C=1.025, MeOH); Elemental Analysis for C$_{37}$H$_{44}$N$_{10}$O$_9$.2.0HCl.4.0H$_2$O (917.801): Calcd.: C, 48.42; H, 5.93; N, 15.26; Found : C, 48.30; H, 5.78; N, 15.20.

WORKING EXAMPLE 51

(S)-[4-[[4-(3-methoxycarbonylguanidino)-benzoylamino]acetyl]-3-[3-[4-(3-methoxycarbonylguanidino)benzoylamino]propyl]-2-oxopiperazin-1-yl]acetic acid hydrochloride
(another name: (S)-4-[[4-(3-methoxycarbonylguanidino)benzoylamino]acetyl]-3-[3-[4-(3-methoxycarbonylguanidino)benzoylamino]propyl]-2-oxopiperazine-1-acetic acid hydrochloride)

In a mixture of 1,4-dioxane (3.0 ml) and H$_2$O (3.0 ml) was dissolved (S)-[4-[(4-guanidinobenzoylamino)acetyl]-3-[3-(4-guanidino-benzoylamino)propyl]-2-oxopiperazin-1-yl] acetic acid hydrochloride (another name: (S)-4-[(4-guanidinobenzoylamino)acetyl]-3-[3-(4-guanidino-benzoylamino)propyl]-2-oxopiperazine-1-acetic acid hydrochloride) (0.3 g, 0.51 mmol) produced in Working Example 15. To the solution were added gradually, under stirring at 0° C. while keeping the pH at 10 or below, a 2N aqueous solution of sodium hydroxide (2.60 ml, 5.10 mmol) and chlorocarbonic acid methyl ester (0.31 ml, 4.00 mmol). The reaction mixture was stirred for 10 minutes at 0° C., whose pH was adjusted to 4 with a 1N aqueous solution of hydrochloric acid, followed by shaking together with ethyl acetate for extraction. The organic layer was dried over anhydrous magnesium sulfate, followed by concentration under reduced pressure. The concentrate was purified by means of a column chromatography (CHP-20, 10% CH$_3$CNaq-15% CH$_3$CNaq-20% CH$_3$CNaq-25% CH$_3$CNaq-35% CH$_3$CNaq) to give (S)-[4-[[4-(1,3-dimethoxycarbonylguanidino)benzoylamino]acetyl]-3-[3-[4-(1,3-dimethoxycarbonylguanidino)benzoylamino]propyl]-2-oxopiperazin-1-yl]acetic acid (another name: (S)-4-[[4-(1,3-dimethoxycarbonylguanidino)-benzoylamino]acetyl]-3-[3-[4-(1,3-dimethoxycarbonylguanidino)benzoylamino]-propyl]-2-oxopiperazine-1-acetic acid) (0.26 g, 62%) as a colorless amorphous powdery product. This product (0.26 g, 0.31 mmol) was dissolved in a mixture of methanol (2.6 ml) and H$_2$O (0.26 ml). To the solution was added, under ice-cooling, lithium hydroxide.1.0hydrate (42 mg, 1.00 mmol). One hour later, the reaction system was adjusted to pH 4 with a 1N aqueous solution of hydrochloric acid, followed by concentration under reduced pressure. The concentrate was purified by means of a column chromatography [(CHP-20, 5% CH$_3$CNaq-10% CH$_3$CNaq-15% CH$_3$CNaq-20% CH$_3$CNaq) and (LH-20, H$_2$O)] to afford the title compound (0.13 g, 58%) as a colorless amorphous powdery product.

Specific optical rotation: $[\alpha]_D^{20}$ +48.2° (C=1.043, MeOH); Elemental Analysis for C$_{31}$H$_{38}$N$_{10}$O$_{10}$.1.0HCl.3.0H$_2$O (801.211): Calcd.: C, 46.47; H, 5.66; N, 17.48; Found : C, 46.30; H, 5.38; N, 17.35.

REFERENCE EXAMPLE 46

(S)-[3-(3-t-butoxycarbonylaminopropyl)-4-[(4-guanidinobenzoylamino)acetyl]-2-oxopiperazin-1-yl)acetic acid t-butyl ester
(another name: (S)-3-(3-t-butoxycarbonylaminopropyl)-4-[(4-guanidinobenzoyl-amino)acetylj-2-oxopiperazine-1-acetic acid t-butyl ester)

In ethyl acetate (7.0 ml) was dissolved (S)-[4-benzyloxycarbonylaminoacetyl-3-(3-t-butoxycarbonyl-aminopropyl)-2-oxopiperazin-1-yl)acetic acid t-butyl ester (another name: (S)-4-benzyloxycarbonylaminoacetyl-3-(3-t-butoxycarbonyl-aminopropyl)-2-oxopiperazine-1-acetic acid t-butyl ester) (0.70 g, 1.24 mmol) produced in Reference Example 2. To the solution was added 10% Pd-C (0.21 g), which was stirred for one hour at room temperature under hydrogen atmosphere. The catalyst was filtered off, and the filtrate was concentrated under reduced pressure. The concentrate was dissolved in a mixture of 1,4-dioxane (7.0 ml) and H$_2$O (7.0 ml). To the solution was added, at room temperature, 4-guanidinobenzoic acid N-hydroxy-5-norbornene-2,3-dicarboximide ester (0.56 g, 1.49 mmol). One hour later, the reaction system was adjusted to pH 4 with a 1N aqueous solution of hydrochloric acid, which was concentrated under reduced pressure. The concentrate was purified by means of a column chromatography (CHP-20, H$_2$O-5% CH$_3$CNaq-10% CH$_3$CNaq-15% CH$_3$CNaq-20% CH$_3$CNaq) to afford the title compound (0.70 g, 96%) as a colorless amorphous powdery product.

IR ν max cm$^{-1}$ (KBr): 3320, 2970, 2920, 1730, 1640, 1560, 1500, 1445, 1360, 1250, 1155; NMR(CD$_3$OD) δ: 1.42(9H,s), 1.48(9H,s), 1.02–2.17(4H,m), 2.90–3.20(2H,m), 3.36–4.64(6H,m), 4.00(1H,d,J=17.5 Hz), 4.12(1H,d,J=17.5 Hz), 4.82–5.03(1H,m), 7.38(2H,d,J=8.6 Hz), 7.97(2H,d,J= 8.6 Hz).

REFERENCE EXAMPLE 47

(S)-[3-(3-t-butoxycarbonylaminopropyl)-4-[[4-(1,3-dimethoxycarbonylguanidino)benzoylamino]acetyl]-2-oxopiperazin-1-yl]acetic acid t-butyl ester
(another name: (S)-3-(3-t-butoxycarbonylaminopropyl)-4-[[4-(1,3-dimethoxycarbonylguanidino)benzoylamino]-acetyl]-2-oxopiperazine-1-acetic acid t-butyl ester)

In a mixture of 1,4-dioxane (7.0 ml) and H$_2$O (7.0 ml) was dissolved (S)-[3-(3-t-butoxycarbonylaminopropyl)-4-[(4-guanidinobenzoyl-amino)acetyl]-2-oxopiperazin-1-yl] acetic acid t-butyl ester (another name: (S)-3-(3-t-butoxycarbonylaminopropyl)-4-[(4-guanidinobenzoyl-amino)acetyl]-2-oxopiperazine-1-acetic acid t-butyl ester) (0.70 g, 1.19 mmol) produced in Reference Example 46. To the solution were added gradually, under stirring at 0° C.

while keeping the pH of the reaction system at 10 or below, a 2N aqueous solution of sodium hydroxide (4.20 ml, 8.33 mmol) and chlorocarbonic acid methyl ester (0.46 ml, 5.94 mmol). The mixture was stirred for 30 minutes at 0° C., then the reaction system was adjusted to pH 4 with a 1N aqueous solution of hydrochloric acid, which was shaken together with ethyl acetate for extraction. The organic layer was dried over anhydrous magnesium sulfate, which was concentrated under reduced pressure. The concentrate was purified by means of a silica gel column chromatography (ethyl acetate/methanol=13/1) to afford the title compound (0.67 g, 80%) as a colorless amorphous powdery product.

IR ν max cm$^{-1}$ (KBr): 3380, 2970, 1730, 1640, 1490, 1433, 1362, 1250, 1155; NMR(CD$_3$OD) δ: 1.42(9H,s), 1.48(9H,s), 1.30–2.15(4H,m), 2.98–3.20(2H,m), 3.45(3H,s), 3.72(3H,s), 3.34–4.70(8H,m), 4.85–5.05(1H,m), 7.32(2H,d, J=8.5 Hz), 7.91(2H,d,J=8.5 Hz).

REFERENCE EXAMPLE 48

(S)-[3-(3-t-butoxycarbonylaminopropyl)-4-[[4-(3-methoxycarbonylguanidino)benzoylamino]acetyl]-2-oxopiperazin-1-yl]acetic acid t-butyl ester
(another name: (S)-3-(3-t-butoxycarbonylaminopropyl)-4-[[4-(3-methoxycarbonylguanidino)benzoylamino]acetyl]-2-oxopiperazine-1-acetic acid t-butyl ester)

In a mixture of methanol (6.7 ml) and H$_2$O (0.67 ml) was dissolved (S)-(3-(3-t-butoxycarbonylaminopropyl)-4-[[4-(1,3-dimethoxy-carbonylguanidino)benzoylamino]acetyl]-2-oxopiperazin-1-yl]acetic acid t-butyl ester (another name: (S)-3-(3-t-butoxycarbonylaminopropyl)-4-[[4-(1,3-dimethoxy-carbonylguanidino)benzoylamino]acetyl]-2-oxopiperazine-1-acetic acid t-butyl ester) (0.67 g, 0.95 mmol) produced in Reference Example 47. To the solution was added, under ice-cooling, lithium hydroxide.1.0 hydrate (45.8 mg, 1.09 mmol). The mixture was stirred for 30 minutes at 0° C., and the reaction mixture was adjusted to pH 4 with a 1N aqueous solution of hydrochloric acid, followed by concentration under reduced pressure. The concentrate was purified by means of a silica gel column chromatography (ethyl acetate/methanol=10/1-5/1) to afford the title compound (0.44 g, 72%) as a colorless amorphous powdery product.

IR ν max cm$^{-1}$ (KBr): 3390, 2970, 2925, 1730, 1640, 1525, 1435, 1360, 1240, 1155; NMR(CD$_3$OD) δ: 1.42(9H, s), 1.47(9H,s), 1.20–2.14(4H,m), 2.96–3.18(2H,m), 3.68 (3H,s), 3.98(1H,d,J=17.4 Hz), 4.12(1H,d,J=17.4 Hz), 3.22–4.66(6H,m), 4.82–5.04(1H,m), 7.45(2H,d,J=8.6 Hz), 7.86(2H,d,J=8.6 Hz).

WORKING EXAMPLE 52

(S)-[3-[3-(4-guanidinobenzoylamino)propyl]-4-[[4-(3-methoxycarbonylguanidino)benzoylamino]acetyl]-2-oxopiperazin-1-yl]acetic acid trifluoroacetate
(another name: (S)-3-[3-(4-guanidinobenzoylamino)-propyl]-4-[[4-(3-methoxycarbonylguanidino)-benzoylamino]acetyl]-2-oxopiperazine-1-acetic acid trifluoroacetate)

In methylene chloride (4.4 ml) was dissolved (S)-[3-(3-t-butoxycarbonylaminopropyl)-4-[[4-(3-methoxy-carbonylguanidino)benzoylamino]acetyl]-2-oxopiperazin-1-yl]acetic acid t-butyl ester (another name: (S)-3-(3-t-butoxycarbonylaminopropyl)-4-[[4-(3-methoxy-carbonylguanidino)benzoylamino]acetyl]-2-oxopiperazine-1-acetic acid t-butyl ester) (0.44 g, 0.68 mmol) produced in Reference Example 48. To the solution was added, while stirring at room temperature, trifluoroacetic acid (4.4 ml). One hour later, the reaction system was concentrated under reduced pressure. The concentrate was dissolved in a mixture of 1,4-dioxane (4.4 ml) and H$_2$O (4.4 ml). To this solution were added, at room temperature, 4-guanidinobenzoic acid N-hydroxy-5-norbornene-2,3-dicarboximide ester (0.31 g, 0.82 mmol) and sodium hydrogencarbonate (0.29 g, 3.40 mmol). One hour later, the reaction system was adjusted to pH 2 with a 1N aqueous solution of hydrochloric acid, which was concentrated under reduced pressure. The concentrate was purified by means of a column chromatography [(CHP-20, H$_2$O-5% CH$_3$CNaq-10% CH$_3$CNaq-15% CH$_3$CNaq) and (LH-20, H$_2$O)] to afford the title compound (0.18 g, 32%) as a colorless amorphous powdery product.

Specific optical rotation: $[\alpha]_D^{20}$ +46.9° (C=0.976, MeOH); Elemental Analysis for C$_{29}$H$_{36}$N$_{10}$O$_8$.1.0CF$_3$CO$_2$H.3.0H$_2$O (820.737): Calcd.: C, 45.37; H, 5.28; N, 17.07; Found : C, 45.42; H, 5.08; N, 16.92.

INDUSTRIAL APPLICABILITY

The present invention provides compounds and medicines effective for prophylaxis and therapy of various diseases by controlling or inhibiting cell-adhesion. Especially, the compounds of this invention perform platelet aggregation action without remarkable elongation of hemorrhagic period and can be used as a safe and long-acting antithrombotic drug, as compared with known substances showing the same activity.

We claim:

1. (S)-4-(4-guanidinobenzoylamino)acetyl-3-[3-(4-guanidinobenzoylamino)propyl]-2-oxopiperazine-1-acetic acid or a pharmaceutically acceptable salt thereof.

2. (S)-4-(4-guanidinobenzoylamino)acetyl-3-[3-(4-guanidinobenzoylamino)propyl]-2-oxopiperazine-1-acetic acid hydrochloride.

3. A pharmaceutical composition which comprises a compound of claim 1 or a pharmaceutically acceptable salt thereof.

4. A pharmaceutical composition which comprises a compound of claim 2.

5. A method for treating thrombosis, comprising administering to a mammal an effective amount of the compound of claim 1 or a pharmaceutically acceptable salt thereof.

6. A method for treating thrombosis, comprising administering to a mammal an effective amount of the compound of claim 2.

* * * * *